United States Patent [19]

Minami et al.

[11] Patent Number: 5,292,770
[45] Date of Patent: Mar. 8, 1994

[54] BUTENOIC ACID DERIVATIVES

[75] Inventors: Norio Minami; Fumihiro Ozaki; Keiji Ishibashi; Yasuhiro Kabasawa; Toshiaki Ogawa; Hideyuki Adachi; Takanori Kawamura, all of Ibaraki, Japan

[73] Assignee: Eisai Co., Ltd., Tokyo, Japan

[21] Appl. No.: 960,883

[22] Filed: Oct. 14, 1992

Related U.S. Application Data

[60] Division of Ser. No. 837,599, Feb. 20, 1992, Pat. No. 5,166,188, which is a continuation of Ser. No. 518,508, May 3, 1990, abandoned.

[30] Foreign Application Priority Data

May 19, 1989 [JP] Japan .................. 1-126174
Nov. 29, 1989 [JP] Japan .................. 1-309866

[51] Int. Cl.$^5$ .................. A61K 31/44; A61K 31/415; C07D 401/04
[52] U.S. Cl. .................. 514/341; 514/338; 546/270; 546/278
[58] Field of Search .............. 546/278, 270; 514/341, 514/338

[56] References Cited

FOREIGN PATENT DOCUMENTS 0344577 12/1989 European Pat. Off. .

OTHER PUBLICATIONS

Journal Med. Chem. vol. 29; No. 1, pp. 19-25 (1979).

*Primary Examiner*—Johann Richter
*Attorney, Agent, or Firm*—Birch, Stewart, Kolasch and Birch

[57] ABSTRACT

A butenoic acid compound is defined by the following formula:

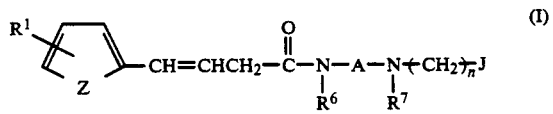

in which Z is O,S, vinylene or azomethyne, A is an alkylene and J is phenyl or etc. It is useful to treat the heart desease.

4 Claims, No Drawings

BUTENOIC ACID DERIVATIVES

This application is a divisional of copending application Ser. No. 07/837,599, filed on Feb. 20, 1992, now U.S. Pat. No. 5,166,188, which is a Rule 62 continuation application of Ser. No. 07/518,508, filed on May 3, 1990, now abandoned, the entire contents of which are hereby incorporated by reference.

The present invention relates to a butenoic acid derivative having an excellent activity as a drug.

BACKGROUND OF THE INVENTION AND PRIOR ART

In Europe and America, cardiovascular diseases top the list of death causes. Meanwhile, although cerebrovascular diseases such as cerebral apoplexy rather ranked high in death causes in Japan, a tendency for ischemic heart diseases to increase rapidly has been recently seen as the life-style and diet have neared those of Europe and America.

The term "ischemic heart disease" refers to a series of diseases generally caused when the supply of oxygen to the cardiac muscle does not meet the demand of the muscle for oxygen. Representative examples thereof include coronary arteriosclerosis, acute myocardial infarction and stenocardia. Although a nitro drug, calcium antagonist or $\beta$-blocker is now used for the treatment of the above diseases, no sufficiently effective drug has been found as yet. Accordingly, the development of a new drug superior to those of the prior art has been expected.

CONSTITUTION AND EFFECT OF THE INVENTION

The inventors of the present invention have studied for a long time to obtain a new type of remedy for ischemic heart diseases and have found that the butenoic acid derivative which will be described below exhibits an excellent coronary vasodilating effect.

Namely, the compound of the present invention is a butenoic acid derivative represented by the following general formula (I) or a pharmacologically acceptable salt thereof:

$$R^1\underset{Z}{\diagdown}\!\!\!-CH=CHCH_2-\overset{O}{\overset{\|}{C}}-\underset{R^6}{\overset{|}{N}}-A-\underset{R^7}{\overset{|}{N}}-(CH_2)_n-J \quad (I)$$

wherein
$R^1$ represents a heteroaryl group, a group represented by the formula:

$$\underset{R^{2'}}{\overset{R^2}{\diagdown}}\!\!\!N-\overset{X}{\overset{\|}{C}}-NH-$$

{wherein $R^2$ and $R^{2'}$ may be the same or different from each other and each represent a hydrogen atom or a lower alkyl, cycloalkyl or allyl group, or alternatively, $R^2$ and $R^{2'}$ may together form a ring, X represents an oxygen or sulfur atom, a group represented by the formula: $=N-R^3$ (wherein $R^3$ represents a cyano, lower alkanoyl, lower alkoxycarbonyl, carbamoyl, sulfamoyl, alkylsulfonyl, arylsulfonyl or nitro group) or a group represented by the formula:

$$=C\underset{R''}{\overset{R'}{\diagup}}$$

(wherein R' and R'' may be the same or different from each other and each represent a hydrogen atom or an alkylsulfonyl, arylsulfonyl or nitro group)}, a group represented by the formula:

$$\underset{R^4-\overset{\|}{C}-NH-}{\overset{R^5\diagdown_N}{}}$$

{wherein $R^4$ represents a hydrogen atom or a lower alkyl, cycloalkyl or allyl group and $R^5$ represents a cyano, lower alkylcarbonyl, lower alkoxycarbonyl, carbamoyl or sulfamoyl group}, or a group represented by the formula: E—NH— (wherein E represents a heteroaryl group which may be substituted), Z represents an oxygen or sulfur atom or a vinylene (—CH=CH—) or azomethyne (—N=CH—) group, $R^6$ and $R^7$ may be the same or different from each other and each represent a hydrogen atom or a lower alkyl, cycloalkyl or allyl group, A represents a $C_{1-6}$ alkylene group which may have a lower alkyl or hydroxy-substituted lower alkyl substituent bonded to any carbon of the group, J represents a group represented by the formula:

$$\underset{R^{10}}{\overset{R^8\quad R^9}{\diagdown\!\!\diagup}}$$

{wherein $R^8$, $R^9$ and $R^{10}$ may be the same or different from each other and each represent a hydrogen or halogen atom, a lower-alkyl, lower alkoxy, hydroxyl, nitro, cyano or trifuloromethyl group, a group represented by the formula:

$$-N\underset{R^{12}}{\overset{R^{11}}{\diagup}}$$

(wherein $R^{11}$ and $R^{12}$ may be the same or different from each other and each represent a hydrogen atom or a lower alkyl group) or an alkanoylamino group, or alternatively, any two members among $R^8$, $R^9$ and $R^{10}$ may form an alkylenedioxy group together with adjacent carbon atoms}, and n represents an integer of 1 to 6.

In the above definition, when Z is a group represented by the formula: —CH=CH—, i.e., when the group represented by the formula:

$$\underset{Z}{\diagdown\!\!\diagup}$$

is a phenyl group, the compound of the present invention is a butenoic acid derivative represented by the following general formula (I'):

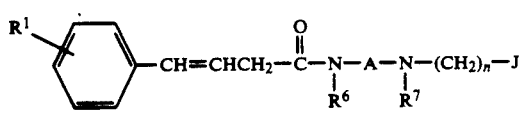 (I')

wherein $R^1$ represents a heteroaryl group, a group represented by the formula:

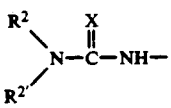

{wherein $R^2$ and $R^{2'}$ may be the same or different from each other and each represent a hydrogen atom or a lower alkyl, cycloalkyl or allyl group, or alternatively, $R^2$ and $R^{2'}$ may together form a ring, X represents an oxygen or sulfur atom, a group represented by the formula: $=N-R^3$ (wherein $R^3$ represents a cyano, lower alkanoyl, lower alkoxycarbonyl, carbamoyl, sulfamoyl, alkylsulfonyl, arylsulfonyl or nitro group) or a group represented by the formula:

(wherein R' and R" may be the same or different from each other and each represent a hydrogen atom or an alkylsulfonyl, arylsulfonyl or nitro group)}, a group represented by the formula:

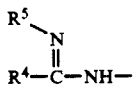

{wherein $R^4$ represents a hydrogen atom or a lower alkyl, cycloalkyl or allyl group and $R^5$ represents a cyano, lower alkylcarbonyl, lower alkoxycarbonyl, carbamoyl or sulfamoyl group}, or a group represented by the formula: E—NH— (wherein E represents a heteroaryl group which may be substituted), $R^6$ and $R^7$ may be the same or different from each other and each represent a hydrogen atom or a lower alkyl, cycloalkyl or allyl group, A represents a $C_{1\sim6}$ alkylene group which may have a lower alkyl or hydroxy-substituted lower alkyl substituent bonded to any carbon of the group, J represents a group represented by the formula:

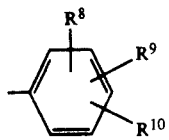

{wherein $R^8$, $R^9$ and $R^{10}$ may be the same or different from each other and each represent a hydrogen or halogen atom, a lower alkyl, lower alkoxy, hydroxyl, nitro, cyano or trifluoromethyl group, a group represented by the formula:

(wherein $R^{11}$ and $R^{12}$ may be the same or different from each other and each represent a hydrogen atom or a lower alkyl group) or an alkanoylamino group, or alternatively, any two members among $R^8$, $R^9$ and $R^{10}$ may form an alkylenedioxy group together with adjacent carbon atoms}, and n represents an integer of 1 to 6.

The lower alkyl group defined with respect to $R^2$, $R^{2'}$, $R^4$, $R^6$, $R^7$, $R^8$, $R^9$, $R^{10}$, $R^{11}$ and $R^{12}$ in the above definition of the compound (I) according to the present invention may be a $C_{1\sim6}$ straight-chain or branched alkyl group and examples thereof include methyl, ethyl, n-propyl, n-butyl, isopropyl, isobutyl, sec-butyl, n-pentyl, 1-ethylpropyl, isoamyl and n-hexyl groups, among which methyl and ethyl groups are most preferred.

The lower alkoxy group defined with respect to $R^8$, $R^9$ and $R^{10}$ may be one derived from any of the lower alkyl groups described above.

The lower alkoxycarbonyl group defined with respect to $R^3$ and $R^5$ may be one derived from any of the lower alkyl groups described above.

The heteroaryl group defined with respect to $R^1$ is a substituted or unsubstituted heterocyclic group. The heterocyclic group may contain one or more nitrogen atoms. Particular examples thereof include imidazolyl groups such as 1-imidazolyl and 2-imidazolyl groups; and 3-pyridyl, 4-pyridyl, 1,4-dihydro-4-oxo-1-pyridyl, 1,4-dihydro-4 oxo-2-pyridyl, 1-oxy-4-pyridyl and 1,4-dihydro-4-oxo-3-pyridyl, among which 1-imidazolyl, 1-oxy-4-pyridyl and 1,4-dihydro-4-oxo-1-pyridyl are most preferred.

These heteroaryl groups may be each one derived from a heteroaryl group substituted with a lower alkyl group such as a methyl group.

As described above, a preferred example of the heteroaryl group is a substituted or unsubstituted 1-imidazolyl group which follows:

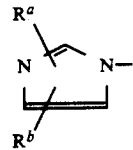

In the above formula, $R^a$ and $R^b$ may be the same or different from each other and each represent a hydrogen atom, a nitro, cyano, trifluoromethyl, alkylsulfonyl or arylsulfonyl group, a halogen atom or a lower alkoxycarbonyl group.

Among them, a group represented by the formula wherein $R^a$ is a 4-nitro group and $R^b$ is H is preferred.

The heteroaryl group defined with respect to E may be a substituted or unsubstituted heterocyclic group. Preferred examples thereof include five or six-membered ring groups each containing one or more nitrogen atoms. These groups may be each substituted with, for example, a lower alkyl group such as methyl or a lower alkoxy group such as methoxy. Alternatively, the carbon atom constituting the ring may form a carbonyl group together with an oxygen atom. Representative examples of such a group include

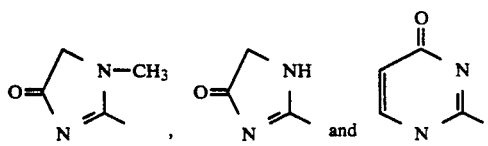 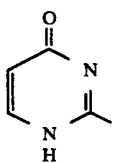 and 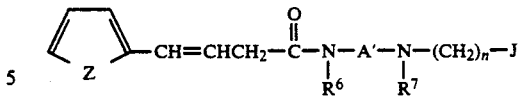

R³ represents a cyano, lower alkanoyl, lower alkoxycarbonyl, carbamoyl, sulfamoyl, alkylsulfonyl, arylsulfonyl or nitro group, among which cyano group is most preferred.

The alkanoylamino group defined with respect to R⁸, R⁹ and R¹⁰ is one derived from any of the lower alkyl groups particularly described above.

A represents an alkylene group having 1 to 6 carbon atoms, preferably 3 or 4 carbon atoms. The alkylene group may be substituted with a lower alkyl group as described above or a hydroxy-substituted lower alkyl group (for example, a methyl or hydroxymethyl group) at any carbon of the alkylene group.

J represents a group represented by the formula:

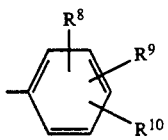

(wherein R⁸, R⁹ and R¹⁰ are each as defined above). Particularly, it is preferred that 1 to 3 members out of R⁸, R⁹ and R¹⁰ are each a lower alkyl group, still preferably a methyl group.

In compound of the invention, that having the following formula (A) is preferable.

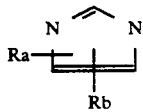

(A)

In the formula (A), Ra and Rb are, independently of each other, hydrogen, nitro, cyano, trifluoromethyl, an alkylsulfonyl, an arylsulfonyl, a halogen or a lower alkylcarbonyl, Z is vinylene, oxygen, sulfur or azomethyne, R6 and R7 and J are the same as defined in the formula (I), A' is an alkylene having 4 to 6 carbon atoms and n is an integer of 1 to 6.

The compound of the formula (A) having hydrogen for both Ra and Rb is most preferable. Secondly preferable is the compound having hydrogen for Ra and nitro or cyano for Rb. The vinylene for Z to form a phenyl ring is most preferable. Secondly preferable is sulfur for Z. Hydrogen or a lower alkyl for R6 and R7 is preferable. Methyl is most preferable in the alkyl. Hydrogen for R6 and methyl for R7 are most preferable. A' is preferred to be an alkylene having 4 carbon atoms. 2 for n is most preferable. The phenyl for J is preferred to have a lower alkoxy having 1 to 3 carbon atoms, especially methoxy, for R8, R9 and R10. 3,4-dimethoxyphenyl and 3,5-dimethoxyphenyl are most preferable.

The compounds having the formulae (B), (C), (D) and (E) are preferable. All the substitutes of these formulae are defined before.

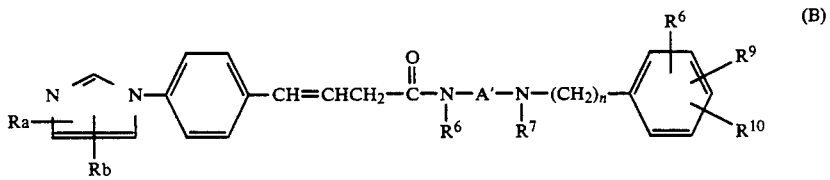 (B)

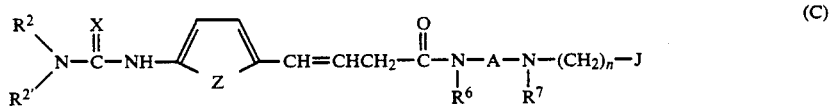 (C)

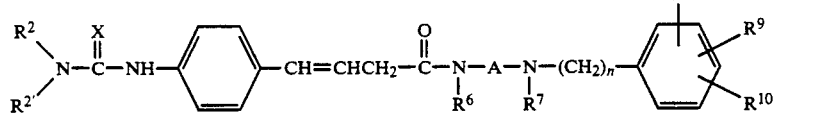 (D)

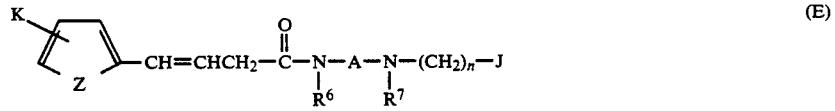 (E)

In the formula (C), R2 and R2' are preferably hydrogen or a lower alkyl such as methyl. X is preferably sulfur and =N—R3, R3 being defined before. R3 is preferably cyano. Z is preferably vinyl. A is preferably an alkylene having 3 or 4 carbon atoms. m is preferably 2. J is preferably R8, R9 and R10 having phenyl, such as 3,4-dimethoxy and 3,5-dimethoxy.

The compound (D) is a preferable one of (C).

In the formula (E), K is pyridyl such as 3-pyridyl and 4-pyridyl, N-oxy-4-pyridyl, 1,4-dihydro-4-oxo-1-pyridyl, 1,4-dihydro-4-oxo-2-pyridyl or 1,4-dihydro-4-oxo-3-pyridyl, optionally having a lower alkyl. Z is preferably vinyl and sulfur. A is preferably an alkylene having 3 or 4 carbon atoms, J is a R8, R9 and R10 having phenyl. K is preferably 1,4-dihydro-4-oxo-1-pyridyl, N-oxy-4-pyridyl and pyridyl. Preferable examples of K are shown below.

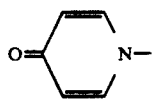

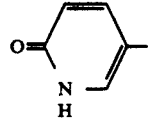

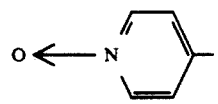

J is preferably 3,4-dimethoxyphenyl or 3,5-dimethoxyphenyl.

The most preferable compound has the following formula (F). A″ is an alkylene having 3 to 6 carbon atoms. Excluded from the formula are cases where A″ is n-C3H6, R6 is hydrogen, R7 is methyl, n is 2 and the R8, R9 and R10 having phenyl is 3,4-dimethoxyphenyl. However, preferable is a case where A″ is an alkylene having 3 or 4 carbon atoms, n is 2 and the phenyl is 3,5-dimethoxy or 3,4-dimethoxy.

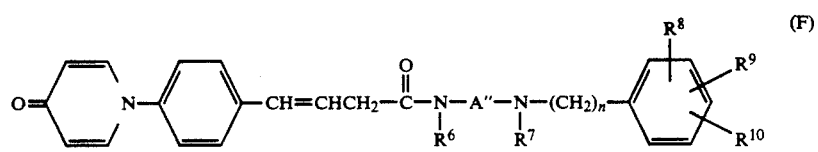

(F)

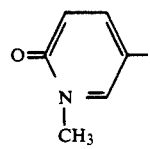

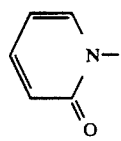

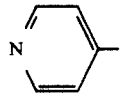

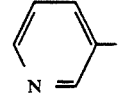

In the formula (I′), it is preferred that R1 is R2R2′N—CX—NH— and A is an alkyl having 3 or 4 carbon atoms. For other preferably embodiments, R1 is

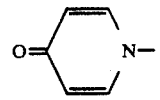

and A is an alkyl having 4 carbon atoms. R1 is imidazolyl and A is an alkyl having 4 carbon atoms. R1 is imidazolyl, A is an alkyl having 4 carbon atoms and J is 3,4-dimethoxyphenyl or 3,5-dimethoxyphenyl. J is 3,4-dimethoxyphenyl or 3,5-dimethoxyphenyl. R1 is

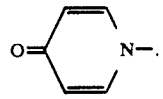

The following compounds are preferred.

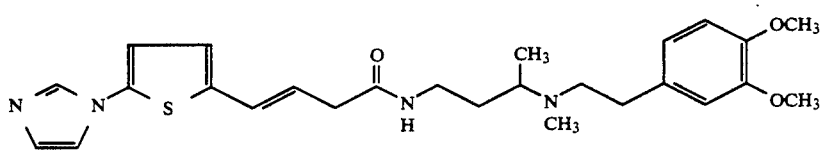

(1)

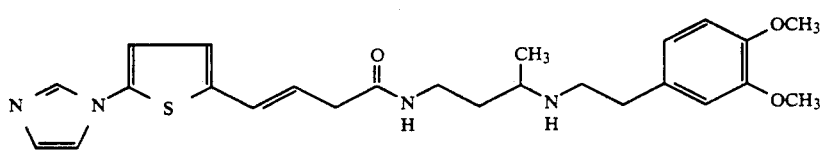

(2)

-continued
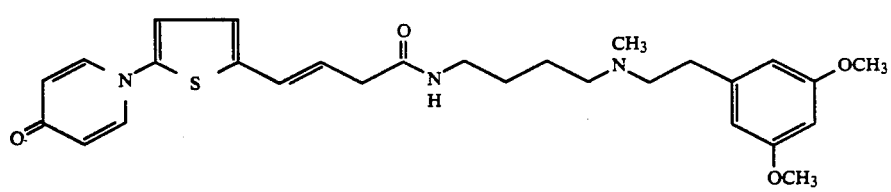(3)
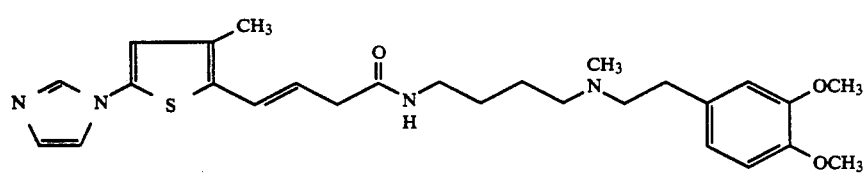(8)
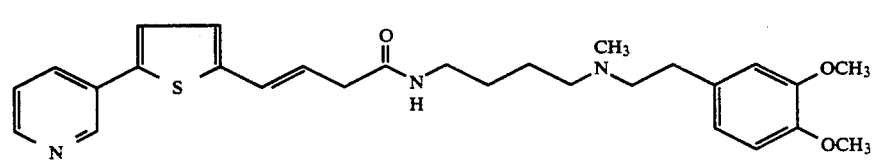(9)
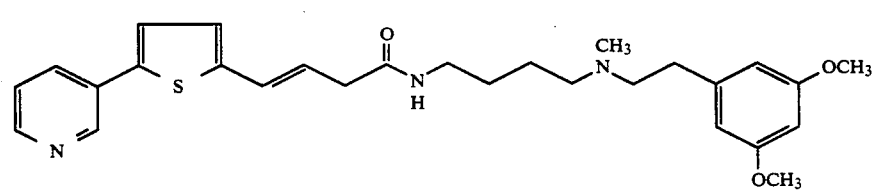(10)
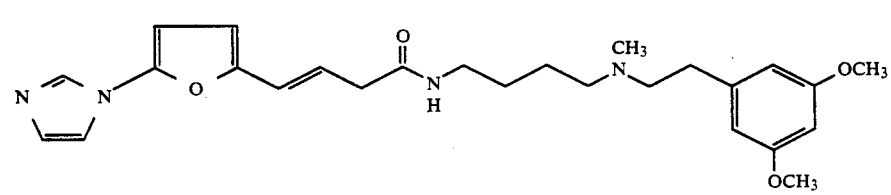(4)
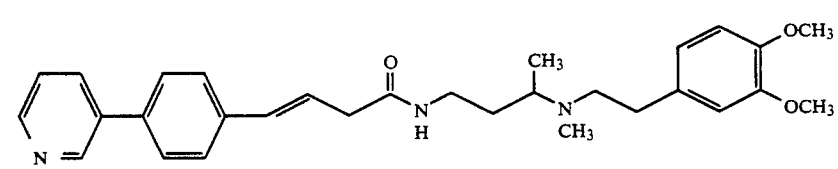(11)
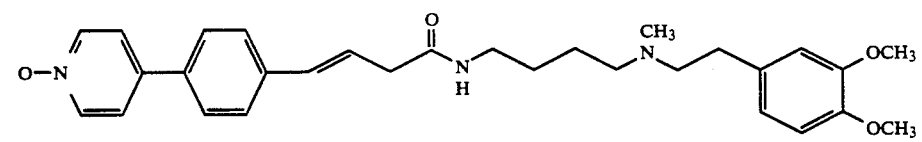(5)
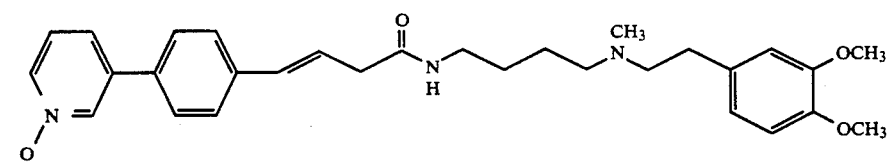(18)
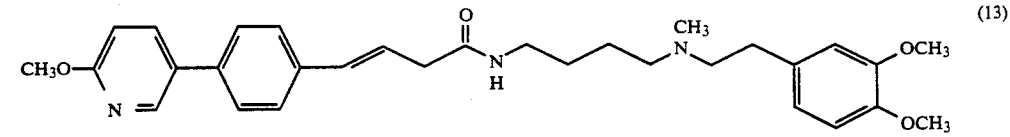(13)

-continued

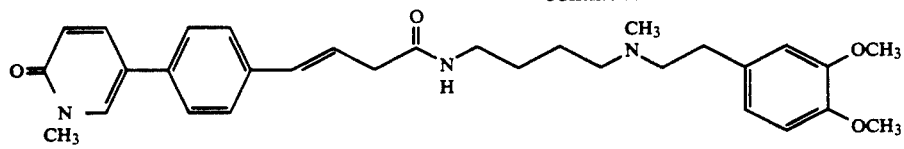

(14)

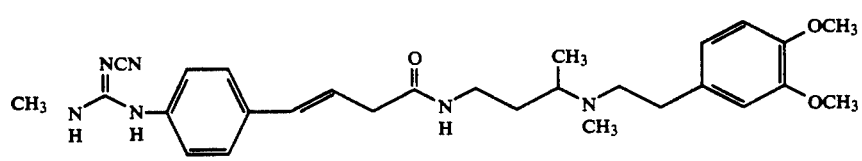

(6)

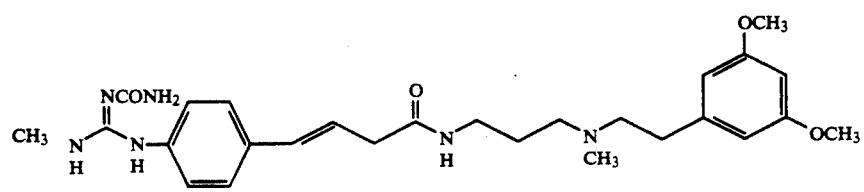

(7)

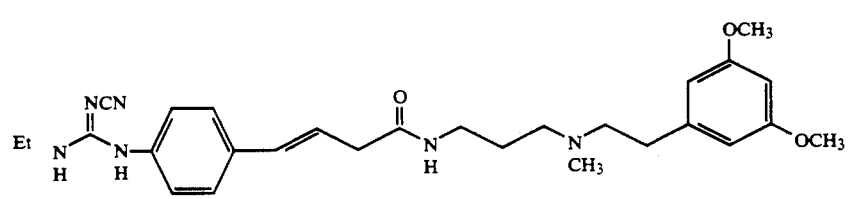

(15)

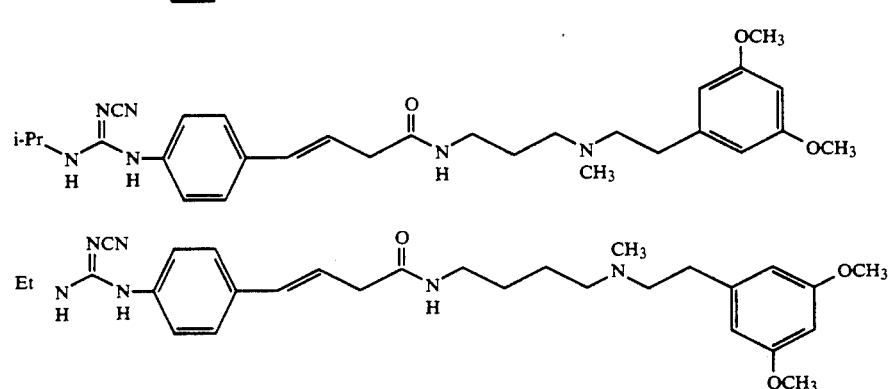

(16)

(17)

(18)

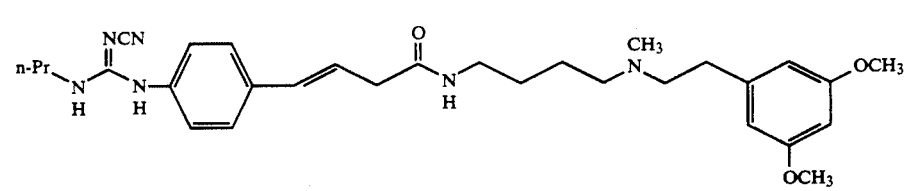

(19)

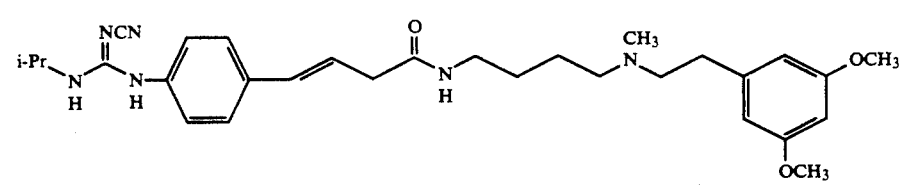

(1) (E)-N-[3-((N'-(2-(3,4-Dimethoxyphenyl)ethyl)-N'-methyl)amino)propyl]-4-(4-(N³-methyl-N²-cyanoguadino)phenyl)-3-butenamide
(2) (E)-N-[3-((N'-(2-(3,5-Dimethoxyphenyl)ethyl)-N'-methyl)amino)propyl]-4-(4-(N³-methyl-N²-cyanoguadino)phenyl)-3-butenamide
(3) (E)-N-[4-((N'-(2-(3,5-Dimethoxyphenyl)ethyl)-N'-methyl)amino)butyl]-4-(4-(1,4,-dihydro-4-oxo-1-pyridyl)phenyl)-3-butenamide
(4) (E)-N-[4-((N'-(2-(3,5-Dimethoxyphenyl)ethyl)-N'-methyl)amino)butyl]-4-(4-(1H-imidazol-1-yl)phenyl)-3-butenamide
(6) (E)-N-[4-((N'-(2-(3,5-Dimethoxyphenyl)ethyl)-N'-methyl)amino)butyl]-4-(4-nitro-1H-imidazol-1-yl)phenyl)-3-butenamide
(7) (E)-N-[4-((N'-(2-(3,5-Dimethoxyphenyl)ethyl)-N'-methyl)amino)butyl]-4-(2-(1H-imidazol-1-yl)thiophen-5-yl)-3-butenamide (8) (E)-N-[3-((N'-(2-(3,5-Dimethoxyphenyl)ethyl)-N'-methyl)amino)propyl]-4-(4-(1,4-dihydro-4-oxo-1-pyridyl)phenyl)-3-butenamide (9) (E)-N-[3-((N'-(2-(3,5-Dimethoxyphenyl)ethyl)-N'-methyl)amino)propyl]-4-(4-($N^2$-methylthioureido)-phenyl)-3-butenamide

(10) (E)-N-[4-((N'-(2-(3,4-Dimethoxyphenyl)ethyl)-N'-methyl)amino)butyl]-4-(4-(1H-imidazol-1-yl)phenyl)-3-butenamide

(11) (E)-N-[4-((N'-(2-(3,4-Dimethoxyphenyl)ethyl)-N'-methyl)amino)butyl]-4-(4-(1,4-dihydro-4-oxo-1-pyridyl)phenyl)-3-butenamide

(12) (E)-N-[4-((N'-(2-(3,4-Dimethoxyphenyl)ethyl)-N'-methyl)amino)butyl]-4-(4-($N^3$-methyl-$N^2$-cyanoguanidino)phenyl)-3-butenamide

(13) (E)-N-[4-((N'-(2-(3,5-Dimethoxyphenyl)ethyl)-N'-methyl)amino)butyl]-4-(4-($N^3$-methyl-$N^2$-cyanoguanidino)phenyl)-3-butenamide

(16) (E)-N-[3-((N'-(2-(3,4-Dimethoxyphenyl)ethyl)-N'-methyl)amino)butyl]-4-(4-(1,4-dihydro-4-oxo-1-pyridyl)phenyl)-3-butenamide

(22) (E)-N-[4-((N'-(2-(4-Methoxyphenyl)ethyl)-N'-methyl)amino)butyl]-4-(4-(1H-imidazol-1-yl)phenyl)-3-butenamide

(23) (E)-N-[4-((N'-(2-(4-Methoxyphenyl)ethyl)-N'-methyl)amino)butyl]-4-(4-(1H-imidazol-1-yl)phenyl)-3-butenamide

(27) (E)-N-[4-((N'-(2-(4-Methoxy-3-methylphenyl)ethyl)-N'-methyl)amino)butyl]-4-(4-(1H-imidazol-1-yl)phenyl)-3-butenamide

(28) (E)-N-[3-((N'-(2-(3,4-Dimethoxyphenyl)ethyl)-N'-methyl)amino)propyl]-4-(4-($N^2$-methylureido)-phenyl)3-

(30) (E)-N-[4-((N'-(2-(3,5-Dimethoxyphenyl)ethyl)-N'-methyl)amino)butyl]-4-(4-($N^2$-methylureido)phenyl)-3-butenamide

(31) (E)-N-[3-((N'-(2-(3,5-Dimethoxyphenyl)ethyl)-N'-methyl)amino)propyl]-4-(4-($N^2$-methylthioureido)-phenyl)-3-butenamide

(32) (E)-N-[4-((N'-(2-(3,4-Dimethoxyphenyl)ethyl)-N'-methyl)amino)propyl]-4-(4-((1-methylamino-2-nitroethen-1-yl)amino)phenyl)-3-butenamide

(37) (E)-N-[4-((N'-(2-(4-Methoxyphenyl)ethyl)-N'-methyl)amino)butyl]-4-(4-($N^3$-methyl-$N^2$-cyanoguanidino)phenyl)-3-butenamide

(38) (E)-N-[4-((N'-(2-(3-Methoxyphenyl)ethyl)-N'-methyl) amino)butyl]-4-(4-($N^3$-methyl-$N^2$-cyanoguanino)phenyl)-3-butenamide

(42) (E)-N-[3-((N'-(2-(3,4-Dimethoxyphenyl)ethyl)-N'-methyl)amino)propyl]-4-(4-(1,4-dihydro-4-oxopyrimidin-2-yl)phenyl)-3-butenamide

(43) (E)-N-[4-((N'-(2-(3,5-Dimethoxyphenyl)ethyl)-N'-methyl)amino)butyl]-4-(4-(1,4-dihydro-4-oxopyrimidin-2-yl)phenyl)-3-butenamide

(46) (E)-N-[4-((N'-(2-(3,4-Dimethoxyphenyl)ethyl)-N'-methyl)amino)butyl]-4-(2-(1H-imidazol-2-yl)thiophen-5-yl)-3-butenamide

(47) (E)-N-[4-((N'-(2-(3,4-Dimethoxyphenyl)ethyl)-N'-methyl)amino)butyl]-4-(4-(4-pyridyl)phenyl)-3-butenamide

(48) (E)-N-[4-((N'-(2-(3,4-Dimethoxyphenyl)ethyl)-N'-methyl)amino)butyl]-4-(4-(3-pyridyl)phenyl)-3-butenamide

(49) (E)-N-[4-((N'-(2-(3,5-Dimethoxyphenyl)ethyl)-N'-methyl)amino)butyl]-4-(4-(3-pyridyl)phenyl)-3-butenamide

(50) (E)-N-[4-((N'-(2-(4-Nitrophenyl)ethyl)-N'-methyl)amino)butyl]-4-(4-(1H-imidazol-1-yl)phenyl)-3-butenamide

(51) (E)-N-[4-((N'-(2-(3,4-Dimethoxyphenyl)ethyl)-N'-methyl)amino)propyl]-4-(4-((1-methylimidzolin-4-on-2-yl)amino)phenyl)-3-butenamide

(55) (E)-N-[4-(N'-(2-(3,5-Dimethoxyphenyl)ethyl)-N'-methyl)amino)butyl]-4-(5-(1,4-dihydro-4-oxo-1-pyridyl)thiophen-2-yl]-3-butenamide

(56) (E)-N-[4-(2-(3,5-Dimethoxyphenyl)ethyl)-N'-methyl)amino)butyl]-4-(5-(1H-imidazol-1-yl)furan-2-yl]-3-butenamide

(57) (E)-N-[4-(N'-(2-(3,4-Dimethoxyphenyl)ethyl)-N'-methyl)amino)butyl]-4-[4-(N-oxy-4-pyridyl)phenyl]-3-butenamide

(58) (E)-N-[3-(N'-(2-(3,4-Dimethoxyphenyl)ethyl)-N'-methyl)amino)butyl]-4-(4-($N^3$-methyl-$N^2$-cyanoguanidino)phenyl]-3-butenamide

(61) (E)-N-4-(N'-(2-(3,4-Dimethoxyphenyl)ethyl)-N'-methyl)amino) butyl]-4-(5-(3-pyridyl)thiophen-2-yl]-3-butenamide

(62) (E)-N-[4-(N'-(2-(3,5-Dimethoxyphenyl)ethyl)-N'-methyl)amino) butyl]-4-(5-(3-pyridyl)thiophen-2-yl]-3-butenamide

(65) (E)-N-[4-(N'-(2-(3,4-Dimethoxyphenyl)ethyl)-N'-methyl) amino)butyl]-4-(4-(2-methoxy-5-pyridyl)-phenyl]-3-butenamide

(66) (E)-N-[4-(N'-(2-(3,4-Dimethoxyphenyl)ethyl)-N'-methyl)amino) butyl]-4-[4-(1,2-dihydro-1-methyl-2-oxo-5-pyridyl)phenyl]-3-butenamide

(67) (E)-N-[3-(N'-(2-(3,5-Dimethoxyphenyl)ethyl)-N'-methyl)amino) propyl]-4-(4-($N^3$-ethyl-$N^2$-cyanoguanidino)phenyl]-3-butenamide

(68) (E)-N-[3-(N'-(2-(3,5-Dimethoxyphenyl)ethyl)-N'-methyl)amino) propyl]-4-(4-($N^3$-i-propyl-$N^2$-cyanoguanidino)phenyl]-3-butenamide

(69) (E)-N-[4-(N'-(2-(3,5-Dimethoxyphenyl)ethyl)-N'-methyl)amino) butyl]-4-(4-($N^3$-ethyl-$N^2$-cyanoguanidino)phenyl]-3-butenamide

(70) (E)-[N-(4-(N'-(2-(3,5-Dimethoxyphenyl)ethyl)-N'-methyl)amino)butyl]-4-(4-($N^3$-n-propyl-$N^2$-cyanoguanidino)phenyl]-3-butenamide

(71) (E)-[N-(4-(N'-(2-(3,5-Dimethoxyphenyl)ethyl)-N'-methyl)amino)butyl]-4-(4-($N^3$-i-propyl-$N^2$-cyanoguanidino)phenyl]-3-butenamide The invention provides a pharmacological composition which comprises a pharmacologically effective amount of the compound or salt as defined above and a pharmacologically acceptable carrier. It also provides a method for treating, prefenting, remitting or ameliorating ischemic heart diseases by administering the compound or salt defined above in a pharmacologically effective amount to a human being.

The pharmacologically acceptable salt of the present invention includes inorganic acid salts such as hydrochloride, sulfate, hydrobromide and phosphate and organic acid salts such as formate, acetate, maleate, fumarate, tartrate, methanesulfonate, benzenesulfonate and toluenesulfonate.

Although optical isomers or tautomers are present depending upon the kind of the substituent of the compound according to the present invention, it is a matter of course that they fall within the scope of the present invention.

Representative processes for the preparation of the compound according to the present invention will now be described.

Preparation Process

A butenoic acid derivative represented by the general formula (I) wherein the moiety represented by the formula:

is a phenyl group, i.e., one represented by the following general formula:

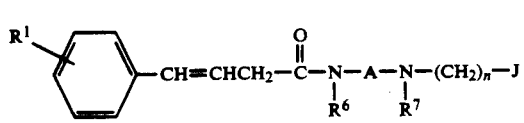

(wherein $R^1$, $R^6$, $R^7$, A, J and n are each as defined above) is prepared according to, for example, the following process:

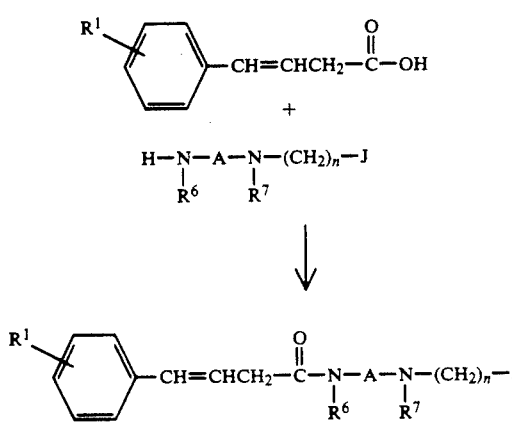

(wherein $R^1$, $R^6$, $R^7$, A, n and J are each as defined above.)

Namely, the objective compound (I') can be prepared by reacting a carboxylic acid represented by the general formula (II) or a reactive derivative thereof with an amino compound represented by the general formula (III) to carry out amidation.

The reactive derivative of the compound (II) includes acid halide thereof such as acid chloride thereof and acid bromide thereof; acid azide; active esters thereof with N-hydroxybenzotriazole or N-hydroxysuccinimide; symmetric acid anhydride thereof and mixed acid anhydride thereof with alkylcarbonic acid or p-toluenesulfonic acid.

When the compound (II) to be used is of free acid type, the above reaction is preferably carried out in the presence of a condensing agent such as dicyclohexylcarbodiimide, 1,1'-carbonyldiimidazole, ethyl chloroformate, diethyl azodicarboxylate or dipyridyl disulfide at a room temperature or under cooling at a temperature of −78° C. or above or by heating under reflux.

The reaction is carried out in water or an organic solvent which is inert to the reaction, for example, methanol, ethanol, pyridine, tetrahydrofuran, dioxane, ether, benzene, toluene, xylene, methylene chloride, dichloroethane, chloroform, dimethylformamide, methylene chloride, ethyl acetate or acetonitrile by using substantially equimolar amounts of a compound (II) or a reactive derivative thereof and a compound (III) or by using a slight excess of either of them.

Depending upon the kind of the reactive derivative, it is sometimes, advantageous for smoothening the progress of the reaction that a base such as diisopropylethylamine, triethylamine, pyridine, picoline, lutidine, N,N-dimethylaniline, 4-dimethylaminopyridine, potassium carbonate or sodium hydroxide is used in the reaction.

Although the reaction temperature is not particularly limited but varies depending upon the kind of the reactive derivative, the reaction is generally carried out at a temperature of from −20° C. to the reflux temperature to obtain the objective compound.

The compound represented by the general formula (II) to be used as a starting material according to the present invention can be prepared by, for example, the following process:

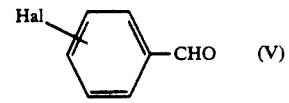

(Step 1) [wherein Hal represents a halogen atom]

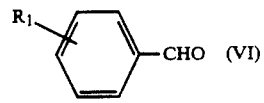

(Step 2) $Ph_3-P^+-(CH_2)_2-\overset{O}{\underset{\|}{C}}-OH$ $Cl^-$ (VI')

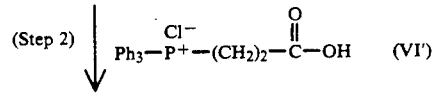

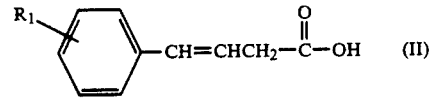

(In the above series of formulas, $R^1$ is as defined above and Ph represents a phenyl group)

Step 1

In this step, a compound represented by the general formula (V) is reacted with a compound represented by the general formula (IV) in the presence of a copper catalyst such as powdered copper or copper oxide according to the Ullmahn reaction to obtain a compound (VI). This reaction may be carried out in the absence of any solvent or in the presence of an organic solvent which is inert to the reaction, for example, nitrobenzene, dimethylformamide or pyridine, or water.

Alternatively, a compound represented by the general formula (VI) can be also prepared by reacting a compound represented by the general formula (V) with a salt of a compound represented by the general formula (IV) with a metal such as lithium, sodium or potassium to carry out the replacement.

This reaction may be carried-out in the absence of any solvent or in the presence of an organic solvent which is inert to the reaction, for example, dimethylformamide, dimethylacetamide, dimethyl sulfoxide, dioxane, ether or tetrahydrofuran.

Step 2

A compound (II) can be prepared by reacting a compound represented by the general formula (VI) with a compound represented by the general formula (VI') in a solvent such as ether, tetrahydrofuran, dioxane, dimethylformamide, dimethylacetamide or dimethyl sulfoxide in the presence of t-butoxypotassium, caustic potash, caustic soda, sodium methoxide, sodium ethoxide or sodium hydride at a temperature of from −78° C. to a room temperature according to an ordinary process.

Alternatively, the compound represented by the above general formula (II) can be also prepared by, for example, the following process:

[when $R^1$ is a group represented by the formula:

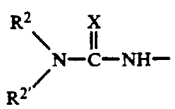

wherein $R^2$ is as defined above, $R^{2'}$ is a hydrogen atom and X is a group represented by the formula: =N—$R^3$ (wherein $R^3$ is as defined above)]

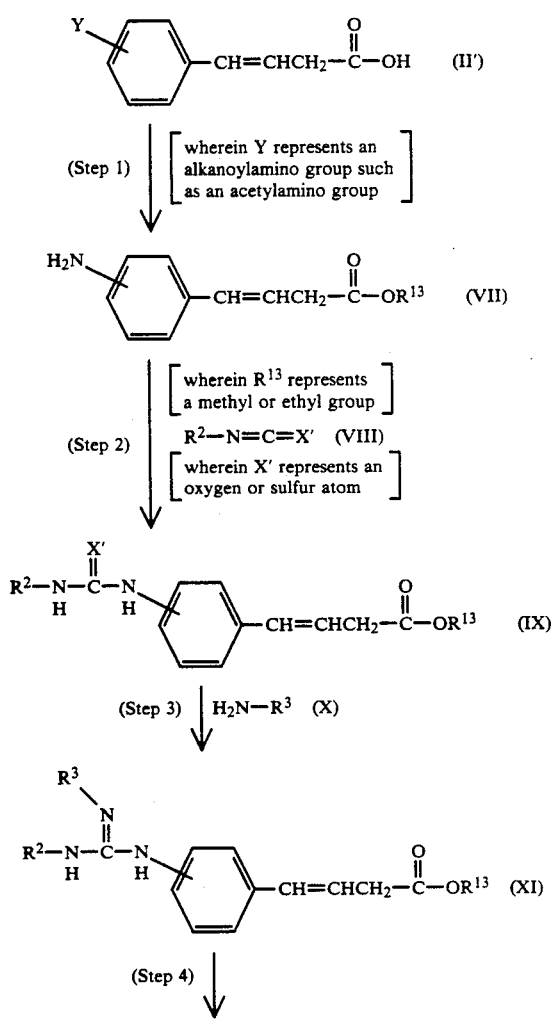

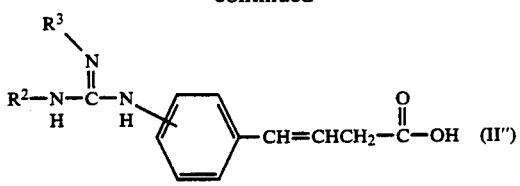

(In the above series of formulas, $R^2$ and $R^3$ are each as defined above)

Step 1

In this step, a compound represented by the general formula (VII) is prepared by hydrolyzing the alkanoylamino group of a compound represented by the general formula (II') under an acidic or basic condition according to a conventional process and esterifying the obtained product according to a conventional process.

This hydrolysis is carried out in a solvent such as water, water-containing methanol, water-containing ethanol, water-containing tetrahydrofuran or water-containing dioxane in the presence of hydrochloric acid, sodium hydroxide, potassium hydroxide or lithium hydroxide at a room temperature or by heating under reflux.

This esterification is carried out in a solvent such as methanol, ethanol or propanol in the presence of hydrogen chloride, concentrated sulfuric acid or p-toluenesulfonic acid at a room temperature or by heating under reflux.

Step 2

In this step, a compound represented by the general formula (VII) is reacted with a compound represented by the general formula (VIII) to obtain a compound represented by the general formula (IX).

This reaction is preferably carried out in the absence of any solvent or in the presence of a solvent inert to the reaction, for example, chloroform, dichloromethane, dichloroethane, tetrahydrofuran, dioxane, benzene, toluene, xylene or dimethylformamide at a room temperature or by heating under reflux.

Step 3

In this step, a compound represented by the general formula (IX) is reacted with a compound represented by the general formula (X) in the presence of a condensing agent such as N,N'-dicyclohexylcarbodiimide to obtain a compound represented by the general formula (XI).

The reaction is preferably carried out in the absence of any solvent or in the presence of an organic solvent inert to the reaction, for example, chloroform, dichloromethane, dichloroethane, ether tetrahydrofuran, dioxane, acetonitrile, benzene, toluene or xylene at a room temperature or by heating under reflux.

Alternatively, a compound represented by the general formula (XI) can be prepared by reacting a compound represented by the general formula (IX) with dimethyl sulfate, trimethyloxonium tetrafluoroborate, triethyloxonium tetrafluoroborate, methyl iodide or ethyl iodide according to a conventional process to obtain an isourea or isothiourea derivative and reacting the isourea or isothiourea derivative with a compound represented by the general formula (X) or a salt thereof with lithium, sodium or potassium.

This reaction is preferably carried out in the absence of any solvent or in the presence of an organic solvent inert to the reaction, for example, chloroform, dichloromethane, dichloroethane, ether, tetrahyrofuran, dioxane, acetonitrile, benzene, toluene or xylene at a room temperature or by heating under reflux.

Step 4

A compound represented by the general formula (XI) is hydrolyzed under an acidic or basic condition according to a conventional process to obtain a compound represented by the general formula (II'').

This hydrolysis is carried out in a solvent such as water, water-containing methanol, water-containing ethanol, water-containing tetrahydrofuran or water-containing dioxane in the presence of hydrochloric acid, sodium hydroxide, potassium hydroxide or lithium hydroxide at a room temperature or by heating under reflux.

When $R^1$ is a group represented by the formula:

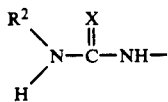

wherein $R^2$ is as defined above and X is an oxygen or sulfur atom (i.e., when $R^{2'}$ is H), as will be described below, a compound represented by the general formula:

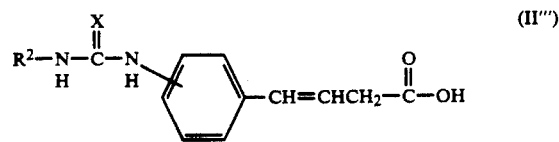

(II''')

can be easily prepared by hydrolyzing a compound represented by the general formula (IX) in a similar manner to that described in the above Step 4.

Alternatively, a compound represented by the general formula (XI) can be prepared by the following process:

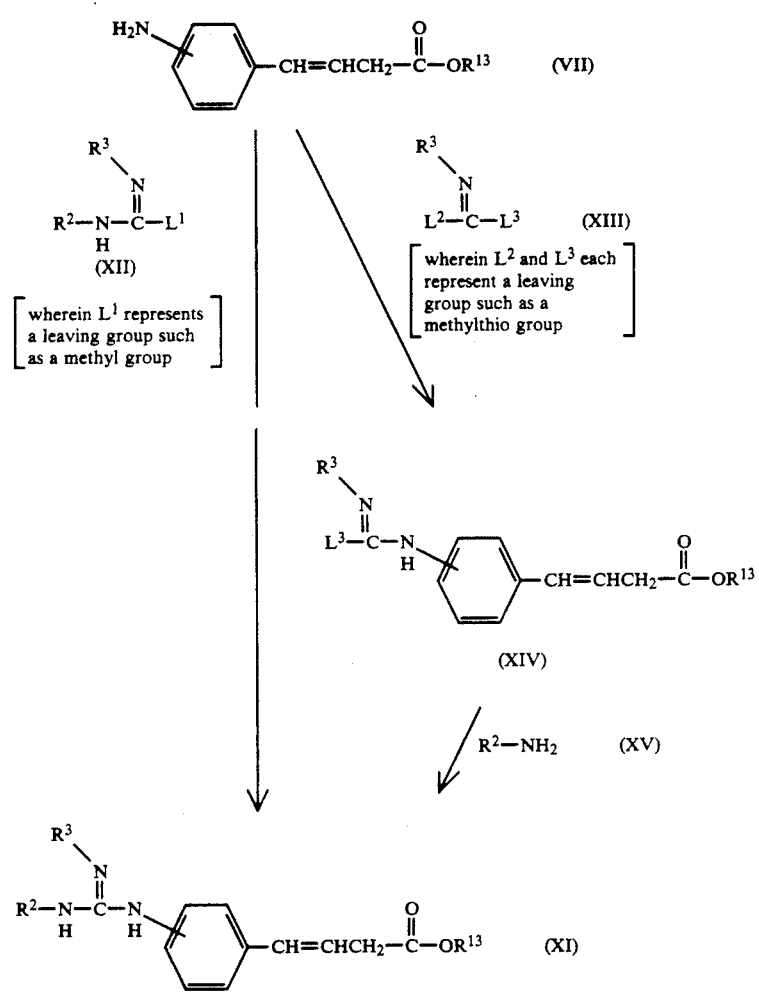

(In the above series of formulas, $R^2$, $R^3$ and $R^{13}$ are each as defined above)

Namely, a compound represented by the general formula (XI) can be prepared by reacting a compound represented by the general formula (VII) with a compound represented by the general formula (XIII) and reacting the obtained product with an amine represented by the general formula (XV) or a salt thereof with lithium, sodium or potassium or by reacting a compound represented by the general formula (VII) with a compound represented by the general formula (XII).

These reactions are each preferably carried out in the absence of any solvent or in the presence of an organic solvent inert to the reaction, for example, chloroform, dichloromethane, dichloroethane, ether, tetrahydrofuran, dioxane, acetonitrile, benzene, toluene or xylene at a room temperature or by heating under reflux.

Further, the compound represented by the general formula (II) can be also prepared by the following processes:

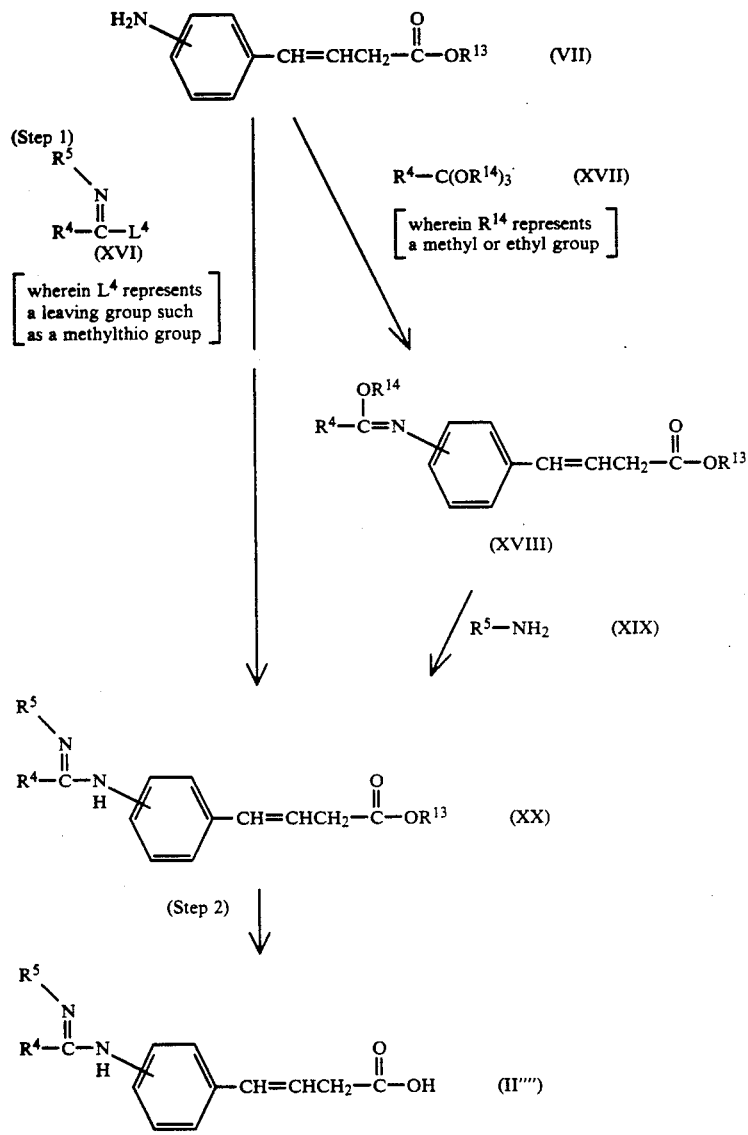

(In the above series of formulas, $R^4$, $R^5$ and $R^{13}$ are each as defined above)

Step 1

A compound represented by the general formula (XX) can be prepared by reacting a compound represented by the general formula (VII) with an ortho ester compound represented by the general formula (XVII) such as methyl orthoformate, ethyl orthoformate, methyl orthoacetate, ethyl orthoacetate, methyl orthopropionate or ethyl orthopropionate and reacting the obtained product with an amine represented by the general formula (XIX) or a salt thereof with lithium, sodium or potassium or by reacting a compound represented by the general formula (VII) with a compound represented by the general formula (XVI).

These reactions are each preferably carried out in the absence of any solvent or in the presence of an organic solvent inert to the reaction, for example, chloroform, dichloromethane, dichloroethane, ether, tetrahydrofuran, dioxane, acetonitrile, benzene, toluene or xylene at a room temperature or by heating under reflux.

Step 2

A compound represented by the general formula (XX) is hydrolyzed under an acidic or basic condition to obtain a compound represented by the general formula (II'''')

This hydrolysis is carried out in a solvent such as water, water-containing methanol, water-containing ethanol, water-containing tetrahydrofuran or water-containing dioxane in the presence of hydrochloric acid, sodium hydroxide, potassium hydroxide or lithium hydroxide at a room temperature or by heating under reflux.

Further, a compound represented by the general formula (IX) wherein X' is a sulfur atom can be also prepared by the following process:

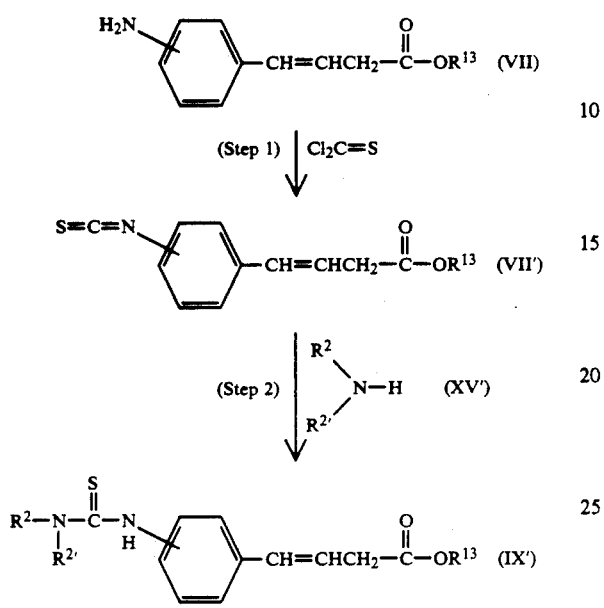

(In the above series of formulas, R², R²' and R¹³ are each as defined above)

Step 1

In this step, a compound represented by the general formula (VII) is reacted with thiophosgene in the presence or absence of a base to obtain a compound represented by the general formula (VII'). The base may be triethylamine, pyridine or 2,6-lutidine.

This reaction is preferably carried out in the absence of any solvent or in the presence of an organic solvent inert to the reaction, for example, chloroform, dichloromethane, dichloroethane, tetrahydrofuran, dioxane, benzene, toluene, xylene or dimethylformamide at ordinary temperatures or under cooling with ice or by heating under reflux.

Step 2

In this step, a compound represented by the general formula (VII') is reacted with a compound represented by the general formula (XV') to obtain a compound represented by the general formula (IX').

This reaction is preferably carried out in the absence of any solvent or in the presence of an organic solvent inert to the reaction, for example, chloroform, dichloromethane, dichloroethane, ether, tetrahydrofuran, dioxane, acetonitrile, benzene, toluene or xylene at ordinary temperatures or under cooling with ice or by heating under reflux.

On the other hand, another starting material, i.e., the compound (III) can be prepared by, for example, the following processes:

Preparation Process 1

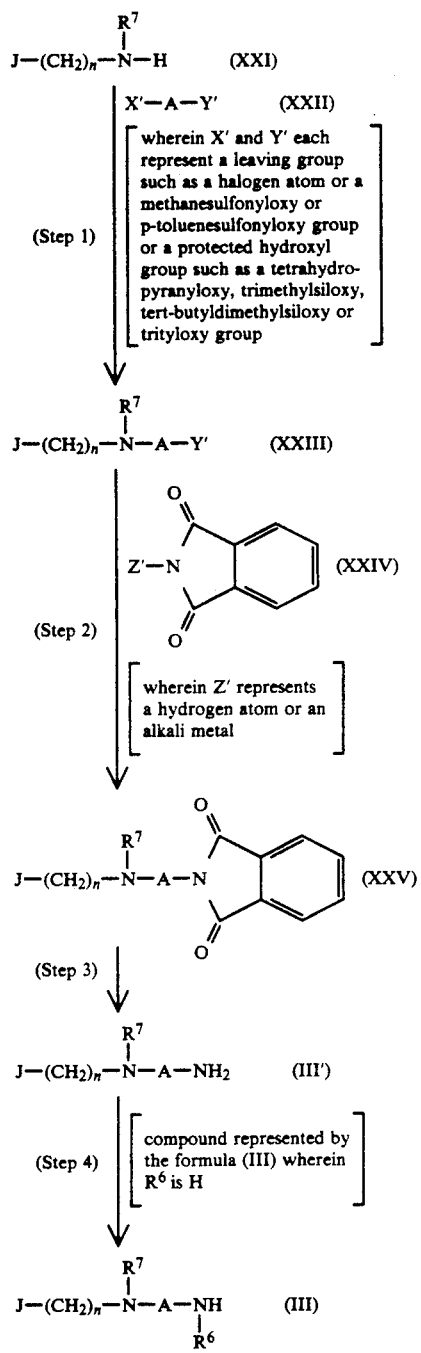

(In the above series of formulas, R⁶, R⁷, n, A and J are each as defined above)

Step 1

In this step, a compound represented by the general formula (XXI) is reacted with a compound represented by the general formula (XXII) according to a conventional process to obtain a compound (XXIII).

More paricularly, the reaction between the both is carried out in a solvent such as benzene, toluene, xylene, dimethylformamide, acetonitrile, dimethyl sulfoxide, dioxane or tetrahydrofuran in the presence of a base such as potassium carbonate, sodium carbonate, triethylamine or diisopropylethylamine under heating to obtain a compound (XXIII).

Step 2

A compound represented by the general formula (XXIII) wherein Y' is a leaving group such as a halogen atom or a methanesulfonyloxy group is converted into a compound (XXV) by the reaction thereof with an alkali metal salt of phthalimide (XXIV) such as potassium or sodium salt thereof in the presence of a base such as potassium carbonate or sodium carbonate. On the other hand, a compound represented by the general formula (XXIII) wherein Y' is a protected hydroxyl group such as a trityloxy or tert-butyldimethylsiloxy group is converted into a compound (XXV) by removing the protective group from the compound according to a conventional process and subjecting the obtained product to the reaction with phthalimide, triphenylphosphine and diethyl azodicarboxylate. In this reaction, a solvent which is inert to the reaction is used and examples thereof include dimethyl sulfoxide, dimethylacetamide, dimethylacetamide, acetonitrile and tetrahydrofuran.

Step 3

A compound (III') (corresponding to the compound represented by the formula (III) wherein $R^6$ is H) can be prepared by heating a compound represented by the general formula (XXV) together with, for example, hydrazine monohydrate under reflux in the presence of an organic solvent such as methanol or ethanol.

Step 4

A compound represented by the general formula (III) can be prepared by reacting a compound represented by the general formula (III') (corresponding to a compound represented by the general formula (III) wherein $R^6$ is H) with an aldehyde or ketone in the presence of a catalyst such as palladium/carbon, platinum oxide or Raney nickel in-an atmosphere of hydrogen to carry out reductive amination.

The aldehyde or ketone to be used in this step may be acetone, cyclobutanone, cyclopentanone or benzaldehyde. Further, a solvent such as methanol, ethanol, benzene, toluene, xylene, dimethylformamide, tetrahydrofuran, dioxane or ethyl acetate may be used in this step.

Alternatively, a compound represented by the general formula (III) can be prepared by conveting a compound represented by the general formula (III') into an acid amide or carbamate, such as N-formyl, N-acetyl, N-methoxycarbonyl or N-ethoxycarbonyl derivative according to a conventional process and reducing the obtained acid amide or carbamate with a metal hydride complex such as lithium aluminum hydride or borane.

This reduction is carried out in a solvent such as ether, tetrahydrofuran, dioxane, 1,2-dimethoxyethane or diethylene glycol dimethyl ether at a room temperature or by heating under refulux.

Alternatively, the compound (XXV) can be prepared by the following process:

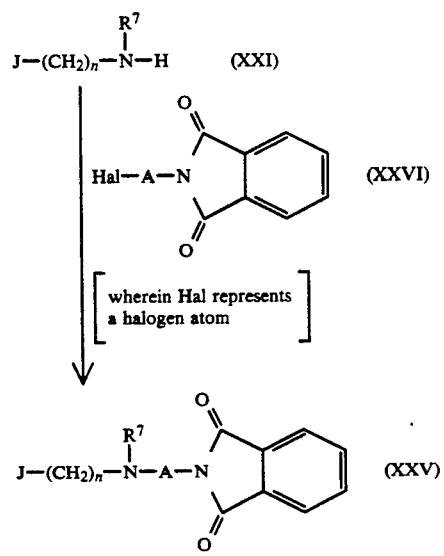

(In the above series of formulas, $R^7$, n, A and J are each as defined above)

Namely, a compound (XXV) can be prepared by reacting a compound represented by the general formula (XXI) with a compound (XXVI) in the presence of a base such as potassium carbonate, sodium carbonate, triethylamine or diisopropylethylamine at a room temperature or by heating under reflux.

In this reaction, a solvent such as dimethyl sulfoxide, dimethylformamide, dimethylacetamide or acetonitrile may be used.

Preparation Process 2

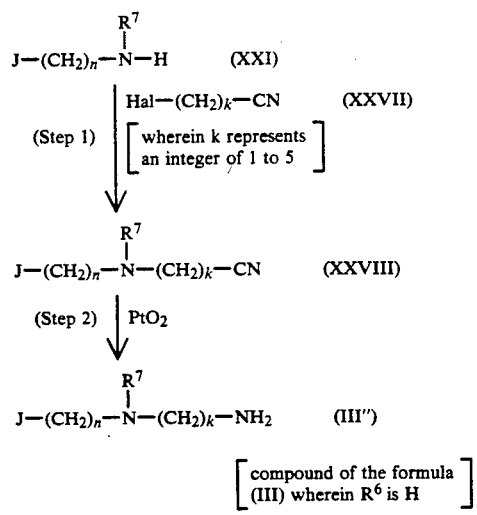

(In the above series of formulas, $R^7$, n and J are each as defined above)

Step 1

A compound represented by the general formula (XXI) is reacted with a compound represented by the general formula (XXVII) in the absence of any solvent or in the presence of a solvent such as dichloromethane, chloroform, acetonitrile, dimethylformamide, dimethyl sulfoxide, ether, tetrahydrofuran, methanol or ethanol by heating under reflux to obtain a compound (XXVIII).

Step 2

A compound represented by the general formula (XXVIII) is hydrogenated in the presence of a catalyst such as palladium/carbon, platinum oxide or Raney nickel to obtain a compound represented by the formula (III'').

This hydrogenation is carried out in a solvent such as methanol, ethanol, dimethylformamide or ethyl acetate under a normal or elevated pressure at an ordinary or higher temperature.

Preparation Process 3

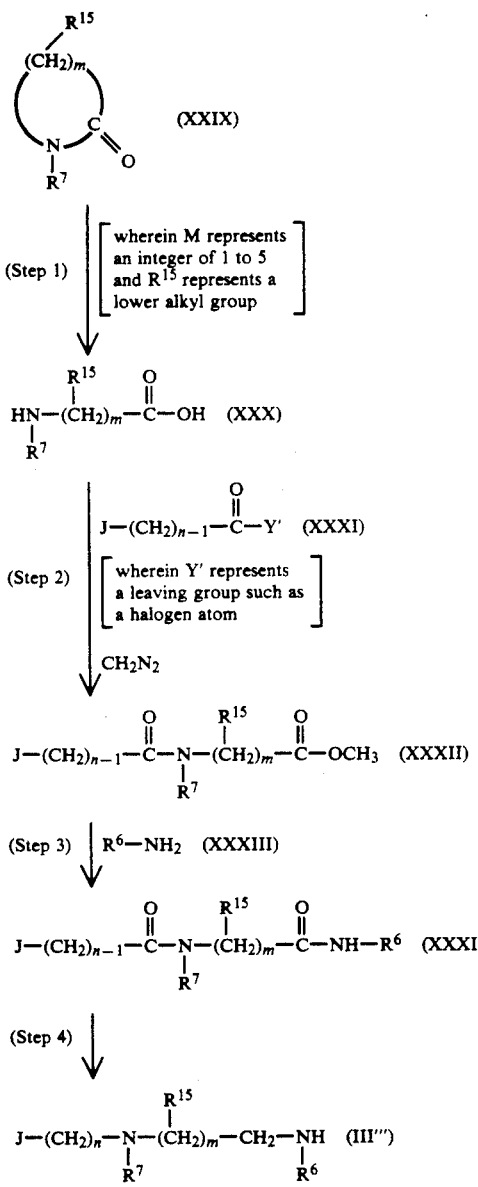

(In the above series of formulas, $R^6$, $R^7$, n and J are each as defined above)

Step 1

A lactam represented by the general formula (XXIX) is hydrolyzed under an acidic or basic condition according to a conventional process to obtain a compound represented by the general formula (XXX).

This hydrolysis is carried out in a solvent such as water, water-containing methanol, water-containing ethanol, water-containing tetrahydrofuran or water-containing dioxane in the presence of hydrochloric acid, sodium hydroxide, potassium hydroxide or lithium hydroxide at a room temperature or by heating under reflux.

Step 2

A compound represented by the general formula (XXXII) can be prepared by reacting a compound represented by the general formula (XXX) with a compound represented by the general formula (XXXI) to carry out the acylation and methylating the obtained product with diazomethane.

This acylation is carried out in an organic solvent such as dichloromethane, choloroform, acetonitrile, dimethylformamide, ether, tetrahydrofuran, dioxane, benzene, toluene or xylene in the presence of a base such as triethylamine, pyridine, potassium carbonate or sodium carbonate at an ordinary temperatures or under cooling with ice or by heating under reflux.

Step 3

A compound represented by the general formula (XXXIV) can be prepared by reacting a compound represented by the general formula (XXXII) with a compound represented by the general formula (XXXIII) to carry out amidation.

This reaction is carried out in the absence of any solvent or in the presence of an organic solvent inert to the reaction, for example, methanol, ethanol, dichloromethane, chloroform, tetrahydrofuran, ether, dioxane, benzene, toluene, xylene or dimethyl sulfoxide at a room temperature or by heating under reflux.

Step 4

A compound represented by the general formula (XXXIV) is reduced with a metal hydride such as lithium aluminum hydride or borane to obtain a compound represented by the general formula (III''''). This reduction is carried out in an organic solvent such as tetrahydrofuran, ether, dioxane, 1,2-dimethoxyethane or diethylene glycol dimethyl ether at a room temperature or by heating under reflux.

Objective compounds of the present invention other than those represented by the following general formula:

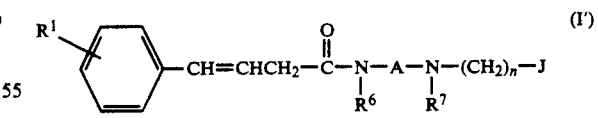

(wherein $R^1$, $R^6$, $R^7$, n, A and J are each as defined above), i.e., compounds represented by the general formula (I') wherein the moiety represented by the formula:

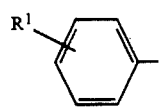

is replaced by the group represented by the formula:

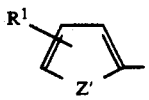

wherein Z' represents an oxygen or sulfur atom or an azomethyne group) can be prepared by the same processes as those described above.

Production Process 4

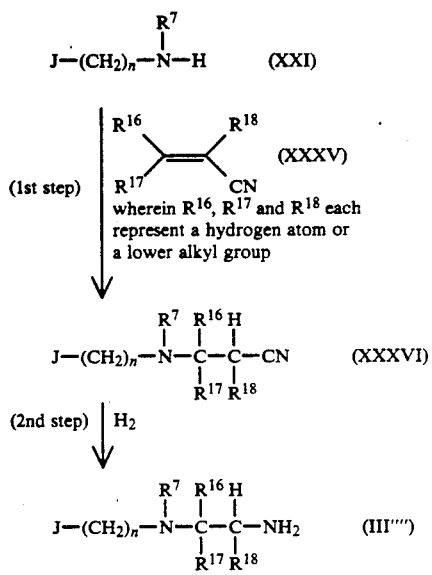

($R^6$ in the formula (III) represents H).

In the above formulae, $R^7$, n and J are as defined above.

1st Step

A compound (XXXVI) can be obtained by reacting a compound of formula (XXI) with a compound of formula (XXXV) without using any solvent or in a solvent such as dichloromethane, chloroform, acetonitrile, N,N-dimethylformamide, dimethyl sulfoxide, tetrahydrofuran, 1,4-dioxane, methanol or ethanol at room temperature or by heating under reflux.

2nd Step

A compound of formula (III'') can be obtained by hydrogenating a compound of formula (XXXVI) in the presence of a catalyst such as palladium-carbon, platinum oxide or Raney nickel.

The reaction solvents usable in this step include metahnol, ethanol, etc. The reaction is conducted at ambient or elevated temperature under atmospheric or elevated pressure.

Pharmacological Test Examples will now be described in order to describe the effect of the compound according to the present invention in detail.

Pharmacological Test Examples

Coronary Blood Flow Increasing Effect on Anesthetized Thracotomized Dog

Mongrel dogs were thoracotomized under the inhalation anesthesia of enflurane. In the measurement of coronary blood flow an electromagnetic flow probe was applied to the left circumflex coronary artery of the dog.

The test compounds at a dose of 0.03 mg/kg were administered intraveneously via a catheter inserted into the femoral vein.

The effect of increasing the coronary blood flow was evaluated by the ratio of change in the blood flow (based on that before the administration) and is shown by a symbol (+) according to the criteria which will be described.

The results are given in Table 1.

TABLE 1

| Coronary blood flow increasing effect on anesthetized thoracotomized dog | |
|---|---|
| Test compound | Cornary blood flow (CBF) |
| Compound A | ++ |
| Compound B | ++ |
| Compound C | +++ |
| Compound D | ++++ |
| Compound E | ++ |
| Compound F | + |
| Compound G | ++++ |
| Compound H | + |
| Compound I | + |
| J | + |
| K | + |
| L | +++ |
| M | +++ |
| N | ++ |
| O | ++ |
| P | + |
| Q | ++ |

Test compounds K, O, P and Q were administered at a dose of 0.01 mg/kg.
Note) The symbols "+", "++", "+++" and "++++" in the above Table represent the rates of increase in coronary blood flow given in the Table 2, respectively.

TABLE 2

| Rate of increase in CBF | |
|---|---|
| + | 1~100% |
| ++ | 101~200% |
| +++ | 201~300% |
| ++++ | >300% |

The test compounds A to Q used in the above Test Examples are as follows:

Compound A (Compound of Example 4): (E)-[N-(4-((N'-(2-(3,5-Dimethoxyphenyl)ethyl)-N'-methyl)amino)butyl]-4-(4-(1H-imidazol-1-yl)-phenyl)-3-butenamide Compound B (Compound of Example 3): (E)-[N-(4-((N'-(2-(3,5-Dimethoxyphenyl)ethyl)-N'-methyl)amino)butyl]-4-(4-(1,4-dihydro-4-oxo-1-pyridyl)-phenyl)-3-butenamide Compound C (Compound of Example 1): (E)-[N-(3-((N'-(2-(3,4-Dimethoxyphenyl)ethyl)-N'-methyl)amino)propyl]-4-(4-($N^3$-methyl-$N^2$-cyanoguanidino)phenyl)-3-butenamide Compound D (Compound of Example 2): (E)-[N-(3-((N'-(2-(3,5-Dimethoxyphenyl)ethyl)-N'-methyl)amino)propyl]- 4-(4-($N^3$-methyl-$N^2$-cyanoguanidino)phenyl)-3-butenamide Compound E (Compound of Example 20): (E)-[N-(4-((N'-(2-(3,4-Dimethoxyphenyl)ethyl)-N'-methyl)amino)pentyl]-4-(4-(1H-imidazol-1-yl)-phenyl)-3-butenamide Compound F (Compound of Example 17): (E)-[N-(3-((N'-(2-(3,5-Dimethoxyphenyl)ethyl)-N'-metnyl)amino)butyl]-4-(4-(1,4-dihydro-4-oxo-1-pyridyl)-phenyl)-3-butenamide Compound G (Compound of Example 6): (E)-N-[4-((N'-(2-(3,5-Dimethoxyphenyl)ethyl)-N'-methyl)amino)butyl]-4-(4-(4-nitro-1H-imidazol-1-yl)phenyl)-3-butenamide Compound H (Compound of Example 7): (E)-N-[4-((N'-(2-(3,5-Dimethoxyphenyl)ethyl)-N'-methyl)amino)butyl]-4-(2-(1H-imidazol-1-yl)thiophen-5-yl)-3-butenamide Compound I (Example 55): (E)-N-[4-(N'-(2-(3,5-Dimethoxyphenyl)ethyl)-N'-methyl)amino)butyl]-4-(5-(1,4-dihydro-4-oxo-1-pyridyl)thiophen-2-yl]-3-butenamide Compound J (Example 61): (E)-N-[4-(N'-(2-(3,4-Dimethoxyphenyl)ethyl)-N'-methyl)amino) butyl]-4-(5-(3-pyridyl)thiophen-2-yl]-3-butenamide Compound K (Example 57): (E)-N-[4-(N'-(2-(3,4-Dimethoxyphenyl)ethyl)-N'-methyl)amino) butyl]-4-[4-(N-oxy-4-pyridyl)phenyl]-3-butenamide Compound L (Example 58): (E)-N-[3-(N'-(2-(3,4-Dimethoxyphenyl)ethyl)-N'-methyl)amino) butyl]-4-(4-($N^3$-methyl-$N^2$-cyanoguanidino)phenyl]-3-butenamide Compound M (Example 67): (E)-N-[3-(N'-(2-(3,5-Dimethoxyphenyl)ethyl)-N'-methyl)amino) propyl]-4-(4-($N^3$-ethyl-$N^2$-cyanoguanidino)phenyl]-3-butenamide Compound N (Example 68): (E)-N-[3-(N'-(2-(3,5-Dimethoxyphenyl)ethyl)-N'-methyl)amino) propyl]-4-(4-($N^3$-i-propyl-$N^2$-cyanoguanidino)phenyl]-3-butenamide Compound O (Example 69): (E)-N-[4-(N'-(2-(3,5-Dimethoxyphenyl)ethyl)-N'-methyl)amino) butyl]-4-(4-($N^3$-ethyl-$N^2$-cyanoguanidino)phenyl]-3-butenamide Compound P (Example 70): (E)-N-[4-(N'-(2-(3,5-Dimethoxyphenyl)ethyl)-N'-methyl)amino) butyl]-4-(4-($N^3$-n-propyl-$N^2$-cyanoguanidino)phenyl]-3-butenamide Compound Q (Example 71): (E)-N-[4-(N'-(2-(3,5-Dimethoxyphenyl)ethyl)-N'-methyl)amino) butyl]-4-(4-($N^3$-i-propyl-$N^2$-cyanoguanidino)phenyl]-3-butenamide It can be understood from the results of the abovedescribed Pharmacological Test Examples that the compounds of the present invention each exhibit an excellent coronary vasodilating effect.

Accordingly, the compound of the present invention is effective in the therapy, prophylaxis, remission and amelioration of ischemic heart diseases such as coronary arteriosclerosis, various angina pectorises and myocardial infraction.

When the compound of the present invention is to be used as a drug, it is administered orally or parenterally. Although the dose of the compound is not particularly limited but varies depending upon the degree of symptom, the age, sexuality, weight or sensitivity of a patient, the method, timing or interval of administration, the properties, prescription or kind of pharmaceutical preparation or the kind of an active ingredient, it is about 1 to 1000 mg, preferably about 5 to 500 mg, still preferably about 20 to 100 mg, per adult a day, which may be administered generally at once or in 2 to 4 portions.

A solid medicine for oral administration containing the compound of the present invention as a principal agent is prepared by adding a filler and, if necessary, a binder, disintegrator, lubricant, coloring agent or corrigent to the compound and shaping the mixture into a tablet, coated tablet, granule, powder or capsule.

Examples of the filler include lactose, corn starch, sucrose, glucose, sorbitol, crystalline cellulose and silicon dioxide and those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricant include magnesium stearate, talc, polyethylene glycol, silica and hardened vegetable oils. The coloring agent may be any one which is permitted for use in drugs. Examples of the corrigent include powdered cocoa, mentha herb, aromatic powder, mentha oil, borneol and powdered cinnamon bark. Of course, the tablet or granule may be suitably coated with sugar, gelatin or the like.

An injection containing the compound of the present invention as a principal agent is prepared by, if necessary, mixing the compound with a pH regulator, buffer agent, suspending agent, solubilizing agent, stabilizer, tonicity agent and/or preservative and converting the mixture into an intravenous, subcutaneous or intramuscular injection according to a conventional method. If necessary, the injection may be freeze-dried by a conventional process.

Examples of the suspending agent include methylcellulose, polysorbate 80, hydroxyethylcellulose, acacia, powdered tragacanth, carboxymethylcellulose sodium and polyoxyethylene sorbitan monolaurate.

Examples of the solubilizing agent include polyoxyethylene hardened castor oil, polysorbate 80, nicotinamide, polyoxyethylene sorbitan monolaurate, macrogol and ethyl ester of castor oil fatty acid.

Further, the stabilizer includes sodium sulfite, sodium metasulfite and ether, while the preservative includes methyl p-hydroxybenzoate, ethyl p-hydroxybenzoate, sorbic acid, phenol, cresol and chlorocresol.

EXAMPLE

Examples of the present invention will now be described, though it is a matter of course that the present invention is not limited to them.

Prior to the description of the Examples, processes for the preparation of the starting compounds (raw materials) to be used in the preparation of the compound according to the present invention will first be described.

PREPARATIVE EXAMPLE 1

4-(1,4-Dihydro-4-oxo-1-pyridyl)benzaldehyde

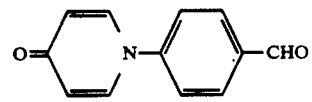

30 g of 4-hydroxypyridine was suspended in 500 ml of N,N-dimethylformamide in a nitrogen atmosphere. The obtained suspension was stirred at a room temperature. 13.25 g of sodium hydride (60% in oil) was added to the suspension in portions to form a sodium salt. After one hour, 36.6 ml of 4-fluorobenzaldehyde was added to the mixture to carry out a reaction at 120° C. for 4 hours. The reaction mixture was cooled by allowing to stand and distilled under a reduced pressure to remove the N,N-dimethylformamide. Ice-water was added to the obtained residue. The insoluble matter thus formed was recovered by filtration and washed with water, acetone and ether successively to obtain 39.04 g of the title compound as a pale yellow powder (yield: 62%).
melting point (°C.): 228 to 230
elemental analysis as $C_{12}H_9NO_2$:

|  | C | H | N |
|---|---|---|---|
| calculated (%) | 72.35 | 4.55 | 7.03 |
| found (%) | 72.58 | 4.64 | 7.04 |

NMR (DMSO-$d_6$) δ; 6.1~6.4 (2H, m), 7.6~7.9 (2H, m), 7.9~8.2 (4H, m), 10.05 (1H, s)

PREPARATIVE EXAMPLE 2

(E)-4-(4-(1,4-Dihydro-4-oxo-1-pyridyl)phenyl)-3-butenoic acid

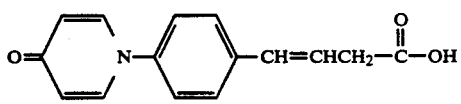

4.0 g of 4-(1,4-dihydro-4-oxo-1-pyridyl)benzaldehyde and 8.2 g of β-carboxyethyltriphenylphosphonium chloride were suspended in 40 ml of tetrahydrofuran in a nitrogen atmosphere. The obtained suspension was cooled to −5° C., followed by the gradual addition of a solution of 4.96 g of potassium tertbutoxide in 30 ml of tetrahydrofuran. The temperature of the mixture was gradually raised to a room temperature. The resulting mixture was stirred for 14 hours, followed by the addition of ice-water. The obtained aqueous phase was washed with chloroform. The pH of the aqueous phase was adjusted with concentrated hydrochloric acid to about 3 to precipitate a crystal. This crystal was recovered by filtration and washed with water and methanol successively to obtain 3.48 g of the title compound as a pale yellow powder (yield: 68%).
melting point (°C.): 275 (dec.)
elemental analysis as $C_{15}H_{13}NO_3$:

|  | C | H | N |
|---|---|---|---|
| calculated (%) | 70.58 | 5.13 | 5.49 |
| found (%) | 70.55 | 5.25 | 5.46 |

NMR (DMSO-$d_6$) δ: 3.21 (2H, d, J=5.6 Hz), 6.1~6.3 (2H, m), 6.36 (1H, dt, J=5.6 Hz, 16.3 Hz), 6.60 (1H, d, J=16.3 Hz), 7.3~7.7 (4H, m), 7.8~8.1 (2H, m)

PREPARATIVE EXAMPLE 3

Methyl (E)-4-(4-aminophenyl)-3-butenoate

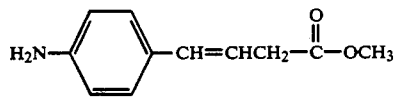

7.5 g of (E)-4-(4-(acetylamino)phenyl)-3-butenoic acid was dissolved in a 1N aqueous solution of potassium hydroxide. The obtained solution was heated under reflux for 4 hours and cooled by allowing to stand. After the pH of the solution had been adjusted to about 3 by the addition of concentrated hydrochloric acid, the resulting solution was concentrated under a reduced pressure, followed by the addition of benzene. The obtained mixture was concentrated and freed from the water by azeotropic distillation to obtain a solid. 300 ml of methanol and 1 ml of concentrated sulfuric acid were added to the solid. The obtained mixture was heated under reflux for 3 hours, cooled by allowing to stand and concentrated under a reduced pressure. An aqueous solution of potassium carbonate was added to the residue and the obtained mixture was extracted with ethyl acetate. The extract was washed with water and a saturated aqueous solution of common salt successively and dried over anhydrous sodium sulfate. The solvent was distilled off and the residue was purified by silica gel column chromatography [solvent: n-hexane/ethyl acetate (2:1)] to obtain 5.38 g of the title compound as a lightly orange-colored oil (yield: 82%).

NMR (CDCl$_3$) δ; 3.20 (2H, d, J=6.2 Hz), 3.6 (2H, br), 3.70 (3H, s), 6.00 (1H, dt, J=6.2 Hz, 1.58 Hz), 6.44 (1H, d, J=15.8 Hz), 6.5~6.7 (2H, m), 7.0~7.2 (2H, m)

PREPARATIVE EXAMPLE 4

Methyl (E)-4-(4-($N^2$-methylthioureido)phenyl)-3-butenoate

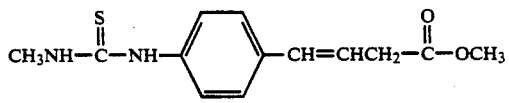

6.00 g of methyl (E)-4-(4-aminophenyl)-3-butenoate was dissolved in 60 ml of dioxane, followed by the addition of 2.75 g of methyl isothiocyanate. The obtained mixture was kept at 100° C. for 5 hours to carry out a reaction. After the removal of the solvent from the reaction mixture, ethyl acetate was added to the residue to carry out crystallization. The insoluble matter thus formed was recovered by filtration to obtain 4.28 g of the title compound as a pale yellow powder. Further, the filtrate was concentrated and purified by silica gel column chromatography [solvent: n-hexane/ethyl acetate (1:1)] to obtain 0.95 g of the title compound (total: 5.23 g) (yield: 63%).
melting point (°C.): 129.5 to 130.5
elemental analysis as $C_{13}H_{16}N_2O_2S$:

|  | C | H | N | S |
|---|---|---|---|---|
| calculated (%) | 59.06 | 6.10 | 10.60 | 12.13 |
| found (%) | 59.26 | 6.15 | 10.54 | 11.99 |

NMR (CDCl$_3$) δ; 3.16 (3H, d, J=4.7 Hz), 3.26 (2H, d, J=5.8 Hz), 3.72 (3H, s), 6.10 (1H, br), 6.24 (1H, dt, J=5.8 Hz, 16.2 Hz), 6.51 (1H, d, J=16.2 Hz), 7.1~7.3 (2H, m), 7.3~7.5 (2H, m), 8.16 (1H, br s)

PREPARATIVE EXAMPLE 5

Methyl (E)-4-(4-($N^3$-methyl-$N^2$-cyanoguanidino)-phenyl)-3-butenoate

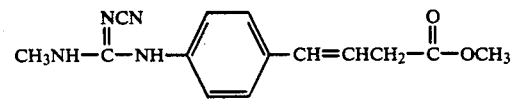

1.90 g of methyl (E)-4-(4-($N^2$-methylthioureido)-phenyl)-3-butenoate was dissolved in 60 ml of dioxane, followed by the addition of 0.45 g of cyanamide, 2.23 g of N,N'-dicyclohexylcarbodiimde and N,N-diisopropylethylamine (in a catalytic amount). The obtained mixture was kept at 100° C. for 3 hours to carry out a reaction. The reaction mixture was cooled by allowing to stand, followed by the addition of ethyl acetate. The mixture was filtered to remove insoluble matter. The obtained filtrate was concentrated, followed by the addition of chloroform. The insoluble matter thus formed was recovered by filtration to obtain the title compound. Further, the filtrate was concentrated and purified by silica gel column chromatogrpahy [solvent: chloroform/methanol (50:1)] to obtain 1.56 g of the title compound as a white powder (yield: 80%).

melting point (°C.): 190.0 to 192.0 elemental analysis as $C_{14}H_{16}N_4O_2$:

|  | C | H | N |
| --- | --- | --- | --- |
| calculated (%) | 61.75 | 5.92 | 20.58 |
| found (%) | 61.89 | 6.06 | 20.49 |

NMR (DMSO-$d_6$) δ; 2.77 (3H, d, J=4.3 Hz), 3.26 (2H, d, J=7.2 Hz), 3.61 (3H, s), 6.25 (1H, dt, J=7.2 Hz, 15.1 Hz), 6.48 (1H, d, J=15.1 Hz), 7.0~7.4 (5H, m), 8.80 (1H, br s)

PREPARATIVE EXAMPLE 6

(E)-4-(4-($N^3$-Methyl-$N^2$-cyanoguanidino)phenyl)-3-butenoic acid

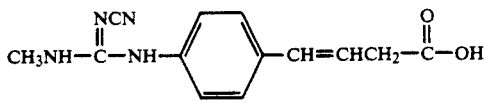

1.56 g of methyl (E)-4-(4-($N^3$-methyl-$N^2$-cyanoguanidino)phenyl)-3-butenoate was dissolved in 15 ml of dioxane, followed by the addition of 6.9 ml of a 1N aqueous solution of sodium hydroxide. The mixture was reacted at a room temperature for 8 hours. The reaction mixture was concentrated, followed by the addition of water. The obtained aqueous phase was washed with chloroform. The pH of the resulting aqueous phase was adjusted to about 3 by the addition of concentrated hydrochloric acid to precipitate a crystal. This crystal was recovered by filtration and washed with water to obtain 0.84 g of the title compound as a pale yellow powder (yield: 57%).

melting point (°C.): 176 (dec.)

elemental analysis as $C_{13}H_{14}N_4O_2$:

|  | C | H | N |
| --- | --- | --- | --- |
| calculated (%) | 60.45 | 5.46 | 21.69 |
| found (%) | 60.51 | 5.56 | 21.67 |

NMR (DMSO-$d_6$) δ; 2.76 (3H, d, J=5.0 Hz), 3.16 (2H, d, J=5.8 Hz), 6.16 (1H, dt, J=5.8 Hz, 15.8 Hz), 6.43 (1H, d, J=15.8 Hz), 6.8~7.4 (5H, m), 8.80 (1H, br s)

PREPARATIVE EXAMPLE 7

Methyl (E)-4-(4-($N^2$-cyanopropanamidino)phenyl)-3-butenoate

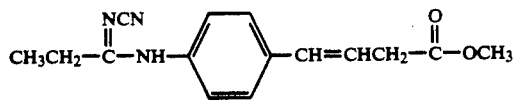

3.38 g of methyl (E)-4-(4-aminophenyl)-3-butenoate and 4.67 g of ethyl orthopropionate were mixed together and kept at 150° to 160° C. for one hour to carry out a reaction. The reaction mixture was cooled by allowing to stand and concentrated under a reduced pressure to obtain a lightly orange-colored oil. 1.49 g of cyanamide was added to the oil to carry out a reaction at 150° to 160° C. for 15 minutes. The reaction mixture was cooled by allowing to stand and purified by silica gel column chromatography [solvent: dichloromethane/methanol (100:1)] to obtain 3.39 g of the title compound as a lightly orange-colored solid (yield: 71%).

melting point (°C.): 110 to 120 elemental analysis as $C_{15}H_{17}N_3O_2$:

|  | C | H | N |
| --- | --- | --- | --- |
| calculated (%) | 66.40 | 6.32 | 15.49 |
| found (%) | 66.72 | 6.34 | 15.56 |

NMR (CDCl$_3$) δ: 1.43 (3H, t, J=7.5 Hz), 2.80 (2H, q, J=7.5 Hz), 3.28 (2H, d, J=5.7 Hz), 3.74 (3H, s), 6.23 (1H, dt, J=5.7 Hz, 15.8 Hz), 6.50 (1H, d, J=15.8 Hz), 7.1~7.4 (2H, m), 7.4~7.7 (2H, m), 8.82 (1H, br s)

PREPARATIVE EXAMPLE 8

(E)-4-(4-($N^2$-Cyanopropanamidino)phenyl)-3-butenoic acid

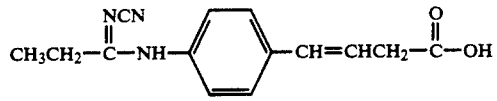

The same procedure as that of Preparative Example 6 was repeated except that methyl (E)-4-(4-($N^2$-cyanopropanamidino)phenyl)-3-butenoate was used to obtain the title compound as a pale yellow powder (yield: 61%).

melting point (°C.): 176 to 178 elemental analysis as $C_{14}H_{15}N_3O_2$:

|  | C | H | N |
| --- | --- | --- | --- |
| calculated (%) | 65.35 | 5.88 | 16.33 |
| found (%) | 65.63 | 5.87 | 16.56 |

NMR (DMSO-$d_6$) δ; 1.31 (3H, t, J=7.9 Hz), 2.67 (2H, q, J=7.9 Hz), 3.18 (2H, d, J=5.7 Hz), 6.23 (1H, dt, J=5.7 Hz, 15.8 Hz), 6.49 (1H, d, J=15.8 Hz), 7.2~7.6 (4H, m), 10.51 (1H, s), 12.29 (1H, br s)

PREPARATIVE EXAMPLE 9

(E)-4-(4-(N²-Methylthioureido)phenyl)-3-butenoic acid

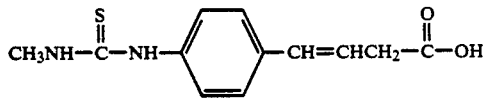

The same procedure as that of Example 6 was repeated except that methyl (E)-4-(4-(N²-methylthioureido)phenyl)-3-butenoate was used. The title compound was obtained as a pale yellow powder (yield: 54%).

melting point (°C.): 150 to 152
elemental analysis as $C_{12}H_{14}N_2O_2S$:

|  | C | H | N | S |
|---|---|---|---|---|
| calculated (%) | 57.78 | 5.64 | 11.19 | 12.81 |
| found (%) | 57.74 | 5.63 | 11.02 | 12.55 |

NMR (DMSO-$d_6$) δ; 2.91 (3H, d, J=4.4 Hz), 3.16 (2H, d, J=6.2 Hz), 6.19 (1H, dt, J=6.2 Hz, 15.8 Hz), 6.41 (1H, d, J=15.8 Hz), 7.34 (4H, s), 7.67 (1H, br d, J≈4 Hz), 9.49 (1H, br s)

PREPARATIVE EXAMPLE 10

Methyl (E)-4-(4-(N²-methylureido)phenyl-3-butenoate

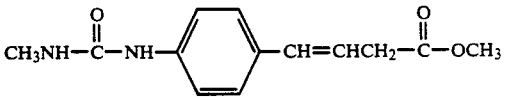

3.00 g of methyl (E)-4-(4-aminophenyl)-3-butenoate was dissolved in 30 ml of 1,4-dioxane, followed by the addition of 1.11 ml of methyl isocyanate. The obtained mixture was heated under reflux for 3 hours and distilled under a reduced pressure to remove the solvent. Ether was added to the residue. The insoluble matter thus formed was recovered by filtration to obtain 0.87 g of the title compound as a pale yellow powder.

The filtrate wsa concentrated and purified by silica gel column chromatography [solvent: dichloromethane/methanol (40:1)] to obtain 0.98 g of the title compound as a yellow solid (total: 1.85 g, yield: 48%).

melting point (°C.): 146 to 148
elemental analysis as $C_{13}H_{16}N_2O_3$:

|  | C | H | N |
|---|---|---|---|
| calculated (%) | 62.89 | 6.50 | 11.28 |
| found (%) | 62.89 | 6.44 | 11.37 |

NMR (CDCl$_3$) δ; 2.73 (3H, d, J=4.8 Hz), 3.22 (2H, d, J=6.2 Hz), 3.70 (3H, s), 5.25~5.54 (1H, m), 6.12 (1H, dt, J=6.2 Hz, 15.8 Hz), 6.42 (1H, d, J=15.8 Hz), 6.86~7.39 (5H, m)

PREPARATIVE EXAMPLE 11

(E)-4-(4-(N²-Methylureido)phenyl-3-butenoic acid

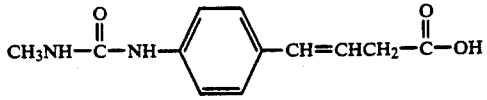

The same procedure as that of Preparative Example 6 was repeated except that methyl (E)-4-(4-(N²-methylureido)phenyl)-3-butenoate was used. The title compound was obtained as a lightly orange-colored powder (yield: 74%).

melting point (°C.): 188.5 to 200.5
elemental analysis as $C_{12}H_{14}N_2O_3$:

|  | C | H | N |
|---|---|---|---|
| calculated (%) | 61.52 | 6.02 | 11.96 |
| found (%) | 61.60 | 6.06 | 11.81 |

NMR (DMSO-$d_6$) δ; 2.63 (3H, d, J=4.4 Hz), 3.14 (2H, d, J=7.2 Hz), 5.95~6.05 (1H, m), 6.12 (1H, dt, J=7.2 Hz, 16.0 Hz), 6.38 (1H, d, J=10.0 Hz), 7.25 (2H, d, J=8.8 Hz), 7.35 (2H, d, J=8.8 Hz), 8.52 (1H, s)

PREPARATIVE EXAMPLE 12

Methyl (E)-4-{4-((1-methylthio-2-nitroethen-1-yl)amino)-phenyl}-3-butenoate

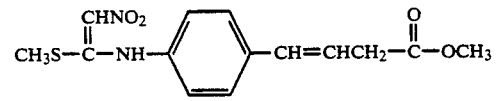

7.00 g of methyl (E)-4-(4-aminophenyl)-3-butenoate was dissolved in 120 ml of n-propanol, followed by the addition of 30.28 g of 1,1-bis(methylthio)-2-nitroethylene. The obtained mixture was heated under reflux for 3 hours and distilled ro remove the solvent. The residue was purified by silica gel column chromatography (solvent: dichloromethane). The obtained solid was washed with ethyl ether to obtain 9.65 g of the title compound as a yellow powder (yield: 86%).

melting point (°C.): 136 to 138.5
elemental analysis as $C_{14}H_{16}N_2O_4S$:

|  | C | H | N | S |
|---|---|---|---|---|
| calculated (%) | 54.53 | 5.23 | 9.09 | 10.40 |
| found (%) | 54.51 | 5.24 | 8.66 | 10.22 |

NMR (CDCl$_3$) δ; 2.38 (3H, s), 3.27 (2H, d, J=5.7 Hz), 3.72 (3H, s), 6.29 (1H, dt, J=5.7 Hz, 15.8 Hz), 6.53 (1H, d, J=15.8 Hz), 6.68 (1H, s), 7.22 (2H, d like, J=8 Hz), 7.41 (2H, d like, J=8 Hz), 11.79 (1H, s)

PREPARATIVE EXAMPLE 13

Methyl (E)-4-{4-((1-methylamino-2-nitroethen-1-yl)amino)-phenyl}-3-butenoate

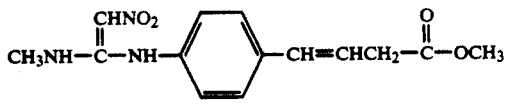

1.00 g of methyl (E)-4-{4-((1-methylthio-2-nitroethen-1-yl)amino)phenyl}-3-butenoate was suspended in 5 ml of methanol, followed by the addition of 1.25 ml of a 40% solution of methylamine in methanol. The obtained mixture was stirred at a room temperature for 4 hours and distilled to remove the solvent. The residue was purified by silica gel column chromatography [solvent: dichloromethane/methanol (30:1)] to obtain 0.5 g of the title compound as a pale yellow solid (yield: 54%).

NMR (CDCl$_3$) δ; 2.91 (3H, br), 3.23 (2H, d, J=5.8 Hz), 3.68 (3H, s), 6.19 (1H, dt, J=5.8 Hz, 16.2 Hz), 6.43 (1H, d, J=16.2 Hz), 6.45 (1H, br s), 6.96~7.20 (3H, m), 7.32 (2H, d, J=7.9 Hz), 11.50 (1H, br)

PREPARATIVE EXAMPLE 14

(E)-4-{4-((1-Methylamino-2-nitroethen-1-yl)amino)-phenyl}-3-butenoic acid

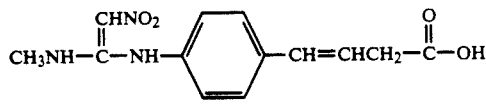

The same procedure as that of Preparative Example 6 was repeated except that methyl (E)-4-{4-((1-methylamino-2-nitroethen-1-yl)amino)phenyl}-3-butenoate was used. The title compound was obtained as a lightly orange-colored powder (yield: 63%).

NMR (DMSO-d$_6$) δ; 2.94 (3H, d, J=4.3 Hz), 3.16 (2H, d, J=5.4 Hz), 6.12 (1H, br s), 6.24 (1H, dt, J=5.4 Hz, 15.5 Hz), 6.48 (1H, d, J=15.5 Hz), 7.12 (2H, d, J=7.9 Hz), 7.41 (2H, d, J=7.9 Hz)

PREPARATIVE EXAMPLE 15

Methyl (E)-4-{4-((1,4-dihydro-4-oxopyrimidin-2-yl)amino)-pheny}-3-butenoate

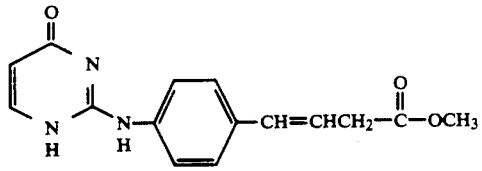

A mixture comprising 3.00 g of methyl (E)-4-(4-aminophenyl)-3-butenoate and 2.34 g of 2-methylthio-1,4-dihydro-4-oxopyrimidine was stirred at 150° to 160° C. for 20 minutes. The reaction mixture was purified by silica gel column chromatography [solvent: dichloromethane/methanol (30:1)] to obtain 1.58 g of the title compound as a light brown powder (yield: 35%).

NMR (CDCl$_3$) δ; 3.12 (2H, d, J=5.4 Hz), 3.65 (3H, s), 5.76 (1H, d, J=7.2 Hz), 6.05 (1H, dt, J=5.4 Hz, 15.5 Hz), 6.31 (1H, d, J=15.5 Hz), 7.08~7.80 (7H, m)

PREPARATIVE EXAMPLE 16

(E)-4-{4-((1,4-Dihydro-4-oxopyrimidin-2-yl)amino)-phenyl}-3-butenoic acid

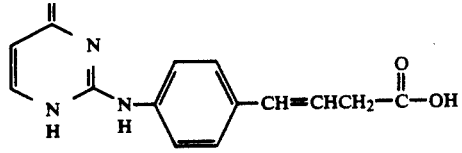

The same procedure as that of Preparative Example 6 was repeated except that methyl (E)-4-{4-((1,4-dihydro-4-oxopyrimidin-2-yl)amino)phenyl}-3-butenoate was used. The title compound was obtained as a lightly organe-colored powder (yield: 58%).

NMR (DMSO-d$_6$) δ; 3.15 (2H, d, J=6.8 Hz), 5.81 (1H, br s), 6.19 (1H, dt, J=6.8 Hz, 15.6 Hz), 6.42 (1H, d, J=15.6 Hz), 7.34 (2H, d, J=8.8 Hz), 7.56 (2H, d, J=8.8 Hz), 7.76 (1H, br s)

PREPARATIVE EXAMPLE 17

Methyl (E)-4-{4-((pyrimidin-2-yl)amino)phenyl}-3-butenoate

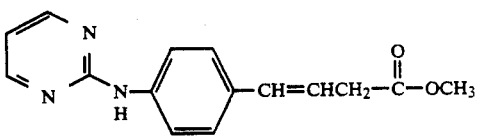

1.5 g of methyl 4-aminobutenoate, 900 mg of 2-chloropyrimidine and 1.0 g of diisopropylethylamine were dissolved in 20 ml of N,N-dimethylformamide to obtain a solution. This solution was heated under reflux for 6 hours, cooled and distilled under a reduced pressure to remove low-boiling matter. The residue was purified by silica gel column chromatography [solvent: ethyl acetate/hexane (1:30)] to obtain 300 mg of the title compound as a white crystal (yield: 14%).

NMR (CDCl$_3$) δ; 3.23 (2H, d, J=7.2 Hz), 3.70 (3H, s), 6.19 (1H, dt, J=16.0 Hz, 4.8 Hz), 6.44 (1H, d, J=16 Hz), 6.69 (1H, t, J=4.8 Hz), 7.33 (2H, d, J=6.8 Hz), 7.57 (2H, d, J=6.8 Hz), 8.05 (1H, s), 8.40 (2H, d, J=4.8 Hz)

PREPARATIVE EXAMPLE 18

(E)-4-{4-((Pyrimidin-2-yl)amino)phenyl}-3-butenoic acid

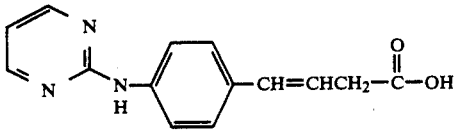

300 mg of methyl (E)-4-{4-((pyrimidin-2-yl)-amino)-phenyl}-3-butenoate was dissolved in 5 ml of dioxane, followed by the addition of 3 ml of a 1N solution of sodium hydroxide. The obtained mixture was stirred at a room temperature for 2 hours, followed by the addition of 3 ml of 1N hydrochloric acid. The crystal thus formed was recovered by filtration and dried under a reduced pressure to obtain 200 mg of the title compound as a white crystal (yield: 70%).

NMR (DMSO-d$_6$) δ; 3.13 (2H, d, J=8 Hz), 6.16 (1H, dt, J=15 Hz, 8 Hz), 6.39 (1H, d, J=15 Hz), 6.82 (1H, t, J=6 Hz), 7.32 (2H, dd, J=8 Hz, 2 Hz), 7.72 (2H, dd, J=8 Hz, 2 Hz), 8.47 (2H, d, J=6 Hz), 9.65 (1H, s)

PREPARATIVE EXAMPLE 19

4-(4-Nitro-1H-imidazol-1-yl)benzaldehyde

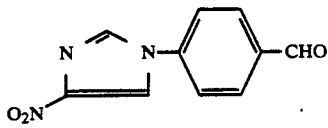

A suspension of 18.6 g of 4-fluorobenzaldehyde and 18.6 g of 4-nitroimidazole in 70 ml of dimethylformamide was dropwise added to a suspension of 6.6 g of sodium hydride (60% suspension in mineral oil) in 150 ml of dimethylformamide at a room temperature under stirring. The obtained mixture was stirred at 90° C. for about 5 hours, cooled and poured into ice-water to precipitate a solid. This solid was recovered by filtration, washed with water and heated together with ethanol. The mixture was cooled and filtered. The obtained solid was washed with ethanol to obtain 18 g of the title compound as a white powder (yield: 55%).

melting point (°C.): 235 to 236
elemental analysis as C$_{10}$H$_7$N$_3$O$_3$:

|  | C | H | N |
|---|---|---|---|
| calculated (%) | 55.30 | 3.25 | 19.35 |
| found (%) | 55.39 | 3.38 | 19.51 |

NMR (DMSO-d$_6$) δ; 7.96~8.10 (4H, m), 8.68 (1H, s), 9.06 (1H, s), 10.0 (1H, s)

PREPARATIVE EXAMPLE 20

(E)-4-((4-Nitro-1H-imidazol-1-yl)phenyl)-3-butenoic acid

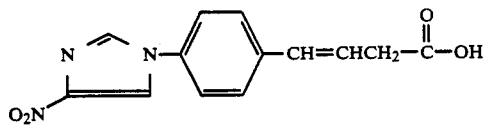

10.9 g of 4-(4-nitro-1H-imidazol-1-yl)benzaldehyde and 20.4 g of β-carboxyethyltriphenylphosphonium chloride were suspended in 200 ml of tetrahydrofuran, followed by cooling to −70° C. 70 ml of a solution of 12.3 g of potassium tert-butoxide in tetrahydrofuran was slowly dropwise added to the above suspension under stirring. After the completion of the addition, the temperature of the obtained mixture was gradually raised to a room temperature. The resulting mixture was poured into water. The obtained mixture was extracted with ethyl acetate. The pH of the obtained aqueous phase was adjusted to about 4 to precipitate a solid. This solid was recovered by filtration and filtration and washed with water and ethanol successively to obtain 2.1 g of the title compound as a light brown powder.

PREPARATIVE EXAMPLE 21

N-Methyl-N-(2-(3,5-dimethoxyphenyl)ethyl)-1,4-diaminobutane

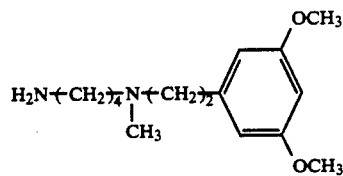

10.0 g of N-methyl-(2-(3,5-dimethoxyphenyl)ethyl)amine was dissolved in 130 ml of N,N-dimethylformamide, followed by the addition of 10.63 g of anhydrous potassium carbonate and 6.12 ml of 4-bromobutyronitrile. The reaction was carried out at a room temperature for 12 hours. Water was added to the reaction mixture. The obtained mixture was extracted with ethyl acetate. The ethyl acetate phase was washed with water and a saturated aqueous solution of common salt successively, dried over anhydrous potassium carbonate and distilled to remove the solvent. 150 ml of ethanol, 11 ml of concentrated hydrochloric acid and 1 g of platinum oxide were added to the obtained residue to carry out hydrogenation at a room temperature under 3 kg/cm$^2$ for 12 hours. The catalyst was filtered out and the filtrate was concentrated under a reduced pressure, followed by the addition of concentrated aqueous ammonia. The obtained mixture was extracted with chloroform. The chloroform phase was dried over anhydrous potassium carbonate. After the solvent had been distilled off, the residue was distilled under a reduced pressure to obtain 10.85 g of the title compound as a colorless oil (yield: 80%).

boiling point (°C.): 165~168 (0.5~0.9 mmHg)
NMR (CDCl$_3$) δ; 1.3~1.9 (6H, m), 2.2~2.8 (11H, m), 3.75 (6H, s), 6.2~6.4 (3H, m)

PREPARATIVE EXAMPLE 22

The following compounds were prepared in a similar manner to that of Preparative Example 21.

N-Methyl-N-(2-phenylethyl)-1,4-diaminobutane

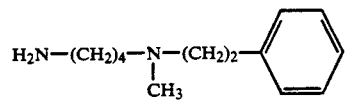

colorless oil
boiling point (°C.): 108~114 (~1 mmHg)
NMR (CDCl$_3$) δ; 1.15 (2H, s), 1.25~1.73 (4H, m), 2.06~2.92 (11H, m), 7.02~7.36 (5H, m)

N-Methyl-N-(2-(4-methoxyphenyl)ethyl)-1,4 diaminobutane

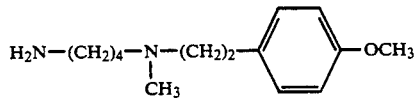

colorless oil
boiling point (°C.): 147~155 (~1 mmHg)

NMR (CDCl₃) δ; 1.27 (2H, s), 1.34~1.68 (4H, m), 2.07~2.85 (11H, m), 3.76 (3H, s), 6.69~6.88 (2H, m), 6.97~7.17 (2H, m)

N-Methyl-N-(2-(3-methoxyphenyl)ethyl)-1,4-diaminobutane

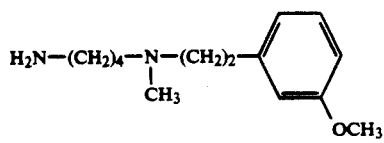

colorless oil
boiling point (°C.): 144~150 (~1 mmHg)
NMR (CDCl₃) δ; 1.40~1.74 (6H, m), 2.30 (3H, s), 2.40 (2H, t, J=7.2 Hz), 2.57~2.63 (2H, m), 2.67~2.78 (4H, m), 3.80 (3H, s), 6.72~6.76 (1H, m), 6.77~6.81 (1H, m), 7.17~7.23 (1H, m), 7.25~7.27 (1H, m)

N-Methyl-N-(2-(4-methylphenyl)ethyl)-1,4-diaminobutane

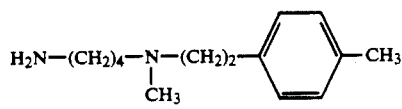

colorless oil
boiling point (°C.): 128~132 (0.5 mmHg)
NMR (CDCl₃) δ; 1.40~1.56 (6H, m), 2.29 (3H, s), 2.31 (3H, s), 2.40 (2H, dt, J=0.8 Hz, 7.6 Hz), 2.55~2.61 (2H, m), 2.67~2.76 (4H, m), 7.09 (4H, s)

N-Methyl-N-(2-(4-methoxy-3-methylphenyl)-ethyl)-1,4-diaminobutane

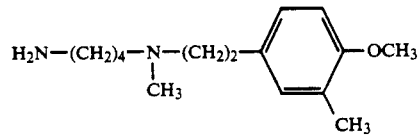

coloress oil
boiling point (°C.): 148~153 (~1 mmHg)
NMR (CDCl₃) δ; 1.20 (2H, s), 1.30~1.62 (4H, m), 2.20~2.82 (11H, m), 3.76 (3H, s), 6.66 (1H, d, J=9 Hz), 6.80~7.00 (2H, m)

PREPARATIVE EXAMPLE 23

N-Methyl-N-(2-(3,4-dimethoxyphenyl)ethyl)-1,5-diaminopentane

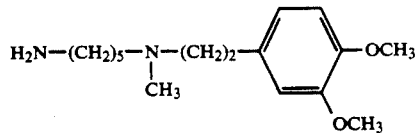

2.5 g of N-methyl-(2-(3,4-dimethoxyphenyl)ethyl)amine was dissolved in 25 ml of N,N-dimethylformamide, followed by the addition of 1.95 g of anhydrous potassium carbonate and 1.65 ml of 4-bromovaleronitrile. The obtained mixture was reacted at room temperature for 16 hours, followed by the addition of water. The obtained mixture was extracted with ethyl acetate. The ethyl acetate layer was washed with water and a saturated aqueous solution of common salt, dried over anhydrous potassium carbonate and distilled to remove the solvent. 40 ml of ethanol, 3.2 ml of concentrated hydrochloric acid and 0.3 g of platinum oxide were added to the obtained residue to carry out hydrogenation at a room temperature under 3 kg/cm² for 6 hours. The catalyst was filtered out and the filtrate was concentrated under a reduced pressure, followed by the addition of concentrated aqueous ammonia. The obtained mixture was extracted with chloroform. The chloroform phase was dried over anhydrous potassium carbonate and distilled to remove the solvent. The residue was purified by silica gel column chromatography [solvent: dichloromethane/methanol/concentrated aqueous ammonia (100:10:1)] to obtain 1.95 g of the title compound as a yellow oil (yield: 55%).
NMR (CDCl₃) δ; 1.2~1.9 (8H, m), 2.2~2.9 (11H, m), 3.83 (3H, s), 3.86 (3H, s), 6.8~6.9 (3H, m)

PREPARATIVE EXAMPLE 24

3-((N-Methyl-N-(2-(3,4-dimethoxyphenyl)ethyl)amino)-2-methylpropyl chloride

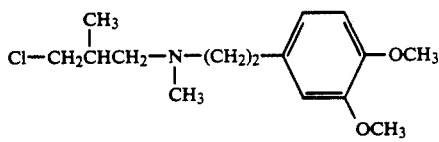

8.0 g of N-methyl-(2-(3,4-dimethoxyphenyl)ethyl)amine was dissolved in 120 ml of N,N-dimethylformamide, followed by the addition of 6.8 g of anhydrous potassium carbonate and 14.4 ml of 1-bromo-3-chloro-2-methylpropane. The obtained mixture was reacted at a room temperature for 12 hours, followed by the addition of water. The obtained mixture was extracted with ethyl acetate. The ethyl acetate phase was washed with water and a saturated aqueous solution of common salt, dried over anhydrous potassium carbonate and distilled to remove the solvent. The obtained residue was purified by silica gel column chromatography [solvent: dichloromethane/methanol (50:1)] to obtain 4.67 g of the title compound as a pale yellow oil (yield:40%).
NMR (CDCl₃) δ; 0.98 (3H, d, J=6.8 Hz), 1.6~2.8 (10H, m), 3.3~3.5 (2H, m), 3.83 (3H, s), 3.85 (3H, s), 6.6~6.8 (3H, m)

PREPARATION EXAMPLE 25

4-((N-Methyl-N-(2-(3,4-dimethoxyphenyl)ethyl)amino)-3-methylpropionitrile

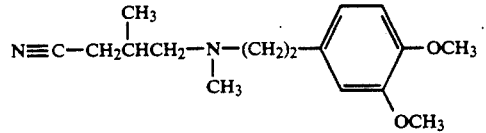

4.67 g of 3-((N-methyl-N-(2-(3,4-dimethoxyphenyl)ethyl)-amino)- 2-methylpropyl chloride was dissolved in 40 ml of acetonitrile, followed by the addition of 2.13 g of potassium cyanide and 0.1 g of 18-crown-6. The obtained mixture was heated under reflux for 40 hours, followed by the addition of water. The obtained mixture was extracted with ethyl acetate. The ethyl acetate phase was washed with water and a saturated aqueous solution of common salt, dried over anhydrous magnesium sulfate and distilled to remove the solvent. The residue was purified by silica gel column chromatography [solvent: n-hexane/ethyl acetate (1:1)] to obtain 3.93 g of the title compound as a pale yellow oil (yield: 87%).

NMR (CDCl$_3$) δ; 1.02 (3H, d, J=6.5 Hz), 1.7~2.8 (12H, m), 3.82 (3H, s), 3.84 (3H, s), 6.6~6.9 (3H, m)

PREPARATIVE EXAMPLE 26

4-((N-Methyl-N-(2-(3,4-dimethoxyphenyl)ethyl)amino-3-methylbutylamine

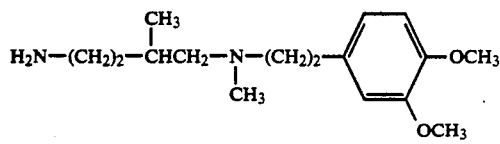

3.93 g of 4-((N-methyl-N-(2-(3,4-dimethoxyphenyl)ethyl)amino)- 3-methylpropionitrile was dissolved in 40 ml of ethanol to obtain a solution. 3.6 ml of concentrated hydrochloric acid and 0.3 g of platinum oxide were added to the solution to carry out hydrogenation at a room temperature under 3 kg/cm$^2$ for 7 hours. The catalyst was filtered out and the filtrate was concentrated under a reduced pressure, followed by the addition of concentrated aqueous ammonia. The obtained mixture was extracted with chloroform. The extract was dried over anhydrous potassium carbonate and distilled to remove the solvent. The obtained residue was purified by silica gel column chromatography [solvent: dichloromethane/methanol/concentrated aqueous ammonia (100:10:1)] to obtain 2.98 g of the title compound as a pale yellow oil (yield: 75%).

NMR (CDCl$_3$) δ; 0.88 (3H, d, J=6.5 Hz), 1.0~2.0 (5H, m), 2.1~2.3 (5H, m), 2.4~2.8 (6H, m), 3.82 (3H, s), 3.84 (3H, s), 6.6~6.9 (3H, m)

PREPARATIVE EXAMPLE 27

Methyl 4-((N-methyl-N-(3,4-dimethoxyphenylacetyl))amino)-pentanoate

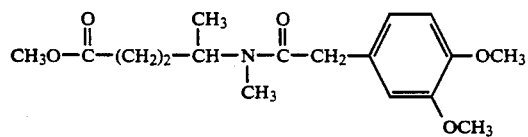

4.5 g of 1,5-dimethyl-2-pyrrolidinone was dissolved in 120 ml of 1N hydrochloric acid to obtain a solution. This solution was heated under reflux for 4 hours, cooled and distilled under a reduced pressure to remove the water. The obtained residue was passed through a Dowex ion-exchange column to obtain an amino carboxylic acid. This amino carboxylic acid was dissolved in 100 ml of water-containing acetone (water content: 50%), followed by the addition of 3.02 g of potassium carbonate. The obtained mixture was cooled to 0° C., followed by the slow dropwise addition of a solution of 8.54 g of 3,4-dimethoxyphenylacetyl chloride in 10 ml of acetone. The obtained mixture was stirred at a room temperature overnight and distilled under a reduced pressure to remove the acetone. The obtained aqueous phase was washed with ethyl acetate and the pH of the aqueous phase was adjusted to 2 to 3 with 2N hydrochloric acid. The resulting aqueous phase was extracted with chloroform thrice. The chloroform phase was distilled under a reduced pressure to remove the chloroform. 50 ml of ether was added to the residue. The obtained mixture was cooled to 0° C., followed by the gradual addition of a solution of diazomethane in ether. The obtained mixture was stirred at a room temperature for one hour. Excessive diazomethane was decomposed with acetic acid. The resulting mixture was extracted with ethyl acetate. The ethyl acetate phase was dried over anhydrous sodium sulfate and distilled to remove the solvent. The obtained residue was purified by silica gel column chromatography [solvent: chloroform/methanol (100:1)] to obtain 2.05 g of the tile compound as a pale yellow oil (yield: 16%).

NMR (CDCl$_3$) δ; 1.09, 1.22 (total 3H, d, J=7 Hz), 1.54~1.90 (2H, m), 2.00~2.46 (2H, m), 2.72, 2.74 (total 3H, s), 3.41~3.74 (5H, m), 3.82 (6H, s), 3.94~4.20, 4.60~4.87 (total 1H, m), 6.71~6.85 (3H, m)

PREPARATIVE EXAMPLE 28

4-((N-Methyl-N-(3,4-dimethoxyphenylacetyl))amino)-pentanamide

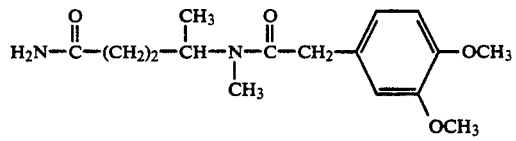

2.05 g of methyl 4-((N-methyl-N-(3,4-dimethoxyphenylacetyl))amino)pentanoate was dissolved in 20 ml of concentrated aqueous ammonia, followed by the addition of 3.3 g of ammonium chloride. The obtained mixture was stirred at a room temperature overnight and extracted with chloroform. The chloroform phase was dried over anhydrous sodium sulfate and distilled to remove the solvent. The residue was purified by silica gel column chromatography [solvent: chloroform/methanol (50:1)] to obtain 1.20 g of the title compound as a pale yellow oil (yield: 63%).

NMR (CDCl$_3$) δ; 0.97, 1.10 (total 3H, each t, J=7 Hz), 1.53~1.88 (2H, m), 1.88~2.10 (2H, m), 2.72, 2.77 (total 3H, each s), 3.56~3.72 (2H, m), 3.84 (6H, s), 3.90~4.19, 4.50~4.88 (total 1H, each m), 6.68~6.88 (3H, m)

PREPARATIVE EXAMPLE 29

4-(N-Methyl-N-(2-(3,4-dimethoxyphenyl)ethyl)amino)-pentylamine

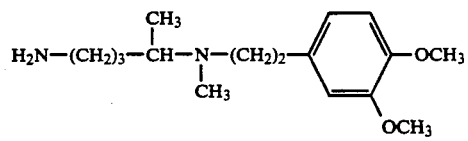

0.2 g of lithium aluminum hydride was suspended in 10 ml of tetrahydrofuran to obtain a suspension. 10 ml of a solution of 0.4 g of 4-((N-methyl-N-(3,4-dimethoxyphenylacetyl))amino)pentanamide in tetrahydrofuran was dropwise added to the suspension at a room temperature. The obtained mixture was heated under reflux for 4 hours and cooled. 1 ml of a 6N aqueous solution of sodium hydroxide and 1 ml of water were successively added to the resulting mixture, followed by stirring. The insoluble matter thus precipitated was filtered out and the filtrate was distilled under a reduced pressure. The residue was purified by silica gel column chromatography [solvent: dichloromethane/methanol/concentrated aqueous ammonia (1000:100:1)] to obtain 0.2 g of the title compound as a pale yellow oil (yield: 55%).

NMR (CDCl$_3$) δ; 0.95 (3H, d, J=7 Hz), 1.48~1.85 (4H, m), 2.15 (3H, s), 2.47~2.92 (6H, m), 3.84 (6H, s), 6.70~6.90 (3H, m)

PREPARATIVE EXAMPLE 30

N-(4-((N'-(2-(3,4-Dimethoxyphenyl)ethyl)-N'-methyl-)amino)-2-butyl)phthalimide

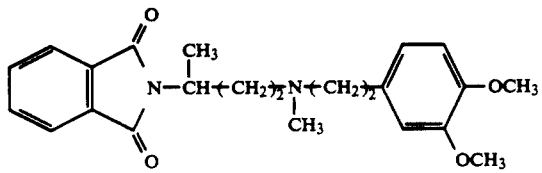

58.5 g of N-methyl-2-(3,4-dimethoxyphenyl)ethylamine was slowly dropwise added to 23.1 g of methyl vinyl ketone under cooling with ice. The obtained mixture was allowed to stand at a room temperature overnight and dissolved in 500 ml of methanol to obtain a solution. 14 g of sodium borohydride was added to the solution in portions under cooling with ice. The obtained mixture was stirred at a room temperature for 2 hours and excessive reagent was decomposed with acetone. The methanol was distilled off under a reduced pressure and the residue was extracted with ethyl acetate. The ethyl acetate phase was dried over anhydrous sodium sulfate, freed from the solvent and purified by silica gel column chromatography [solvent: chloroform/methanol (100:1)] to obtain 70 g of 4-((N-(2-(3,4-dimethoxyphenyl)ethyl)-N-methyl)amino)-2-butanol (yield: 87%).

4.74 g of 4-((N-(2-(3,4-dimethoxyphenyl)ethyl)-N-methyl)amino)-2-butanol, 4.65 g of triphenylphosphine and 2.61 g of phthalimide were dissolved in 50 ml of tetrahydrofuran. The obtained solution was cooled to 0° C., followed by the dropwise addition of 3.09 g of diethyl azodicarboxylate. The obtained mixture was stirred at a room temperature overnight and filtered. The filtrate was concentrated under a reduced pressure. The residue was made acidic by the addition of 1N hydrochloric acid and washed with ethyl acetate. The aqueous phase was made basic with lithium hydroxide and extracted with chloroform. The chloroform phase was dried over anhydrous sodium sulfate and distilled to remove the solvent. The residue was purified by silica gel column chromatography [solvent: chloroform/methanol (100:1)] to obtain 4.2 g of the title compound as a pale yellow oil (yield: 60%).

NMR (CDCl$_3$) δ; 1.50 (3H, d, J=7 Hz), 2.02 (3H, s), 2.24 (3H, s), 2.14~2.68 (8H, m), 3.86 (3H, s), 3.89 (3H, s), 4.34~4.61 (1H, m)m, 6.62~6.88 (3H, m), 7.64~7.96 (4H, m)

PREPARATIVE EXAMPLE 31

4-((N-Methyl-N-(2-(3,4-dimethoxyphenyl)ethyl-)amino)-2-butylamine

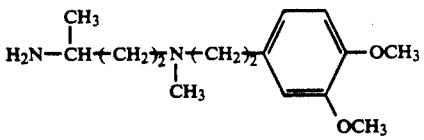

4.8 g of N-(4-((N'-(2-(3,4-dimethoxyphenyl)ethyl)-N'-methyl)amino)-2-butyl)phthalimide was dissolved in 50 ml of ethanol, followed by the addition of 0.73 g of hydrazine monohydrate. The obtained mixture was heated under reflux for 2 hours and cooled. The formed precipitate was filtered out and the filtrare was concentrated under a reduced pressure. The residue was purified by silica gel column chromatography [solvent: chloroform/methanol/concentrated aqueous ammonia (250:25:1)] to obtain 2.58 g of the title compound as a pale yellow oil (yield: 80%).

NMR (CDCl$_3$) δ; 1.07 (3H, d, J=6 Hz), 1.32~1.89 (4H, m), 2.28 (3H, s), 2.32~3.07 (7H, m), 3.81 (3 H, s), 3.84 (3H, s), 6.55~6.85 (3H, m)

PREPARATIVE EXAMPLE 32

N-Methyl-N-(4-(tert-butyldimethylsiloxy)-butan-2-yl)-[2-(3,5-dimethoxyphenyl)ethyl]amine

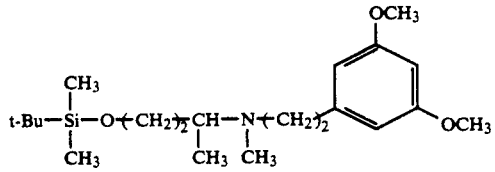

2.16 g of methanesulfonyl chloride was slowly added to 30 ml of a solution of 3.50 g of 4-(tert-butyldimethylsiloxy)butan-2-ol and 1.90 g of triethylamine in ether under cooling with ice. After 30 minutes, water was added to the obtained mixture, followed by the extraction with ether. The ether phase was dried over anhydrous sodium sulfate and filtered. The filtrate was distilled to remove the ether. The residue was dissolved in 30 ml of acetonitrile, followed by the addition of 3.37 g of N-methyl-[2-(3,5-dimethyoxypheny)ethyl]amine and 3.48 g of potassium carbonate. The obtained mixture was heated under reflux for 12 hours and cooled to precipitate a crystal. The crystal was filtered out and the filtrate was concentrated under a reduced pressure and extracted with ether thrice. The ether phase was washed with an aqueous solution of common salt, dried over anhydrous sodium-sulfate and filtered. The filtrate was concentrated under a reduced pressure and purified by silica gel column chromatography [solvent: chloroform/methanol (100:1)] to obtain 3.33 g of the title compound as a yellow oil (yield: 56%).

NMR (CDCl$_3$) δ; 0.04 (6H, s), 0.89 (9H, s), 0.95 (3H, d, J=6.6 Hz), 1.38~1.92 (2H, m), 2.25 (3H, s), 2.40~2.96 (5H, m), 3.58 (2H, t, J=6.6 Hz), 3.77 (6H, s), 6.20~6.39 (3H, m)

PREPARATIVE EXAMPLE 33

3-(N-Methyl-N-(2-(3,5-dimethoxyphenyl)ethyl)amino)-butylamine

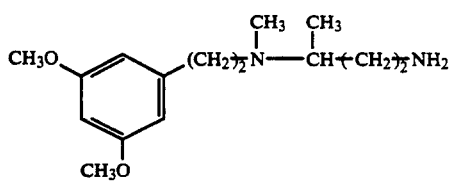

3.33 g of N-methyl-N-(4-(tert-butyldimethylsiloxy)-butan-2-yl)-[2-(3,5-dimethoxyphenyl)ethyl]amine was dissolved in 13 ml of tetrahydrofuran to obtain a solution. 13 ml of a solution of tetra-n-butylammonium fluoride in tetrahydrofuran (1 mmol/ml) was slowly dropwise added to the solution. The obtained mixture was stirred at a room remperature for 3 hours and distilled to remove the solvent. The residue was extracted with ether thrice and the ether phase was dried over anhydrous sodium sulfate and concentrated under a reduced pressure. The residue was dissolved in 25 ml of tetrahydrofuran, followed by the addition of 1.29 g of phthalimide and 2.29 g of triphenylphosphine. 1.52 g of diethyl azodicarboxylate was slowly added to the obtained mixture at a room temperature. The obtained mixture was stirred overnight and distilled to remove the solvent. The residue was made acidic with 0.5N hydrochloric acid and washed with ether. The aqueous phase was made basic with lithium hydroxide and extracted with ethyl acetate. The ethyl acetate phase was dried over anhydrous sodium sulfate and the filtrate was concentrated under a reduced pressure to obtain a residue. This resiude was dissolved in 20 ml of ethanol, followed by the addition of 200 mg of hydrazine monohydrate. The obtained mixture was heated under reflux for 2 hours and cooled. The white precipitate thus formed was filtered out and the filtrate was concentrated under a reduced pressure, followed by the addition of 20 ml of a 10% solution of sodium hydroxide. The obtained mixrure was extracted with chloroform thrice. The chloroform phase was washed with a saturated aqueous solution of common salt, dried over anhydrous sodium sulfate and concentrated under a reduced pressure to obtain 830 mg of the title compound as a yellow oil (yield: 36%).

NMR (CDCl₃) δ; 0.92 (3H, d, J=6.3 Hz), 1.18~2.08 (4H, m), 2.24 (3H, s), 2.52~2.92 (7H, m), 3.77 (6H, s), 6.20~6.36 (3H, m)

PREPARATIVE EXAMPLE 34

N-Methyl-N-(2-(3-chloro-1-methoxyphenyl)ethyl)-1,4-diaminobutane

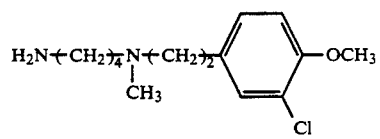

A mixture comprising 5.00 g of N-methyl-(2-(3-chloro-4-methoxyphenyl)ethylamine, 9.49 g of N-(4-bromobutyl)phthalimide, 4.16 g of anhydrous potassium carbonate and 50 ml of N,N-dimethylformamide was stirred at a room temperature for 14 hours, followed by the addition of water. The obtained mixture was extracted with ethyl acetate and the ethyl acetate phase was washed with water and a saturated aqueous solution of common salt, dried over anhydrous magnesium sulfate and concentrated, followed by the addition of 50 ml of ethanol and 1.5 ml of hydrazine monohydrate. The obtained mixture was heated under reflux for 2 hours, cooled by allowing to stand and filtered to remove insoluble matter. The filtrate was distilled to obtain 3.16 g of the title compound as a colorless oil (yield: 47%).

boiling point (°C.): 167~172 (~1 mmHg)

NMR (CDCl₃) δ; 1.20 (2H, s), 1.30~1.64 (4H, m), 2.20~2.84 (11H, m), 3.82 (3H, s), 6.77 (1H, d, J=8.6 Hz), 6.98 (1H, dd, J=2.2 Hz, 8.6 Hz), 8.15 (1H, d, J=2.2 Hz)

PREPARATIVE EXAMPLE 35

The following compounds were prepared in a similar manner to that of Preparative Example 34.

N-Methyl-N-(2-(4-chlorophenyl)ethyl)-1,4-diaminobutane

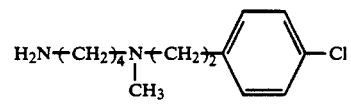

colorless oil boiling point (°C.): 143~147 (~1 mmHg)

NMR (CDCl₃) δ; 1.25~1.72 (6H, m), 2.28 (3H, s), 2.39 (2H, t, J=7.6 Hz), 2.54~2.60 (2H, m), 2.66~2.76 (4H, m), 7.12 (2H, d, J=8.8 Hz), 7.24 (2H, d, J=8.8 Hz)

N-Methyl-N-(2-(3,4-dichlorophenyl)ethyl)-1,4-diaminobutane

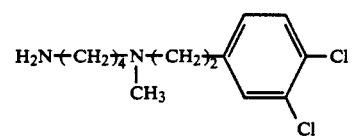

colorless oil boiling point (°C.): 163~165 (~1 mmHg)

NMR (CDCl₃) δ; 1.36~1.68 (6H, m), 2.27 (3H, s), 2.38 (2H, t, J=7.6 Hz), 2.54~2.59 (2H, m), 2.67~2.74 (4H, m), 7.03 (1H, dd, J=2.4 Hz, 8.4 Hz), 7.24 (1H, d, J=2.4 Hz), 7.33 (1H, d, J=8.4 Hz)

EXAMPLE 1

(E)-[N-(3-((N'-(2-(3,4-Dimethoxyphenyl)ethyl)-N'-methyl)amino)propyl]-4-(4-(N³-methyl-N²-cyanoguanidino)phenyl)-3-butenamide

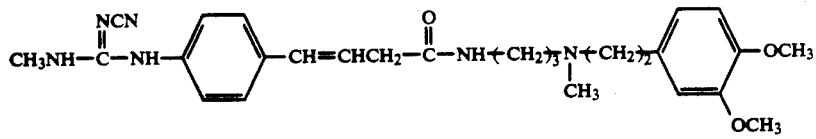

0.8 g of (E)-4-(4-(N³-methyl-N²-cyanoguanidino)phenyl)-3-butenoic acid, 0.86 g of N-methyl-N-(2-(3,4-dimethoxyphenyl)ethyl)-1,3-diaminopropane, 0.71 g of N,N-dicyclohexylcarbodiimide and 0.46 g of N-hydroxybenzotriazole were added to 7 ml of acetonitrile. The obtained mixture was stirred at 70° C. for 30 minutes and cooled, followed by the addition of dilute hydrochloric acid. The obtained mixture was filtered to remove insoluble matter. The filtrate was made alkaline by the addition of potassium carbonate and extracted with chloroform. The chloroform phase was dried over anhydrous potassium carbonate and distilled under a reduced pressure to remove the solvent. The residue was purified by silica gel column chromatography [solvent: dichloroethane/methanol/concentrated aqueous ammonia (100:100:3)] to obtain 1.09 g of the title compound as a yellow amorphous product (yield: 71%).

NMR (CDCl₃) δ; 1.5~1.9 (2H, m), 2.23 (3H, s), 2.3~2.9 (6H, m), 2.84 (3H, d, J=4.3 Hz), 2.98 (2H, d, J=5.8 Hz), 3.1~3.5 (2H, m), 3.81 (6H, s), 5.22 (1H, br), 6.16 (1H, dt, J=5.8 Hz, 15.1 Hz), 6.39 (1H, d, J=15.1 Hz), 6.5~6.9 (3H, m), 7.0~7.4 (5H, m), 7.56 (1H, br)

EXAMPLE 2

(E)-[N-(3-((N'-(2-(3,5-Dimethoxyphenyl)ethyl)-N'-methyl)amino)propyl]-4-(4-(N³-methyl-N²-cyanoguanidino)phenyl)-3-butenamide 0.6 g of (E)-4-(4-(N³-methyl-N²-cyanoguanidino)phenyl)-3-butenoic acid, 0.65 g of N-methyl-N-(2-(3,5-diemthoxyphenyl)ethyl)-1,3-propanediamine, 0.53 g of N,N-dicyclohexylcarbodiimide and 0.35 g of N-hydroxybenzotriazole were added to 6 ml of acetonitrile. The obtained mixture was stirred at 70° C. for 30 minutes, cooled and filtered to remove insoluble matter. The filtrate was concentrated under a reduced pressure, made alkaline by the addition of a dilute aqueous solution of potassium carbonate and extracted with chloroform. The chloroform phase was dried over anhydrous potassium carbonate and distilled under a reduced pressure to remove the solvent. The residue was purified by silica gel column chromatography [solvent: dichloromethane/methanol/concentrated aqueous ammonia (500:50:1)] to obtain 0.92 g of the title compound as a pale yellow amorphous product (yield: 81%).

NMR (CDCl₃) δ; 1.5~1.8 (2H, m), 2.20 (3H, s), 2.3~2.7 (6H, m), 2.84 (3H, d, J=4.8 Hz), 2.99 (2H, d, J=6.2 Hz), 3.1~3.5 (2H, m), 5.16 (1H, br), 6.0~6.5 (5H, m), 7.0~7.4 (5H, m), 7.54 (1H, br)

EXAMPLE 3

(E)-[N-(4-((N'-(2-(3,5-Dimethoxyphenyl)ethyl)-N'-methyl)amino)butyl]-4-(4-(1,4-dihydro-4-oxo-1-pyridyl)phenyl)-3-butenamide 5.32 g of (E)-4-(4-(1,4-dihydro-4-oxo-1-pyridyl)phenyl)-3-butenoic acid, 5.85 g of N-methyl-N-(2-(3,5-dimethoxyphenyl)ethyl)-1,4-diaminobutane, 4.54 g of N,N-dicyclohexylcarbodiimide and 2.97 g of N-hydroxybenzotriazole were added to 60 ml of acetonitrile. The obtained mixture was stirred at 60° to 70° C. for 40 minutes and cooled, followed by the addition of dilute hydrochloric acid. The insoluble matter thus formed was filtered out and the filtrate was washed with ethyl acetate, followed by the addition of dilute aqueous ammonia. The obtained mixture was extracted with chloroform. The chloroform phase was dried over anhydrous potassium carbonate and distilled under a reduced pressure. The residue was purified by silica gel column chromatography [solvent: methanol/concentrated aqueous ammonia (200:20:1)] to obtain 6.75 g of the title compound as a pale yellow oil (yield: 67%).

NMR (CDCl₃) δ; 1.4~1.7 (4H, m), 2.2~2.8 (9H, m), 3.0~3.4 (4H, m), 3.76 (6H, s), 6.1~6.8 (8H, m), 7.1~7.6 (6H, m)

EXAMPLE 4

(E)-[N-(4-((N'-(2-(3,5-Dimethoxyphenyl)ethyl)-N'-methyl)amino)butyl]-4-(4-(1H-imidazol-1-yl)phenyl)-3-butenamide

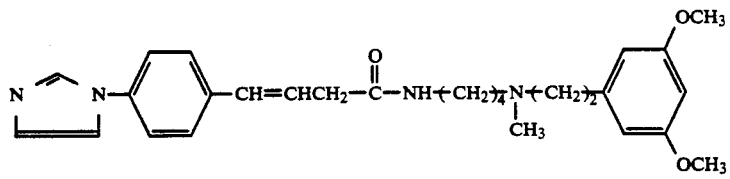

3.42 g of (E)-4-(4-(1H-imidazol-1-yl)phenyl)-3-butenoic acid, 4.39 g of N-methyl-N-(2-(3,5-dimethoxyphenyl)ethyl)-1,4 diaminobutane, 3.40 g of N,N-dicyclohexylcarbodiimide and 2.23 g of N-hydroxybenzotriazole were added to 50 ml of acetonitrile. The obtained mixture was stirred at 70° C. for 40 minutes, cooled and filtered to remove insolubel matter. Dilute aqueous ammonia was added to the filtrate, followed by the extraction with chloroform. The chloroform phase was dried over anhydrous potassium carbonate and distilled under a reduced pressure to remove the solvent. The residue was purified by silica gel column chromatography [solvent: dichloromethane/methanol/concentrated aqueous ammonia (1000:100:3)] to obtain 5.41 g of the title compound as a pale yellow oil (yield: 76%).

NMR (CDCl$_3$) δ; 1.4~1.7 (4H, m), 2.3~2.8 (9H, m), 3.0~3.5 (4H, m), 3.76 (6H, s), 6.1~6.8 (6H, m), 7.1~7.5 (6H, m), 7.83 (1H, s)

EXAMPLE 5

(E)-[N-(4-((N'-(2-(3,4-Dimethoxyphenyl)ethyl)-N'-methyl)amino)pentyl]-4-(4-(1,4-dihydro-4-oxo-1-pyridyl)phenyl)-3-butenamide

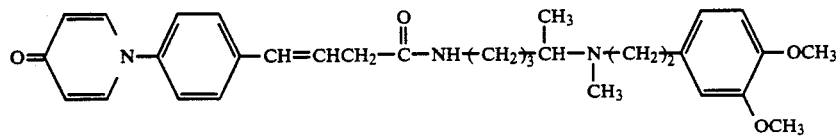

0.35 g of (E)-4-(4-(1,4-dihydro-4-oxo-1-pyridyl)-phenyl)-3-butenoic acid, 0.2 g of 4-[(N-methyl-N-(2-(3,4-dimethoxyphenyl)ethyl))amino]pentylamine, 0.4 g of N,N-dicyclohexylcarbodiimide and 0.26 g of N-hydroxybenzotriazole were added to 10 ml of acetonitrile. The obtained mixture was stirred at 60° C. for 30 minutes, cooled and filtered to remove insoluble matter. The filtrate was concentrated under a reduced pressure and made acidic by the addition of dilute hydrochloric acid. The aqueous phase was washed with ethyl acetate, followed by the addition of a dilute aqueous solution of lithium hydroxide. The obtained mixture was extracted with chloroform. The chloroform phase was dride over anhydrous sodium sulfate and distilled under a reduced pressure. The residue was purified by silica gel column chromatography [solvent: dichloromethane/methanol/concentrated aqueous ammonia (400:40:1)] to obtain 0.3 g of the title compound as a pale yellow oil (yield: 81%).

NMR (CDCl$_3$) δ; 0.97 (3H, d, J=6 Hz), 1.20~1.96 (4H, m), 2.32 (3H, s), 2.52~2.96 (5H, m), 3.06~3.64 (4H, m), 3.82 (3H, s), 3.84 (3H, s), 6.30~6.92 (6H, m), 7.08~7.70 (8H, m)

EXAMPLE 6

(E)-N-[(4-((N'-(2-(3,5-Dimethoxyphenyl)ethyl)-N'-methyl)amino)butyl]-4-[4-(4-nitro-1H-imidazol-1-yl)phenyl]-3-butenamide

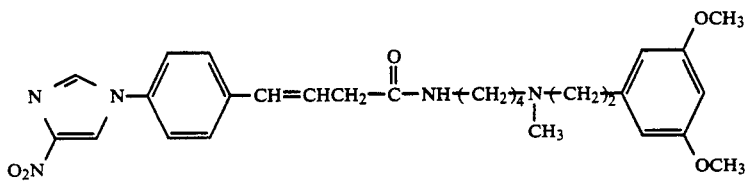

585 mg of N-methyl-N-[2-(3,5-dimothoxyphenyl)ethyl]-1,4-diaminobutane was added to a suspension of 546 mg of (E)-4-[(4-nitro-1H-imidazol-1-yl)phenyl]-3-butenoic acid, 453 mg of N,N'-dicyclohexylcarbodiimide and 300 mg of N-hydroxybenzotriazole in 30 ml of dioxane at a room temperature under stirring. The obtained reaction mixture was stirred at 40° to 50° C. for about one hour and poured into water, followed by the addition of ethyl acetate. The insoluble matter thus formed was filtered out and the organic phase was separated, washed with an aqueous solution of sodium hydrogencarbonate and water, dried over magnesium sulfate and purified by silica gel column chromatography [solvent: dichloromethane/ethanol] to obtain 440 mg of the title compound as a lightly red oil.

NMR (CDCl$_3$) δ; 1.5~1.7 (4H, m), 2.32 (3H, s), 2.3~2.6 (2H, m), 2.6~2.9 (4H, m), 3.1~3.6 (4H, m), 3.76 (6H, s), 6.24~6.7 (6H, m), 7.24~7.6 (4H, m), 7.76 (1H, d, J=1 Hz), 8.08 (1H, d, J=1 Hz)

EXAMPLE 7

(E)-N-[4-((N'-(2-(3,5-Dimethoxyphenyl)ethyl)-N'-methyl)amino)butyl]-4-(2-(1H-imidazol-1-yl)thiophen-5-yl)-3-butenamide

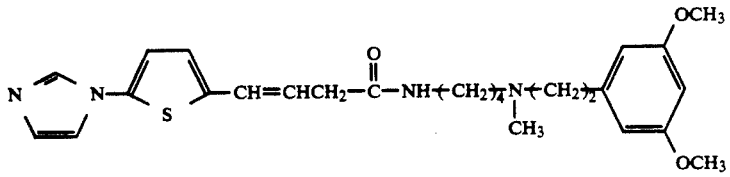

0.48 g of 4-(2-(1H-imidazol-1-yl)thiophen-5-yl)-3-butenoic acid, 0.51 g of N,N'-dicyclohexylcarbodiimide, 0.33 g of N-htdroxybenzotriazole, 0.65 g of N-2-((3,5-dimethoxyphenyl)ethyl)-N-methyl-1,4-diaminobutane and an acetonitrile (50 ml)/water (10 ml) mixture were together stirred at 60° C. for 30 minutes to precipitate a crystal. This crystal was filtered out and the filtrate was concentrated under a reduced pressure and purified by silica gel column chromatography to obtain 0.95 g of the title compound as a yellow oil.

NMR (CDCl$_3$) δ; 1.4~1.7 (4H, m), 2.29 (3H, s), 2.3~2.8 (6H, m), 3.07 (2H, d, J=6.5 Hz), 3.1~3.4 (2H, m), 3.77 (6H, s), 6.12 (1H, dt, J=16.0 Hz, 6.5 Hz), 6.3~6.4 (3H, m), 6.53 (1H, d, J=16.0 Hz), 6.6 (1H, m), 6.7~6.9 (2H, m), 7.1~7.2 (2H, m), 7.7 (1H, m)

EXAMPLES 8 TO 52

The compounds which will be described in Examples 8 to 52 were prepared in a similar manner to that of Example 1.

Namely, the same procedure as that of Example 1 was repeated except that the (E)-4-(4-(N$^3$-methyl-N$^2$-cyanoguanidino)phenyl)-3-butenoic acid was replaced by the corresponding 4-substituted phenyl-3-butenoic acid and the N-methyl-N-(2-(3,4-dimethoxyphenyl)ethyl)-1,3-diaminopropane was replaced by the corresponding substituted diaminoalkane to obtain the compounds which will be described below.

EXAMPLE 8

(E)-[N-(3-((N'-(2-(3,5-Dimethoxyphenyl)ethyl)-N'-methyl)amino)propyl]-4-(4-(1,4-dihydro-4-oxo-1-pyridyl)phenyl)-3-butenamide

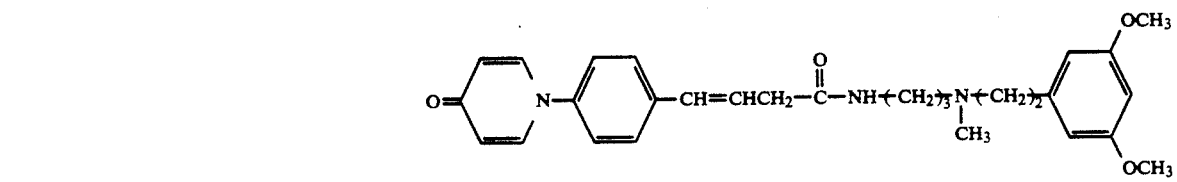

pale yellow oil
NMR (CDCl$_3$) δ; 1.5~1.8 (2H, m), 2.22 (3H, s), 2.3~2.7 (6H, m), 3.07 (2H, d, J=5.7 Hz), 3.1~3.5 (2H, m), 3.75 (6H, s), 6.0~6.6 (7H, m), 7.0~7.6 (7H, m)

EXAMPLE 9

(E)-[N-(3-((N'-(2-(3,4-Dimethoxyphenyl)ethyl)-N'-methyl)amino)propyl]-4-(4-(N$^2$-methylthioureido)-phenyl)-3-butenamide

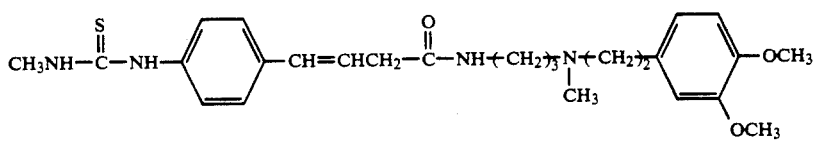

pale yellow oil
NMR (CDCl$_3$) δ; 1.5~1.9 (2H, m), 2.24 (3H, s), 2.3~2.7 (6H, m), 3.00 (3H, d, J=6.2 Hz), 3.09 (2H, d, J=4.8 Hz), 3.2~3.5 (2H, m), 3.83 (6H, s), 6.08 (1H, dt, J=4.8 Hz, 15.1 Hz), 6.2~6.5 (2H, m), 6.5~6.8 (3H, m), 7.0~7.4 (5H, m), 8.34 (1H, br s)

EXAMPLE 10

(E)-[N-(4-((N'-(2-(3,4-Dimethoxyphenyl)ethyl)-N'-methyl)amino)butyl]-4-(4-(1H-imidazol-1-yl)phenyl)-3-butenamide

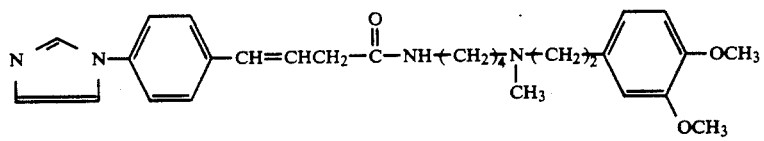

pale yellow oil
NMR (CDCl$_3$) δ; 1.4~1.8 (4H, m), 2.2~2.8 (9H, m), 2.9~3.4 (4H, m), 3.84 (3H, s), 3.86 (3H, s), 6.24 (1H, dt, J=6.2 Hz, 15.8 Hz), 6.4~6.8 (5H, m), 7.1~7.5 (6H, m), 7.83 (1H, s)

EXAMPLE 11

(E)-[N-(4-((N'-(2-(3,4-Dimethoxyphenyl)ethyl)-N'-methyl)amino)butyl]-4-(4-(1,4-dihydro-4-oxo-1-pyridyl)phenyl)-3-butenamide

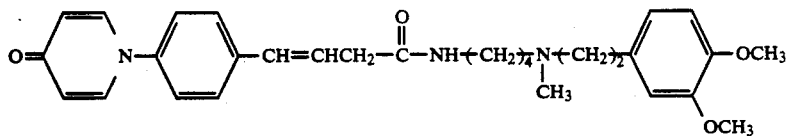

pale yellow oil
NMR (CDCl$_3$) δ; 1.4~1.8 (4H, m), 2.2~2.9 (9H, m), 3.0~3.4 (4H, m), 3.82 (3H, s), 3.84 (3H, s), 6.2~6.6 (4H, m), 6.6~7.0 (4H, m), 7.1~7.7 (6H, m)

EXAMPLE 12

(E)-[N-(4-((N'-(2-(3,4-Dimethoxyphenyl)ethyl)-N'-methyl)amino)butyl]-4-(4-(N$^3$-methyl-N$^2$-cyanoguanidino)phenyl)-3-butenamide

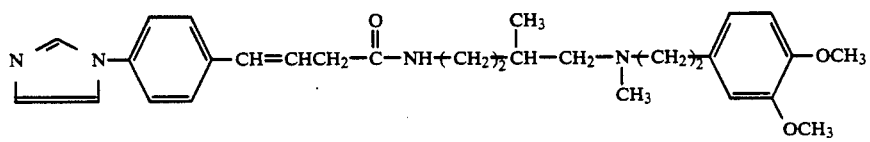

pale yellow amorphous product
NMR (CDCl$_3$) δ; 1.35~1.74 (4H, m), 2.31 (3H, s), 2.34~2.76 (6H, m), 2.85 (3H, d, J=4.8 Hz), 2.96~3.34 (4H, m), 3.83 (3H, s), 3.84 (3H, s), 5.26~5.53 (1H, m), 6.20 (1H, dt, J=5.7 Hz, 15.8 Hz), 6.44 (1H, d, J=15.8 Hz), 6.51~6.82 (4H, m), 6.99~7.35 (4H, m), 7.53~7.82 (1H, m)

EXAMPLE 13

(E)-[N-(4-((N'-(2-(3,5-Dimethoxyphenyl)ethyl)-N'-methyl)amino)butyl]-4-(4-(N$^3$-methyl-N$^2$-cyanoguanidino)phenyl)-3-butenamide

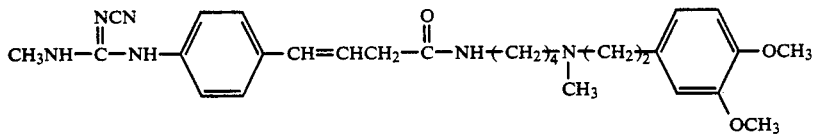

lightly orange-colored amorphous product

NMR (CDCl$_3$) δ; 1.32~1.72 (4H, m), 2.29 (3H, s), 2.30~2.75 (6H, m), 2.85 (3H, d, J=4.8 Hz), 2.98~3.31 (4H, m), 3.76 (6H, s), 5.26~5.47 (3H, m), 5.98~6.37 (5H, m), 6.53~6.71 (1H, m), 6.97~7.35 (4H, m), 7.51~7.82 (1H, m)

EXAMPLE 14

(E)-[N-(4-((N'-(2-(3,4-Dimethoxyphenyl)ethyl)-N'-methyl)amino)-3-methylbutyl]-4-(4-(1H-imidazol-1-yl)phenyl)-3-butenamide

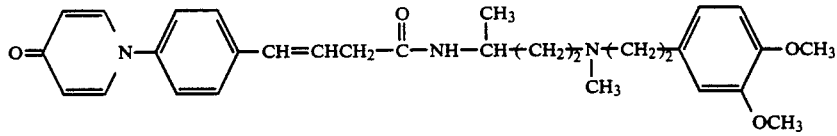

pale yellow oil
NMR (CDCl$_3$) δ; 0.94 (3H, d, J=6.5 Hz), 1.3~1.9 (3H, m), 2.1~2.4 (5H, m), 2.5~2.9 (4H, m), 3.0~3.5 (4H, m), 3.82 (3H, s), 3.84 (3H, s), 6.28 (1H, dt, J=6.1 Hz, 15.5 Hz), 6.56 (1H, d, J=15.5 Hz), 6.6~6.9 (3H, m), 7.0~7.5 (7H, m), 7.84 (1H, br s)

EXAMPLE 15

(E)-[N-(4-((N'-(2-(3,4-Dimethoxyphenyl)ethyl)-N'-methyl)amino)-2-butyl]-4-(4-(1,4-dihydro-4-oxo-1-pyridyl)phenyl)-3-butenamide

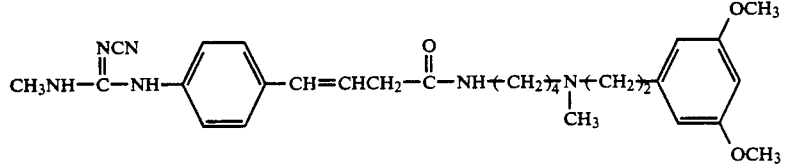

pale yellow oil
NMR (CDCl$_3$) δ; 1.20 (3H, d, J=7 Hz), 1.46~1.84 (2H, m), 2.26 (3H, s), 2.36~2.83 (6H, m), 3.04 (2H, d, J=6 Hz), 3.80 (3H, s), 3.83 (3H, s), 3.92~4.22 (1H, m), 6.28~6.84 (7H, m), 7.04~7.80 (7H, m)

EXAMPLE 16

(E)-[N-(3-((N'-(2-(3,4-Dimethoxyphenyl)ethyl)-N'-methyl)amino)butyl]-4-(4-(1,4-dihydro-4-oxo-1-pyridyl)phenyl)-3-butenamide

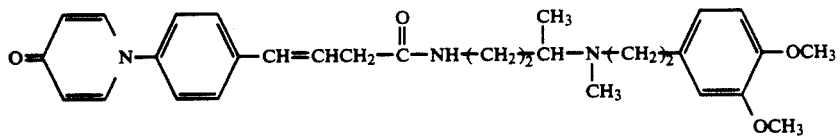

pale yellow oil
NMR (CDCl$_3$) δ; 0.94 (3H, d, J=7 Hz), 1.34~1.89 (2H, m), 2.18 (3H, s), 2.34~2.82 (4H, m), 2.92~3.64 (5H, m), 3.79 (3H, s), 3.82 (3H, s), 6.18~6.78 (5H, m), 7.00~7.66 (7H, m)

EXAMPLE 17

(E)-[N-(3-((N'-(2-(3,5-Dimethoxyphenyl)ethyl)-N'-methyl)amino)butyl]-4-(4-(1,4-dihydro-4-oxo-1-pyridyl)phenyl)-3-butenamide

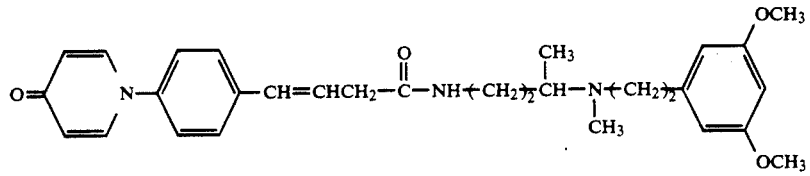

pale yellow oil
NMR (CDCl$_3$) δ; 0.92 (3H, d, J=6.6 Hz), 1.2~1.9 (2H, m), 2.16 (3H, s), 2.3~3.3 (8H, m), 3.3~3.7 (1H, m), 3.75 (6H, s), 6.1~6.6 (7H, m), 7.0~7.3 (3H, m), 7.3~7.6 (4H, m)

EXAMPLE 18

(E)-[N-(3-((N'-(2-(3,4-Dimethoxyphenyl)ethyl)-N'-methyl)amino)propyl]-4-(4-(N$^2$-cyanopropanamidino)phenyl)-3-butenamide

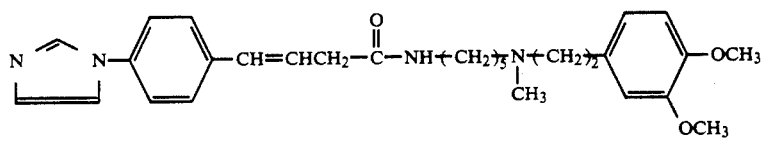

m.p. (°C.): 137 to 138
elemental analysis as C$_{28}$H$_{37}$N$_5$O$_3$:

|  | C | H | N |
|---|---|---|---|
| calculated (%) | 68.40 | 7.59 | 14.25 |
| found (%) | 68.65 | 7.61 | 14.48 |

NMR (CDCl$_3$) δ; 1.40 (3H, t, J=7.5 Hz), 1.5~1.9 (2H, m), 2.24 (3H, s), 2.4~2.9 (8H, m), 2.95 (2H, d, J=5.7 Hz), 3.1~3.5 (2H, m), 3.82 (3H, s), 3.84 (3H, s), 6.00 (1H, dt, J=5.7 Hz, 15.8 Hz), 6.36 (1H, d, J=15.8 Hz), 6.5~6.9 (3H, m), 6.9~7.2 (2H, m), 7.3~7.6 (3H, m), 9.65 (1H, br s)

EXAMPLE 19

(E)-[N-(5-((N'-(2-(3,4-Dimethoxyphenyl)ethyl)-N'-methyl)amino)pentyl]-4-(4-(1H-imidazol-1-yl)phenyl)-3-butenamide

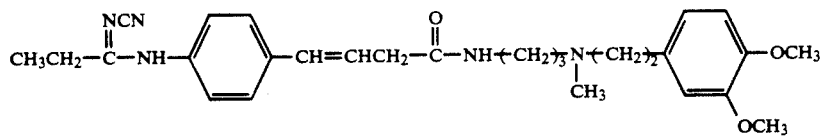

pale yellow oil
NMR (CDCl$_3$) δ; 1.1~1.8 (6H, m), 2.2~2.9 (9H, m), 3.0~3.5 (4H, m), 3.84 (3H, s), 3.86 (3H, s), 5.82 (1H, m), 6.26 (1H, dt, J=5.7 Hz, 15.1 Hz), 6.54 (1H, d, J=15.1 Hz), 6.6~6.9 (3H, m), 7.0~7.5 (6H, m), 7.83 (1H, br s)

EXAMPLE 20

(E)-[N-(4-((N'-(2-(3,4-Dimethoxyphenyl)ethyl)-N'-methyl)amino)pentyl]-4-(4-(1H-imidazol-1-yl)phenyl-3-butenamide

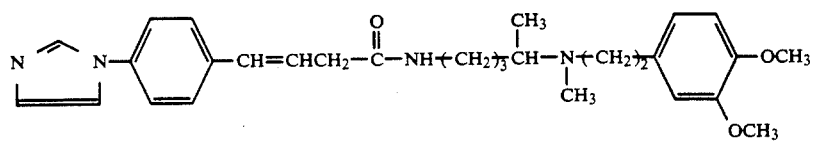

pale yellow oil
NMR (CDCl₃) δ; 0.97 (3H, d, J=6 Hz), 1.24~1.72 (4H, m), 2.31 (3H, s), 2.48~2.91 (5H, m), 3.16~3.68 (4H, m), 3.84 (3H, s), 3.86 (3H, s), 6.18~6.92 (6H, m), 7.08~7.56 (6H, m), 7.83 (1H, s)

EXAMPLE 21

(E)-N-[4-((N'-2-Phenylethyl)-N'-methyl)amino)butyl]-4-(4-(1H-imidazol-1-yl)phenyl)-3-butenamide

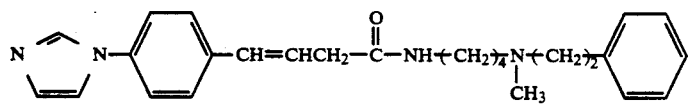

yellow oil
NMR (CDCl₃) δ; 1.45~1.67 (4H, m), 2.23~2.91 (9H, m), 3.06~3.39 (4H, m), 6.31 (1H, dt, J=5.7 Hz, 15.8 Hz), 6.54 (1H, d, J=15.8 Hz), 6.79 (1H, br), 7.05~7.51 (11H, m), 7.81 (1H, s)

EXAMPLE 22

(E)-N-[4-((N'-(2-(4-Methoxypehnyl)ethyl)-N'-methyl)amino)butyl]-4-(4-(1H-imidazol-1-yl)phenyl-3-butenamide

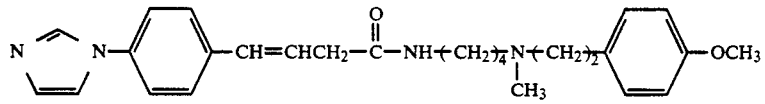

pale yellow oil
NMR (CDCl₃) δ; 1.41~1.72 (4H, m), 2.22~2.85 (9H, m), 3.06~3.39 (4H, m), 3.74 (3H, s), 6.29 (1H, dt, J=5.5 Hz, 15.8 Hz), 6.53 (1H, d, J=15.8 Hz), 6.79 (1H, d, J=8.4 Hz), 6.89~7.49 (9H, m), 7.81 (1H, s)

EXAMPLE 23

(E)-N-[4-((N'-(2-(3-Methoxyphenyl)ethyl)-N'-methyl)amino)butyl]-4-(4-(1H-imidazol-1-yl)phenyl)-3-butenamide

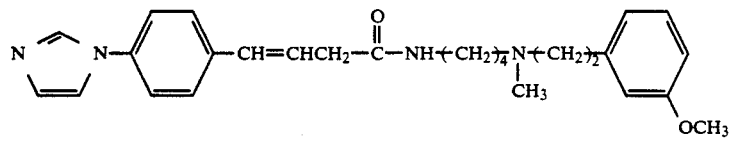

pale yellow oil

NMR (CDCl₃) δ; 1.43~1.63 (4H, m), 2.21~2.87 (9H, m), 3.06~3.38 (4H, m), 3.78 (3H, s), 6.19 (1H, dt, J=5.7 Hz, 15.8 Hz), 6.54 (1H, br), 6.55 (1H, d, J=15.8 Hz), 6.65~6.85 (2H, m), 7.07~7.55 (8H, m), 7.82 (1H, s)

EXAMPLE 24

(E)-N-[4-((N'-(2-(4-Chlorophenyl)ethyl)-N'-methyl)amino)butyl]-4-(4-(1H-imidazol-1-yl)phenyl)-3-butenamide

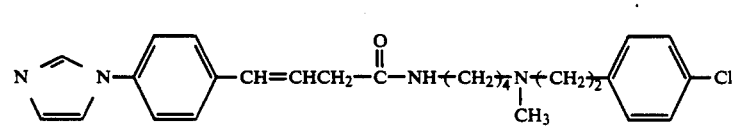

pale yellow oil
NMR (CDCl₃) δ; 1.41~1.64 (4H, m), 2.18~2.85 (9H, m), 3.06~3.38 (4H, m), 6.19 (1H, dt, J=5.7 Hz, 15.8 Hz), 6.55 (1H, d, J=15.8 Hz), 6.95~7.51 (11H, m), 7.82 (1H, s)

EXAMPLE 25

(E)-N-[4-((N'-(2-(3,4-Dichlorophenyl)ethyl)-N'-methyl)amino)butyl]-4-(4-(1H-imidazol-1-yl)phenyl)-3-butenamide

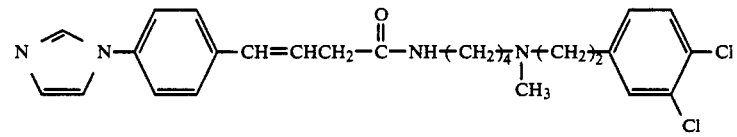

pale yellow oil
NMR (CDCl₃) δ; 1.41~1.64 (4H, m), 2.26 (3H, s), 2.30~2.85 (6H, m), 3.08~3.36 (4H, m), 6.28 (1H, br), 6.31 (1H, dt, J=5.7 Hz, 15.8 Hz), 6.55 (1H, d, J=15.8 Hz), 7.00 (1H, dd, J=2.2 Hz, 7.9 Hz), 7.11~7.56 (8H, m), 7.83 (1H, s)

EXAMPLE 26

(E)-N-[4-((N'-(2-(4-Methylphenyl)ethyl)-N'-methyl-)amino)butyl]-4-(4-(1H-imidazol-1-yl)phenyl)-3-butenamide

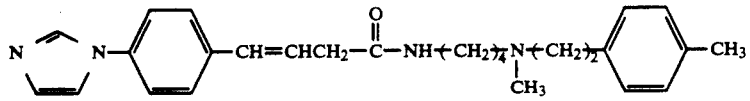

yellow oil
NMR (CDCl₃) δ; 1.47~1.75 (4H, m), 2.15~2.90 (12H, m), 3.08~3.39 (4H, m), 6.29 (1H, dt, J=5.7 Hz, 15.8 Hz), 6.55 (1H, d, J=15.8 Hz), 6.70 (1H, br), 7.06 (4H, s), 7.12~7.63 (7H, m), 7.81 (1H, s)

EXAMPLE 27

(E)-N-[4-((N'-(2-(4-Methoxy-3-methylphenyl)ethyl)-N'-methyl)amino)butyl]-4-(4-(1H-imidazol-1-yl)phenyl)-3-butenamide

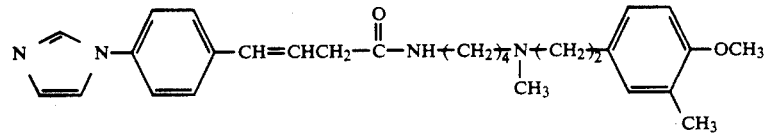

pale yellow oil
NMR (CDCl₃) δ; 1.40~1.75 (4H, m), 2.18 (3H, s), 2.32 (3H, s), 2.34~2.96 (6H, m), 3.13 (2H, d, J=5.7 Hz), 3.16~3.35 (2H, m), 3.78 (3H, s). 6.26 (1H, dt, J=5.7 Hz, 15.8 Hz), 6.56 (1H, d, J=15.8 Hz), 6.62~6.98 (4H, m), 7.08~7.48 (6H, m), 7.82 (1H, s)

EXAMPLE 28

(E)-N-[4-((N'-(2-(3-Chloro-4-methoxyphenyl)ethyl)-N'-methyl)amino)butyl]-4-(4-(1H-imidazol-1-yl)phenyl)-3-butenamide

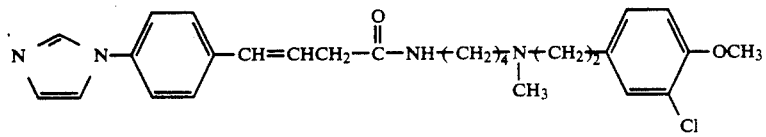

pale yellow oil
NMR (CDCl₃) δ; 1.44~1.68 (4H, m), 2.27 (3H, s), 2.32~2.78 (6H, m), 3.14 (2H, d, J=5.7 Hz), 3.15~3.38 (2H, m), 3.84 (3H, s), 6.30 (1H, dt, J=5.7 Hz, 15.8 Hz), 6.55 (1H, d, J=15.8 Hz), 6.56 (1H, br), 6.81 (1H, d, J=8.4 Hz), 7.02 (1H, dd, J=2.2 Hz, 8.4 Hz), 7.12~7.55 (7H, m), 7.82 (1H, s)

EXAMPLE 29

(E)-N-[3-((N'-(2-(3,4-Dimethoxyphenyl)ethyl)-N'-methyl)amino)propyl]-4-(4-(N²-methylureido)phenyl)-3-butenamide

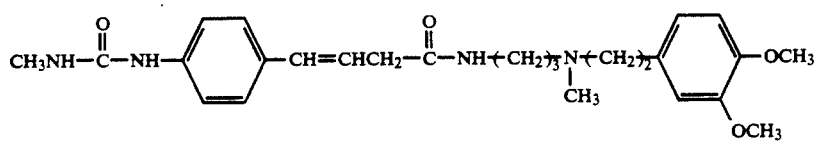

pale yellow oil
NMR (CDCl₃) δ; 1.40~1.84 (2H, m), 2.20 (3H, s), 2.32~2.84 (9H, m), 2.96 (2H, d, J=6.2 Hz), 3.14~3.28 (2H, m), 3.81 (3H, s), 3.83 (3H, s), 5.75~6.14 (2H, m), 6.32 (1H, d, J=15.8 Hz), 6.52~6.81 (3H, m), 7.04 (2H, d, J=8.8 Hz), 7.23 (2H, d, J=8.8 Hz), 7.57 (1H, t, J=5 Hz), 8.06 (1H, s)

EXAMPLE 30

(E)-N-[4-((N'-(2-(3,5-Dimethoxyphenyl)ethyl-N'-methyl)amino)butyl]-4-(4-(N²-methylureido)phenyl)-3-butenamide

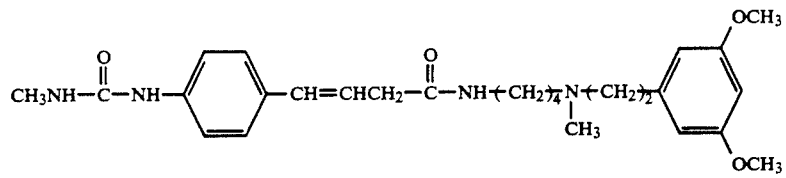

white solid
NMR (CDCl₃) δ; 1.40~1.76 (4H, m), 2.12~2.86 (12H, m), 2.96~3.35 (4H, m), 3.75 (6H, s), 5.76~6.45 (6H, m), 6.78~7.29 (5H, m), 7.92 (1H, s)

EXAMPLE 31

(E)-N-[3-((N'-(2-(3,5-Dimethoxyphenyl)ethyl)-N'-methyl)amino)propyl]-4-(4-(N²-methylthioureido)-phenyl)-3-butenamide

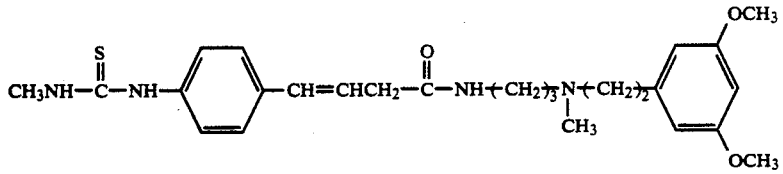

white amorphous product
NMR (CDCl₃) δ; 1.48~1.85 (2H, m), 2.24 (3H, s), 2.38~2.76 (6h, m), 2.99 (2H, d, J=6.2 Hz), 3.09 (3H, d, J=4.4 Hz), 3.18~3.45 (2H, m), 3.83 (6H, s), 5.83~6.51 (3H, m), 6.55~6.83 (3H, m), 7.06~7.38 (5H, m), 8.32 (1H, br s)

EXAMPLE 32

(E)-N-[3-((N'-(2-(3,4-Dimethoxyphenyl)ethyl)-N'-methyl)amino)propyl]-4-[4-((1-methylthio-2-nitroethen-1-yl)amino)phenyl]-3-butenamide

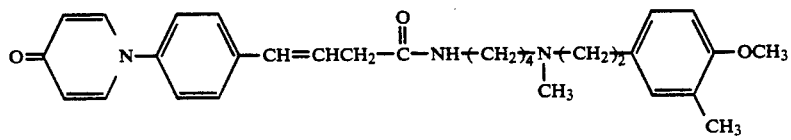

lightly orange-colored amorphous product
NMR (CDCl₃) δ; 1.44~1.80 (2H, m), 2.21 (3H, s), 2.30~3.06 (11H, m), 3.15~3.20 (2H, m), 3.81 (3H, s), 3.82 (3H, s), 6.08 (1H, dt, J=6.2 Hz, 15.8 Hz), 6.39 (1H, d, J=15.8 Hz), 6.40 (1H, br), 6.52~6.80 (4H, m), 7.05 (2H, d, J=8.6 Hz), 7.12~7.36 (3H, m)

EXAMPLE 33

(E)-N-[4-((N'-(2-Phenylethyl)-N'-methyl)amino)butyl]-4-(4-(1,4-dihydro-4-oxo-1-pyridyl)phenyl)-3-butenamide

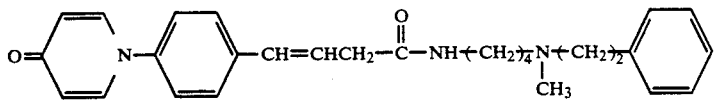

yellow oil
NMR (CDCl₃) δ; 1.43~1.68 (4H, m), 2.08~2.93 (9H, m), 2.96~3.39 (4H, m), 6.07~6.68 (4H, m), 6.89~7.32 (8H, m), 7.36~7.67 (4H, m)

EXAMPLE 34

(E)-N-[4-((N'-(2-(4-Methoxy-3-methylphenyl)ethyl)-N'-methyl)amino)butyl]-4-(4-(1,4-dihydro-4-oxo-1-pyridyl)phenyl)-3-butenamide

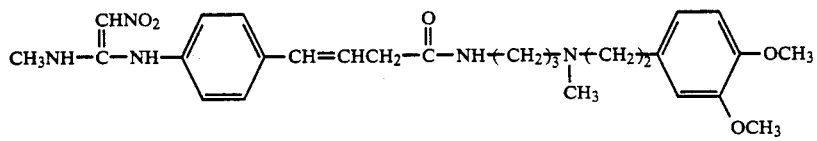

yellow oil
NMR (CDCl₃) δ; 1.48~1.70 (4H, m), 2.18 (3H, s), 2.26~2.80 (9H, m), 3.08~3.40 (4H, m), 3.79 (3H, s), 6.15~6.56 (4H, m), 6.64~7.04 (4H, m), 7.18~7.34 (2H, m), 7.40~7.65 (4H, m)

EXAMPLE 35

(E)-N-[4((N'-(2-(3-Chloro-4-methoxyphenyl)ethyl)-N'-methyl)amino)butyl]-4-(4-(1,4-dihydro-4-oxo-1-pyridyl)phenyl)-3-butenamide

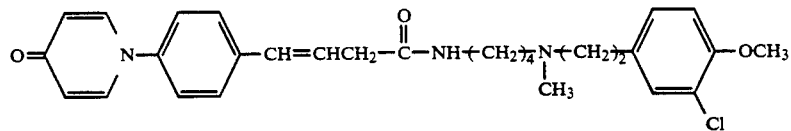

pale yellow oil
NMR (CDCl₃) δ; 1.44~1.68 (4H, m), 2.22~2.88 (9H, m), 3.08~3.39 (4H, m), 3.86 (3H, s), 6.14~6.72 (5H, m), 6.82 (1H, d, J=8.4 Hz), 7.04 (1H, dd, J=1.8 Hz, 8.4 Hz), 7.12~7.26 (3H, m), 7.27~7.66 (4H, m)

EXAMPLE 36

(E)-N-[4-((N'-(2-Phenylethyl)-N'-methyl)amino)butyl]-4-(4-($N^3$-methyl-$N^2$-cyanoguanidino)phenyl)-3-butenamide

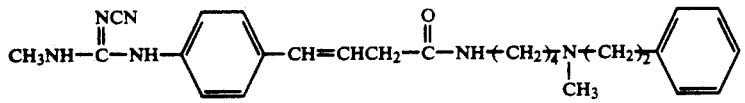

pale yellow oil
NMR (CDCl$_3$) δ; 1.36~1.70 (4H, m), 2.21~2.96 (12H, m), 2.98~3.35 (4H, m), 5.59 (1H, br d, J=5 Hz), 6.15 (1H, dt, J=5.3 Hz, 15.8 Hz), 6.42 (1H, d, J=15.8 Hz), 6.76 (1H, t, J=5.3 Hz), 6.98~7.38 (10H, m)

EXAMPLE 37

(E)-N-[4-((N'-(2-(4-Methoxyphenyl)ethyl)-N'-methyl)amino)butyl]-4-(4-($N^3$-methyl-$N^2$-cyanoguanidino)phenyl)-3-butenamide

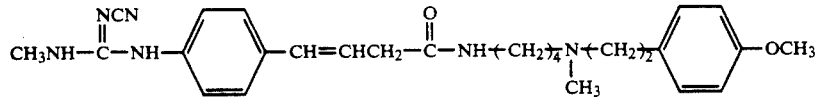

pale yellow amorphous product

NMR (CDCl$_3$) δ; 1.42~1.70 (4H, m), 2.22~2.92 (12H, m), 2.98~3.34 (4H, m), 3.75 (3H, s), 5.57 (1H, br d, J=6 Hz), 6.18 (1H, dt, J=5.7 Hz, 15.8 Hz), 6.43 (1H, d, J=15.8 Hz), 6.65~6.82 (3H, m), 6.99~7.38 (7H, m)

EXAMPLE 38

(E)-N-[4-((N'-(2-(3-Methoxyphenyl)ethyl)-N'-methyl)amino)butyl]-4-(4-($N^3$-methyl-$N^2$-cyanoguanidino)phenyl-3-butenamide

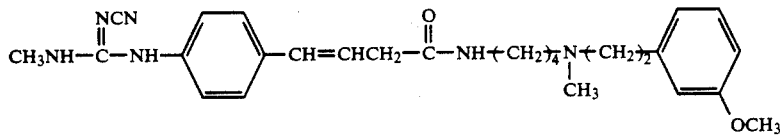

pale yellow amorphous product
NMR (CDCl$_3$) δ; 1.36~1.64 (4H, m), 2.16~2.92 (12H, m), 2.98~3.33 (4H, m), 3.76 (3H, s), 5.02 (1H, br d, J=6 Hz), 6.14 (1H, dt, J=5.3 Hz, 15.8 Hz), 6.42 (1H, d, J=15.8 Hz), 6.62~6.91 (4H, m), 7.03~7.36 (6H, m)

EXAMPLE 39

(E)-N-[4-((N'-(2-(4-Chlorophenyl)ethyl)-N'-methyl)amino)butyl]-4-(4-($N^3$-methyl-$N^2$-cyanoguanidino)-phenyl)-3-butenamide

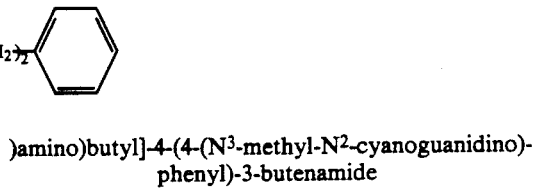

pale yellow amorphous product
NMR (CDCl$_3$) δ; 1.38~1.64 (4H, m), 2.15~2.82 (11H, m), 2.98~3.32 (4H, m), 5.47 (1H, br d, J=6 Hz), 6.18 (1H, dt, J=5.7 Hz, 15.8 Hz), 6.45 (1H, d, J=15.8 Hz), 6.54 (1H, t, J=5.7 Hz), 6.98~7.44 (9H, m)

EXAMPLE 40

(E)-N-[4-((N'-(2-(3,4-Dichlorophenyl)ethyl)-N'-methyl)amino)butyl]-4-(4-($N^3$-methyl-$N^2$-cyanoguanidino)phenyl)-3-butenamide

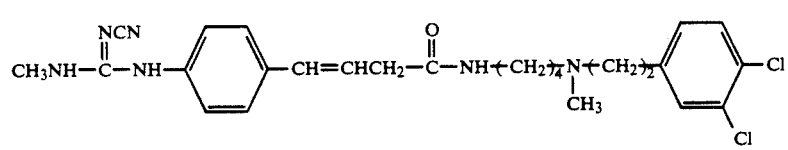

pale yellow amophour product
NMR (CDCl$_3$) δ; 1.40~1.62 (4H, m), 2.10~2.76 (9H, m), 2.85 (3H, d, J=4.4 Hz), 3.02~3.36 (4H, m), 5.34 (1H, br d, J=6 Hz), 6.20 (1H, dt, J=6.2 Hz, 16.0 Hz), 6.40 (1H, br), 6.46 (1H, d, J=16.0 Hz), 6.92~7.42 (10H, m)

EXAMPLE 41

(E)-N-[4-((N'-(2-(4-Methylphenyl)ethyl)-N'-methyl-)amino)butyl]-4-(4-(N³-methyl-N²-cyanoguanidino)-phenyl)-3-butenamide

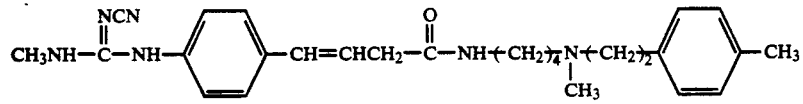

yellow oil
NMR (CDCl₃) δ; 1.39~1.65 (4H, m), 2.04~2.95 (15H, m), 2.98~3.32 (4H, m), 5.80 (1H, br d, J=5.8 Hz), 6.18 (1H, dt, J=5.7 Hz, 15.8 Hz), 6.43 (1H, d, J=15.8 Hz), 6.88~7.40 (10H, m)

EXAMPLE 42

(E)-N-[3-((N'-(2-(3,4-Dimethoxyphenyl)ethyl)-N'-methyl)amino)propyl]-4-(4-(1,4-dihydro-4-oxopyrimidin-2-yl)phenyl)-3-butenamide

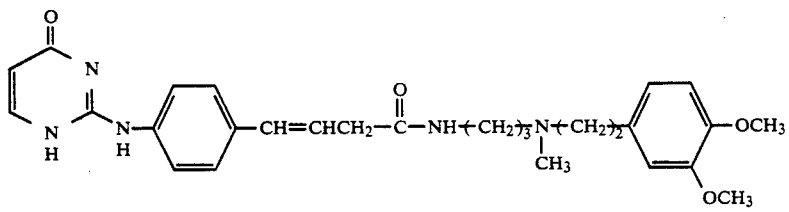

white amorphous product
NMR (CDCl₃) δ; 1.55~1.86 (2H, m), 2.26 (3H, s), 2.42~2.79 (6H, m), 2.96 (2H, d, J=6.2 Hz), 3.22~3.41 (4H, m), 3.81 (3H, s), 3.82 (3H, s), 5.85 (1H, d, J=6.6 Hz), 6.07 (1H, dt, J=6.2 Hz, 15.8 Hz), 6.36 (1H, d, J=15.8 Hz), 6.58~6.84 (3H, m), 7.08~7.28 (2H, m), 7.32~7.72 (4H, m)

EXAMPLE 43

(E)-N-[4-((N'-(2-(3,5-Dimethoxyphenyl)ethyl)-N'-methyl)amino)butyl]-4-(4-(1,4-dihydro-4-oxopyrimidin-2-yl)phenyl)-3-butenamide

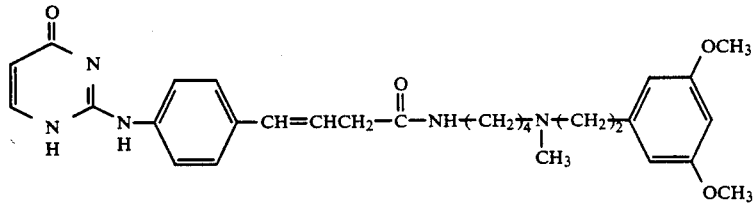

NMR (CDCl₃) δ; 1.35~1.55 (4H, m), 2.24 (3H, s), 2.36 (2H, m), 2.54~2.61 (2H, m), 2.63~2.71 (2H, m), 2.98 (2H, d, J=6.2 Hz), 3.13~3.22 (2H, m), 3.74 (6H, s), 5.74 (1H, d, J=6 Hz), 6.02 (1H, dt, J=6.2 Hz, 15.8 Hz), 6.22~6.39 (4H, m), 6.98 (1H, br), 7.09 (2H, d, J=8.4 Hz), 7.26 (1H, br), 7.36 (2H, d, J=8.4 Hz), 7.57 (1H, d, J=8.6 Hz)

EXAMPLE 44

(E)-N-[4-((N'-(2-(3,4-Dimethoxyphenyl)ethyl)-N'-methyl)amino)butyl]-4-(4-(1H-imidazol-1-yl)thiophen-2-yl)-3-butenamide

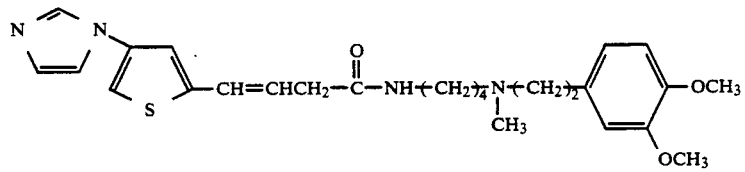

yellow oil
NMR (CDCl₃) δ; 1.4~1.7 (4H, m), 2.31 (3H, s), 2.3~2.8 (6H, m), 3.10 (2H, d, J=6.5 Hz), 3.2~3.4 (2H, m), 3.83 (3H, s), 3.85 (3H, s), 6.14 (1H, dt, J=16.0 Hz, 6.5 Hz), 6.54 (1H, d, J=16.0 Hz), 6.7~6.9 (3H, m), 6.97 (2H, bs), 7.12 (1H, bs), 7.19 (1H, bs), 7.5 (1H, m), 7.8 (1H, bs)

EXAMPLE 45

(E)-N-[4-((N'-(2-(3,5-Dimethoxyphenyl)ethyl)-N'-methyl)amino)butyl]-4-(4-(1H-imidazolyl-1-yl)thiophen-2-yl)-3-butenamide

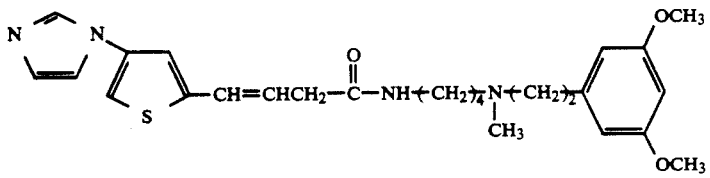

NMR (CDCl$_3$) δ; 1.55~1.50 (4H, m), 2.26 (3H, s), 2.37~2.41 (2H, m), 2.57~2.61 (2H, m), 2.68~2.72 (2H, m), 3.07 (2H, dd, J=7.0 Hz, 1.5 Hz), 3.21~3.26 (2H, m), 3.75 (6H, s), 6.23 (1H, dt, J=15.5 Hz, 7.0 Hz), 6.29~6.30 (1H, m), 6.32~6.33 (2H, m), 6.55 (1H, dt, J=15.5 Hz, 1.5 Hz), 6.56 (1H, m), 6.96 (2H, m), 7.13 (1H, m), 7.18 (1H, m), 7.76 (1H, m)

EXAMPLE 46

(E)-N-[4-((N'-(2-(3,4-Dimethoxyphenyl)ethyl)-N'-methyl)amino)butyl]-4-(2-(1H-imidazol-1-yl)thiophen-5-yl)-3-butenamide

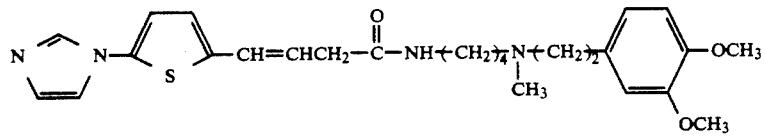

yellow oil
NMR (CDCl$_3$) δ; 1.5~1.7 (4H, m), 2.31 (3H, s), 2.3~2.6 (2H, m), 2.6~2.8 (4H, m), 3.08 (2H, d, J=7.0 Hz), 3.1~3.5 (2H, m), 3.84 (3H, s), 3.86 (3H, s), 6.11 (1H, dt, J=15.5 Hz, 7.0 Hz), 6.50 (1H, d, J=15.5 Hz), 6.6 (1H, m), 6.7~6.9 (5H, m), 7.15 (2H, m), 7.71 (1H, m)

EXAMPLE 47

(E)-N-[4-((N'-(2-(3,4-Dimethoxyphenyl)ethyl)-N-methyl)amino)butyl]-4-(4-(4-pyridyl)phenyl)-3-butenamide

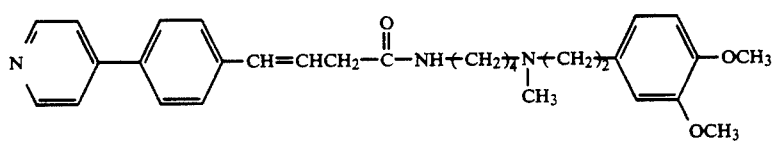

pale yellow oil
NMR (CDCl$_3$) δ; 1.4~1.7 (4H, m), 2.28 (3H, s), 2.3~2.9 (6H, m), 3.15 (2H, d, J=6.0 Hz), 3.2~3.4 (2H, m), 3.83 (3H, s), 3.85 (3H, s), 6.3~6.9 (6H, m), 7.3~7.7 (6H, m), 8.5~8.7 (2H, m)

EXAMPLE 48

(E)-[N-(4-((N'-(2-(3,4-Dimethoxyphenyl)ethyl)-N'-methyl)amino)butyl]-4-(4-(3-pyridyl)phenyl)-3-butenamide

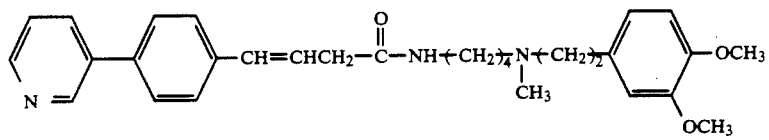

pale yellow oil
NMR (CDCl$_3$) δ; 1.5~1.7 (4H, m), 2.35 (3H, s), 2.4~2.6 (2H, m), 2.6~2.9 (4H, m), 3.16 (1H, d, J= 6.0 Hz), 3.2~3.4 (2H, m), 3.83 (3H, s), 3.85 (3H, s), 6.40 (1H, dt, J=16.0 Hz, 6.0 Hz), 6.50 (1H, d, J=16.0 Hz), 6.6 (1H, m), 6.7~6.9 (3H, m), 7.2~7.6 (5H, m), 7.7~7.9 (1H, m), 8.54 (1H, dd, J=5.0 Hz, 1.0 Hz), 8.8 (1H, m)

EXAMPLE 49

(E)-[N-(4-((N'-(2-(3,5-Dimethoxyphenyl)ethyl)-N'-methyl)amino)butyl]-4-(4-(3-pyridyl)phenyl)-3-butenamide

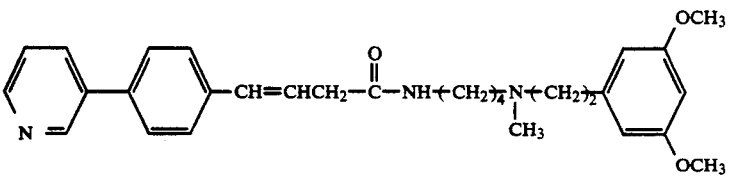

pale yellow oil
NMR (CDCl$_3$) δ; 1.4~1.7 (4H, m), 2.28 (3H, s), 2.3~2.6 (2H, m), 2.6~2.8 (4H, m), 3.14 (2H, d, J=6 Hz), 3.16~3.4 (2H, m), 3.76 (6H, s), 6.24-6.52 (6H, m), 7.28~7.6 (5H, m), 7.76~7.92 (1H, m), 8.56 (1H, dd, J=5 Hz, 1 Hz), 8.82 (1H, d, J=1 Hz)

EXAMPLE 50

(E)-N-[4-((N'-(2-(4-Nitrophenyl)ethyl)-N'-methyl)amino)butyl]-4-(4-(1H-imidazol-1-yl)phenyl)-3-butenamide

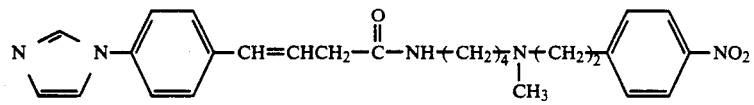

lightly red oil
NMR (CDCl$_3$) δ; 1.4~1.7 (4H, m), 2.32 (3H, s), 2.3~3.0 (6H, m), 3.1~3.4 (4H, m), 5.96~6.2 (1H, broad), 6.2~6.7 (2H, m), 7.16~7.56 (8H, m), 7.84 (1H, s), 8.08 (1H, s), 8.18 (1H, s)

EXAMPLE 51

(E)-N-[4-((N'-(2-(3,4-Dimethoxyphenyl)ethyl)-N'-methyl)amino)propyl]-4-[4-((1-methylimidzolin-4-on-2-yl)amino)phenyl]-3-butenamide

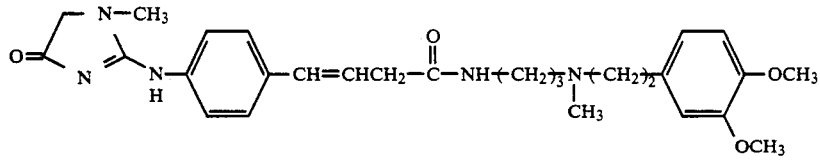

yellow oil
NMR (CDCl$_3$) δ; 1.50~1.85 (2H, m), 2.10 (3H, s), 2.30~2.80 (6H, m), 3.25 (2H, d, J=4 Hz), 3.28 (3H, s), 3.76 (5H, s), 3.79 (3H, s), 5.96~7.58 (8H, m)

EXAMPLE 52

(E)-N-[4-((N'-(2-(3,4-Dimethoxyphenyl)ethyl)-N'-methyl)amino)butyl]-4-[4-((imidazolin-4-on-2-yl)amino)phenyl]-3-butenamide

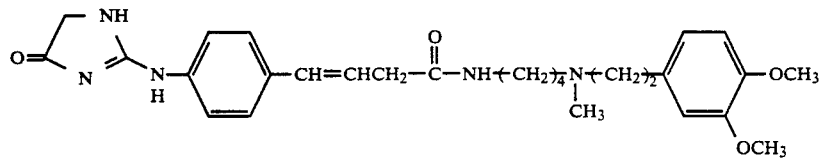

white wax
NMR (CDCl$_3$) δ; 1.48~1.84 (2H, m), 2.11 (3H, s), 2.30~2.79 (6H, m), 3.25 (2H, d, J=4 Hz), 3.76 (5H, s), 3.79 (3H, s), 5.97~7.58 (9H, m)

PRODUCTION EXAMPLE 36

5-(1H-Imidazol-1-yl)furfural

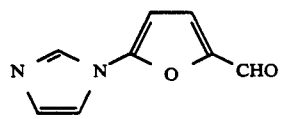

14.17 g of 5-bromofurfural and 6.62 g of imidazole were dissolved in 80 m( of N-methylpyrrolidone. 13.43 g of anhydrous potassium carbonate was added to the solution and the solution was stirred at 100° C. in a nitrogen atmosphere for 9 h.

After leaving the reaction mixture to cool, water was added thereto. The product was extracted with ethyl acetate and washed with water and then with a saturated aqueous common salt solution.

After drying over anhydrous magnesium sulfate, the solvent was distilled off under reduced pressure. The product was purified according to silica gel column chromatography (solvent: dichloromethane/methanol =30/1). The resulting solid was washed with ether to give 1.21 g of the intended compound in the form of a light orange solid (yield: 9%).

NMR (CDCl$_3$, 400 MHz) δ; 6.38 (1H, d, J=3.6 Hz), 7.23 (1H, dd, J=0.8 Hz, 1.2 Hz), 7.34 (1H, d, J=3.6 Hz), 7.41 (1H, dd, J=0.4 Hz, 1.2 Hz), 8.05 (1H, dd, J=0.4 Hz, 0.8 Hz), 9.60 (1H, s)

PRODUCTION EXAMPLE 37

5-(1H-Imidazol-1-yl)-3-methyl-2-thiophenecarboxaldehyde

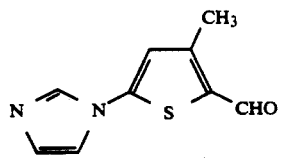

26 g of 3-methyl-2-thiophenecarboxaldehyde was dissolved in 100 ml of chloroform and the solution was stirred by cooling with ice. 11 ml of bromine was added dropwise thereto. The temperature was elevated to room temperature and the mixture was stirred overnight. About 1 l of ethyl acetate was added thereto and the mixture was washed with water, then with a saturated aqueous sodium hydrogencarbonate solution and finally with a saturated aqueous common salt solution. After drying over anhydrous magnesium sulfate, the solvent was distilled off under reduced pressure to give 46.8 g of 5-bromo-3-methyl-2-thiophenecarboxaldehyde in the form of a dark brown solid, which was subjected to the subsequent reaction without purification.

46.8 g of 5-bromo-3-methyl-2-thiophenecarboxaldehyde, 93 g of imidazole and 3 g of copper powder were suspended in 230 ml of water. The suspension was heated under reflux in a nitrogen stream for 12 h. Aqueous ammonia was added thereto and the product was extracted with chloroform thrice and dried over anhydrous magnesium sulfate. Then the solvent was distilled off under reduced pressure. Ethyl acetate was added to the residue. After extraction with dilute hydrochloric acid thrice, the aqueous layer was made alkaline with aqueous ammonia. The product was extracted with chloroform thrice and dried over anhydrous magnesium sulfate. The solvent was distilled off under reduced pressure. The product was purified according to silica gel column chromatography to give 15.9 g of the intended compound in the form of a dark brown solid (yield: 36%).

NMR (CDCl₃, 400 MHz) δ; 2.60 (3H, s), 6.88 (1H, s), 7.21 (1H, m), 7.26 (1h, t, J=1.5 Hz), 7.86 (1H, m), 10.02 (1H, s)

PRODUCTION EXAMPLE 38

5-Bromo-2-thiophenecarboxaldehyde dimethyl acetal

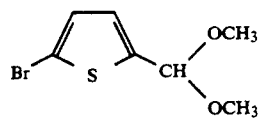

50 g of 5-bromo-2-thiophenecarboxaldehyde was dissolved in 200 ml of methylene chloride. A suspension of 50 g of montmorillonite K-10 in about 50 ml of trimethyl o-formate was added to the solution and the solution was stirred at room temperature for about 30 min. Montmorillonite K-10 was filtered off and the methylene chloride layer was washed with a saturated aqueous sodium hydrogencarbonate solution and then with a saturated aqueous common salt solution. After drying over anhydrous magnesium sulfate, the solvent was distilled off under reduced pressure.

The residue was distilled under reduced pressure to give 55.9 g of the intended compound in the form of a light yellow oil.

NMR (CDCl₃, 400 MHz) δ; 3.35 (6H, s), 5.54 (1H, s), 6.82 (1H, d, J=3.5 Hz), 6.95 (1H, d, J=3.5 Hz)

PRODUCTION EXAMPLE 39

5-(3-Pyridyl)thiophene-2-carboxaldehyde

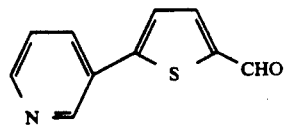

50 ml of anhydrous tetrahydrofuran and a catalytic amount of iodine were added to 3.3 g of magnesium in a nitrogen stream and the resulting solution was stirred. 20 g of 5-bromo-2-thiophenecarboxaldehyde dimethyl acetal was dissolved in 100 ml of anhydrous tetrahydrofuran and the solution was slowly dropped into the mixture prepared as described above so that the temperature would be kept at 30° to 50° C.

The Grignard reagent thus prepared was added to a solution of 10 ml of 3-bromopyridine and 1.0 g of bis(1,3-diphenylphosphinopropane)nickel (II) chloride in anhydrous tetrahydrofuran. The resulting solution was stirred at room temperature for 30 min and then heated under reflux for 2 h. Diluted hydrochloric acid was added to the solution to make it acidic and the solution was stirred at room temperature for 30 min. Ethyl acetate was added thereto and the product was extracted with diluted hydrochloric acid twice. Concentrated aqueous ammonia was added to the resultant aqueous layer to make it alkaline. After extraction with methylene chloride thrice, the organic layer was dried over anhydrous magnesium sulfate and the solvent was distilled off under reduced pressure.

The residue was purified according to silica gel column chromatography to give 7.4 g of the intended compound in the form of a dark brown solid (yield: 43%).

NMR (CDCl₃, 400 MHz) δ; 7.40 (1H, ddd, J=8.0 Hz, 5.0 Hz, <1.0 Hz), 7.47 (1H, d, J=4.0 Hz), 7.79 (1H, d, J=4.0 Hz), 7.95 (1H, ddd, J=8.0 Hz, 1.5 Hz, <1.0 Hz), 8.64 (1H, dd, J=5.0 Hz, 1.5 Hz), 8.96 (1H, dd, J=1.5 Hz, <1.0 Hz), 9.94 (1H, s)

4-(2-Methoxy-5-pyridyl)benzaldehyde

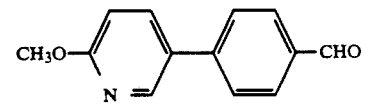

white acicular crystals (yield: 68%).

NMR (CDCl₃, 400 MHz) δ; 4.06 (3H, s), 6.77 (1H, d, J=8.0 Hz), 7.43 (1H, dd, J=7.5 Hz, <1.0 Hz), 7.67 (1H, dd, J=8.0 Hz, 7.5 Hz), 7.97 (2H, ddd, J=8.5 Hz, 2.0 Hz, 1.5 Hz), 8.22 (2H, ddd, J=8.5 Hz, 2.0 Hz, 1.5 Hz), 10.07 (1H, s)

PRODUCTION EXAMPLE 40

(E)-4-((5-(1H-Imidazol-1-yl)furan-2-yl)-3-butenoic acid

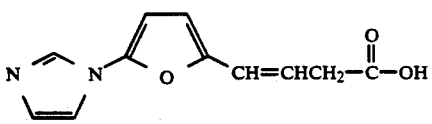

1.21 g of 5-(1H-imidazol-1-yl)furfural and 3.05 g of β-carboxyethyltriphenylphosphonium chloride were added to 15 ml of tetrahydrofuran and the mixture was cooled to −60° C. 10 ml of a solution of 1.84 g of potassium tert-butoxide in tetrahydrofuran was slowly dropped thereinto under stirring and then the temperature was slowly elevated to room temperature. Two hours after, water was added thereto and the mixture was concentrated under reduced pressure. Water and active carbon were added to the residue and the mixture was filtered. The aqueous layer was washed with ether. Concentrated hydrochloric acid was added to the aqueous layer to adjust its pH to about 4 and a precipitate thus formed was recovered by filtration. It was washed with water, acetone and ether successively to give 0.96 g of the intended compound in the form of a light brown solid (yield: 59%).

NMR (DMSO-d$_6$, 400 MHz) δ; 3.20 (2H, d, J=7.2 Hz), 6.19 (1H, dt, J=7.2 Hz, 15.6 Hz), 6.38 (1H, d, J=15.6 Hz), 6.51 (1H, d, J=3.6 Hz), 6.54 (1H, d, J=3.6 Hz), 7.11 (1H, dd, J=0.8 Hz, 1.6 Hz), 7.66 (1H, dd, J=1.2 Hz, 1.6 Hz), 8.18 (1H, dd, J=0.8 Hz, 1.2 Hz)

The following compounds were produced in the same manner as that described above:

(E)-4-(5-(1H-imidazol-1-yl)-3-methylthiophen-2-yl)-3-butenoic acid

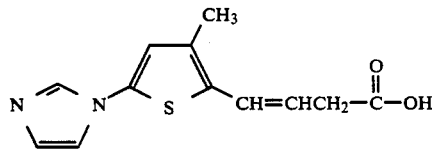

light yellow solid

NMR (DMSO-d$_6$, 400 MHz) δ; 2.19 (3H, s), 3.21 (2H, dd, J=7.0 Hz, 1.5 Hz), 5.91 (1H, dt, J'15.0 Hz, 7.0 Hz), 6.72 (1H, dt, J=15.0 Hz, 1.5 Hz), 7.05 (1H, s), 7.09 (1H, dd, J=1.5 Hz, <1.0 Hz), 7.58 (1H, dd, J=1.5 Hz, 1.5 Hz), 8.05 (1H, dd, J=1.5 Hz, <1.0 Hz), and (E)-4-(5-(3-pyridyl)thiophen-2-yl)-3-butenoic acid

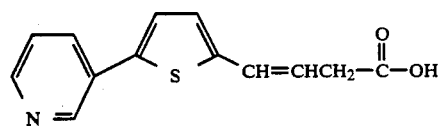

dark brown solid (yield: 75%)

NMR (DMSO-d$_6$, 400 MHz) δ; 3.18 (2H, d, J=7.0 Hz), 8.09 (1H, dt, J=16.0 Hz, 7.0 Hz), 6.67 (1H, d, J=16.0 Hz), 7.08 (1H, d, J=4.0 Hz), 7.42 (1H, ddd, J=8.0 Hz, 4.5 Hz, <1.0 Hz), 7.53 (1H, d, J=4.0 Hz), 8.01 (1H, ddd, J=8.0 Hz, 2.0 Hz, <1.0 Hz), 8.47 (1H, dd, J=5.0 Hz, 1.5 Hz), 8.86 (1H, d, J=2.0 Hz)

PRODUCTION EXAMPLE 41

5-(1,4-Dihydro-4-oxo-1-pyridyl)thiophene-2-carboxaldehyde

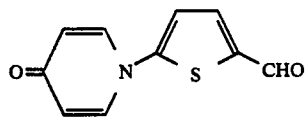

25.0 g of 4-hydroxypyridine was suspended in 440 ml of N,N-dimethylformamide. 11.04 g of sodium hydride (60% suspension in mineral oil) was added to the suspension in portions and the suspension was stirred for 1 h. 32.8 ml of 5-bromothiophene-2-carboxaldehyde was added thereto and a reaction was conducted at 120° C. for 4 h.

The reaction mixture was left to cool and concentrated under reduced pressure. Water was added thereto and an insoluble matter was filtered off. The product was washed with water, acetone and ether successively to give 26.86 g of the intended compound in the form of a light yellow powder (yield: 50%).

NMR (CDCl$_3$, 400 MHz) δ; 6.50 (2H, m), 7.08 (1, d, J=4.4 Hz), 7.65 (2H, m), 7.70 (1H, d, J=4.4 Hz), 9.88 (1H, s)

PRODUCTION EXAMPLE 42

(E)-4-((5-(1,4-Dihydro-4-oxo-1-pyridyl)thiophen-2-yl)-3-butenoic acid

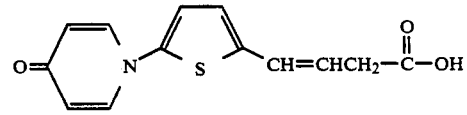

26.86 g of 5-(1,4-dihydro-4-oxo-1-pyridyl)thiophene-2-carboxaldehyde and 51.01 g of β-carboxyethyltriphenylphosphonium chloride were suspended in 250 ml of tetrahydrofuran and the suspension was cooled to −50° C. 200 ml of a solution of 30.88 g of potassium tert-butoxide in tetrahydrofuran was slowly dropped thereinto. After the completion of the addition, the temperature was slowly elevated to room temperature.

Two hours after, water was added thereto and the aqueous layer was washed with ether. Concentrated hydrochloric acid was added thereto to adjust the pH to 3. The product was extracted with chloroform/methanol (3/1) and dried over anhydrous magnesium sulfate. The solvent was distilled off under reduced pressure.

600 ml of methanol and 3 ml of concentrated sulfuric acid were added to the residue and heated under reflux for 4 h. The mixture was concentrated under reduced pressure and an aqueous potassium carbonate solution was added thereto. The product was extracted with ethyl acetate, washed with water and a saturated aqueous common salt solution and dried over anhydrous magnesium sulfate. The solvent was distilled off.

The product was purified according to silica gel column chromatography (solvent: dichlormethane/methanol =50/1) to give 9.12 g of methyl ester of the intended compound in the form of a dark pink solid (yield: 25%).

NMR (CDCl$_3$, 400 MHz) δ; 3.25 (2H, d, J=7.2 Hz), 3.73 (3H, s), 6.13 (1H, dt, J=7.2 Hz, 15.6 Hz), 6.44 (2H, m), 6.54 (1H, d, J=15.6 Hz), 6.80 (1H, d, J=3.6 Hz), 6.84 (1H, d, J=3.6 Hz), 7.55 (2H, m)

8.49 g of the methyl ester thus produced was dissolved in 60 ml of methanol. 34 ml of a 1N-aqueous sodium hydroxide solution was added thereto and stirred at room temperature for 8 h. The reaction mixture was concentrated under reduced pressure. Water was added thereto and the aqueous layer was washed with ether. The pH of the solution was adjusted to 2 with concentrated hydrochloric acid and a precipitate thus formed was recovered by filtration. It was washed with water and dried to give 7.48 g of the intended compound in the form of a light orangy yellow powder (yield: 93%).

NMR (DMSO-d$_6$, 400 MHz) δ; 3.20 (2H, d, J=7.2 Hz), 6.05 (1H, dt, J=7.2 Hz, 15.6 Hz), 6.22 (2H, m), 6.65 (1H, d, J=15.6 Hz), 6.99 (1H, d, J=4 Hz), 7.17 (1H, d, J=4 Hz), 7.96 (2H, m)

PRODUCTION EXAMPLE 43

Ethyl (E)-4-(4-(N-oxy-4-pyridyl)phenyl)-3-butenoate

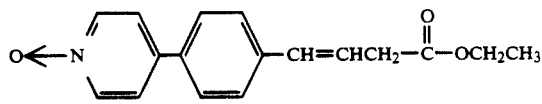

0.70 g of (E)-4-(4-pyridylphenyl)-3-butenoic acid was suspended in 30 ml of ethanol. About 0.5 ml of concentrated sulfuric acid was added thereto and the resulting solution was heated under reflux for 1 h. Ethanol was distilled off under reduced pressure and ethyl acetate was added to the residue. After washing with diluted aqueous ammonia, water and a saturated aqueous common salt solution successively followed by drying over anhydrous magnesium sulfate, the solvent was distilled off under reduced pressure to give 0.70 g of the crude ethyl ester in the form of a light yellow oil, which was then subjected to the subsequent reaction without purification.

0.70 g of the crude ethyl ester was dissolved in 100 ml of methylene chloride. 0.64 g of m-chloroperbenzoic acid was added thereto and stirred overnight. Ethyl acetate was added thereto and the reaction mixture was washed with an aqueous sodium hydrogensulfite solution and a saturated aqueous common salt solution. After drying over anhydrous magnesium sulfate, the solvent was distilled off under reduced pressure. The product was purified according to silica gel column chromatography to give 0.67 g of the intended compound in the form of a light yellow oil (yield: 63%).

NMR (CDCl$_3$, 400 MHz) δ; 1.30 (3H, t, J=7.0 Hz), 3.28 (2H, dd, J=7.0 Hz, <1.0 Hz), 4.19 (2H, q, J=7.0 Hz), 6.40 (1H, dt, J=16.0 Hz, 7.0 Hz), 6.50 (1H, d, J=16.0 Hz), 7.5~7.6 (6H, m), 8.25 (2H, m)

The following compound was obtained in the same manner as that described above:

Ethyl (E)-4-(4-(N-oxy-3-pyridyl)phenyl)-3-butenoate

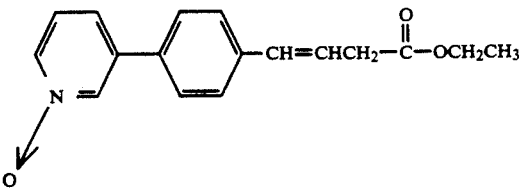

white solid

NMR (CDCl$_3$, 400 MHz) δ; 1.30 (3H, t, J=7.0 Hz), 3.28 (2H, dd, J=7.5 Hz, 1.0 Hz), 4.20 (2H, q, J=7.0 Hz), 6.41 (1H, dt, J=16.0 Hz, 7.5 Hz), 6.53 (1H, dt, J=7.5 Hz, 1.0 Hz), 7.31~7.37 (1H, m), 7.4~7.56 (5H, m), 8.18~8.20 (1H, m), 8.47~8.49 (1H, m)

PRODUCTION EXAMPLE 44

Methyl (E)-4-(4-(N$^2$-ethylthioureido)phenyl)-3-butenoate

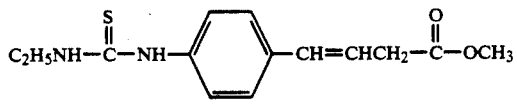

2.00 g of methyl (E)-4-(4-aminophenyl)-3-butenoate was dissolved in 20 ml of dioxane. 1.1 ml of ethyl isothiocyanate was added to the solution and a reaction was conducted at 100° C. for 10 h. The solvent was distilled off and benzene was added to the residue. An insoluble matter was filtered off and the residue was concentrated again.

The product was purified according to silica gel column chromatography (solvent: n-hexane/ethyl acetate=2/1) to give 1.65 g of the intended compound in the form of a light yellow solid (yield: 57%).

m.p. (°C.): 88 to 89 (recrystallized from n-hexane/ethyl acetate)

EMA for C$_{14}$H$_{18}$N$_2$O$_2$S:

|  | C | H | N | S |
|---|---|---|---|---|
| calcd (%) | 60.41 | 6.52 | 10.06 | 11.52 |
| found (%) | 60.45 | 6.48 | 10.03 | 11.57 |

NMR (CDCl$_3$, 400 MHz) δ; 1.19 (3H, t, J=7.2 Hz), 3.27 (2H, d, J=6.8 Hz), 3.67 (2H, m), 3.73 (3H, s), 5.95 (1H, br), 6.31 (1H, dt, J=6.8 Hz, 16 Hz), 6.48 (1H, d, J=16 Hz), 7.14 (2H, d, J=8.4 Hz), 7.42 (2H, d, J=8.4 Hz), 7.64 (1H, br s)

The following compound was produced in the same manner as that described above:

Methyl (E)-4-(4-(N$^2$-n-propylthioureido)phenyl)-3-butenoate

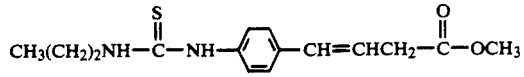

light yellow solid (yield: 69%)

m.p. (°C.): 76.5 to 78 (recrystallized from n-hexane/ethyl acetate)

EMA for C$_{15}$H$_{20}$N$_2$O$_2$S:

|  | C | H | N | S |
|---|---|---|---|---|
| calcd (%) | 61.61 | 6.89 | 9.58 | 10.97 |
| found (%) | 61.66 | 6.80 | 9.67 | 10.86 |

NMR (CDCl$_3$, 400 MHz) δ; 0.92 (3H, t, J=7.2 Hz), 1.60 (2H, sextet, J=7.2 Hz), 3.27 (2H, d, J=6.8 Hz), 3.60 (2H, q, J=7.2 Hz), 3.73 (3H, s), 6.00 (1H, br), 6.32 (1H, dt, J=6.8 Hz, 15.6 Hz), 6.48 (1H, d, J=15.6 Hz), 7.14 (2H, d, J=8.4 Hz), 7.43 (2H, d, J=8.4 Hz), 7.61 (1H, s)

PRODUCTION EXAMPLE 45

Methyl (E)-4-(4-N$^2$-isopropylthioureido)phenyl)-3-butenoate $$\text{(CH}_3)_2\text{CH-NH-C(=S)-NH-C}_6\text{H}_4\text{-CH=CHCH}_2\text{-C(=O)-OCH}_3$$

2.00 g of (E)-4-(4-aminophenyl)-3-butenoate and 3.21 ml of triethylamine were dissolved in 35 ml of chloroform and the solution was stirred under cooling with ice. 0.88 ml of thiophosgene was dropped thereinto and the mixture was heated under reflux for 30 min. The reaction mixture was cooled again with ice. 0.98 ml of isopropylamine was dropped thereinto and the mixture was heated under reflux for 30 min. After leaving to cool, 1N hydrochloric acid was added thereto. The product was extracted with chloroform and dried over anhydrous magnesium sulfate. The solvent was distilled off. The product was purified according to silica gel column chromatography (solvent: n-hexane/ethyl acetate=3/1) to give 1.75 g of the intended compound in the form of a yellow powder (yield: 57%).

m.p. (°C.): 123 to 124.5 (recrystallized from n-hexane/ethyl acetate)

EMA for C$_{15}$H$_{20}$N$_2$O$_2$S:

|  | C | H | N | S |
|---|---|---|---|---|
| calcd (%) | 61.61 | 6.89 | 9.58 | 10.97 |
| found (%) | 61.53 | 6.83 | 9.60 | 10.95 |

NMR (CDCl$_3$, 400 MHz) δ; 1.21 (6H, d, J=6.4 Hz), 3.27 (2H, d, J=7.2 Hz), 3.73 (3H, s), 4.58 (1H, m), 5.79 (1H, d, J=8.8 Hz), 6.32 (1H, dt, J=7.2 Hz, 15.6 Hz), 6.49 (1H, d, J=15.6 Hz), 7.13 (2H, d, J=8.4 Hz), 7.42 (2H, d, J=8.4 Hz), 7.68 (1H, s)

PRODUCTION EXAMPLE 46

Methyl (E)-4-(4-(N$^3$-ethyl-N$^2$-cyanoguanidino)phenyl)-3-butenoate $$\text{C}_2\text{H}_5\text{NH-C(=NCN)-NH-C}_6\text{H}_4\text{-CH=CHCH}_2\text{-C(=O)-OCH}_3$$

1.45 g of methyl (E)-4-(4-(N$^2$-ethylthioureido)phenyl)-3-butenoate was dissolved in 10 ml of 1,4-dioxane. 1.61 g of N,N-dicyclohexylcarbodiimide, 0.33 g of cyanamide and a catalytic amount of diisopropylethylamine were added to the solution and stirred at 100° C. for 2 h. The reaction mixture was concentrated and purified according to silica gel column chromatography (solvent: n-hexane/ethyl acetate=2/3) to give 1.40 g of the intended compound in the form of a white powder (yield: 94%).

m.p. (°C.): 134 to 135.5 (recrystallized from n-hexane/ethyl acetate)

EMA for C$_{15}$H$_{18}$N$_4$O$_2$:

|  | C | H | N |
|---|---|---|---|
| calcd (%) | 62.92 | 6.34 | 19.57 |
| found (%) | 62.63 | 6.33 | 19.25 |

NMR (CDCl$_3$, 400 MHz) δ; 1.14 (3H, t, J=7.2 Hz), 3.28 (2H, d, J=7.2 Hz), 3.33 (2H, dq, J=5.6 Hz, 7.2 Hz), 4.79 (1H, br), 6.33 (1H, dt, J=7.2 Hz, 16 Hz), 6.49 (1H, d, J=16 Hz), 7.15 (1H, br s), 7.17 (2H, d, J=8.4 Hz), 7.43 (2H, d, J=8.4 Hz)

The following compounds were produced in the same manner as that described above:

Methyl (E)-4-(4-(N$^3$-n-propyl-N$^2$-cyanoguanidino)phenyl)-3-butenoate $$\text{CH}_3\text{CH}_2\text{CH}_2\text{NH-C(=NCN)-NH-C}_6\text{H}_4\text{-CH=CHCH}_2\text{-C(=O)-OCH}_3$$

faint yellow solid (yield: 60%)

m.p. (°C.): 105.5 to 107 (recrystallized from n-hexane/ethyl acetate)

EMA for C$_{16}$H$_{20}$N$_4$O$_2$:

|  | C | H | N |
|---|---|---|---|
| calcd (%) | 63.98 | 6.71 | 18.65 |
| found (%) | 63.89 | 6.64 | 18.49 |

NMR (CDCl$_3$, 400 MHz) δ; 0.89 (3H, t, J=7.6 Hz), 1.53 (2H, sextet, J=7.6 Hz), 3.24 (2H, dt, J=6.4, 7.6 Hz), 3.28 (2H, d, J=7.2 Hz), 3.73 (3H, s), 4.84 (1H, br), 6.32 (1H, dt, J=7.6, 15.6 Hz), 6.49 (1H, d, J=15.6 Hz), 7.17 (2H, d, J=8.4 Hz), 7.27 (1H, brs), 7.46 (2H, d, J=8.4 Hz), and Methyl (E)-4-(4-(N$^3$-isopropyl-N$^2$-cyanoguanidino)phenyl)-3-butenoate $$(\text{CH}_3)_2\text{CH-NH-C(=NCN)-NH-C}_6\text{H}_4\text{-CH=CHCH}_2\text{-C(=O)-OCH}_3$$

yellow solid (yield: 72%)

m.p. (°C.): 136 to 138.5 (recrystallized from n-hexane/ethyl acetate).

EMA for C$_{16}$H$_{20}$N$_4$O$_2$:

|  | C | H | N |
|---|---|---|---|
| calcd (%) | 63.98 | 6.71 | 18.65 |
| found (%) | 64.07 | 6.76 | 18.36 |

NMR (CDCl$_3$, 400 MHz) δ; 1.15 (6H, d, J=6.4 Hz), 3.28 (2H, d, J=7.2 Hz), 3.73 (3H, s), 4.04 (1H, m), 4.59

(1H, d like, J=8 Hz), 6.33 (1H, dt, J=7.2, 16 Hz), 6.49 (1H, d, J=16 Hz), 7.14 (2H, d, J=8.4 Hz), 7.22 (1H, brs), 7.43 (2H, d, J=8.4 Hz)

PRODUCTION EXAMPLE 47

(E)-4-(4-(N³-Ethyl-N²-cyanoguanidino)phenyl)-3-butenoic acid

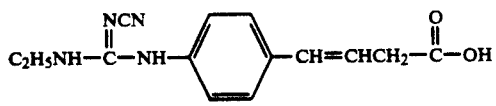

1.20 g of methyl (E)-4-(4-(N³-ethyl-N²-cyanoguanidino)phenyl)-3-butenoate was dissolved in 10 ml of methanol. 9.2 ml of a 1N aqueous sodium hydroxide solution was added to the solution and stirred at room temperature for 8 h. The reaction mixture was filtered. Concentrated hydrochloric acid was added to the filtrate to adjust its pH to 2. A precipitate thus formed was recovered by filtration and washed with water to give 0.86 g of the intended compound in the form of a faint yellow powder (yield: 75%).

m.p. (°C.): 159 to 161 (dec.) (recrystallized from n-hexane/ethyl acetate)

EMA for $C_{14}H_{16}N_4O_2$:

|  | C | H | N |
|---|---|---|---|
| calcd (%) | 61.75 | 5.92 | 20.58 |
| found (%) | 61.63 | 5.95 | 20.56 |

NMR (DHSO-d6, 400 MHz) δ; 1.08 (3H, t, J=7.2 Hz), 3.18 (2H, d, J=6.8 Hz), 3.24 (1H, m), 4.56 (1H, t, J=5.6 Hz), 6.25 (1H, dt, J=6.8, 16 Hz), 6.46 (1H, d, J=16 Hz), 7.19 (2H, d, J=8.8 Hz), 7.38 (2H, d, J=8.8 Hz), 8.92 (1H, s)

The following compounds were produced in the same manner as that described above:

(E)-4-(4-(N³-n-Propyl-N²-cyanoguanidino)phenyl)-3-butenoic acid

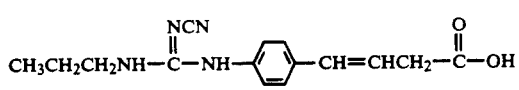

faint yellow powder (yield: 83%)
m.p. (°C.): 156.5 to 158 (dec.) (recrystallized from n-hexane/ethyl acetate)
EMA for $C_{15}H_{18}N_4O_2$:

|  | C | H | N |
|---|---|---|---|
| calcd (%) | 62.92 | 6.34 | 19.57 |
| found (%) | 62.81 | 6.34 | 19.38 |

NMR (DHSO-d6, 400 MHz) δ; 0.86 (3H, t, J=7.2 Hz), 1.51 (2H, sextet, J=7.2 Hz), 3.16 (1H, m), 3.18 (2H, d, J=7.2 Hz), 6.25 (1H, dt, J=7.2, 15.6 Hz), 6.46 (1H, d, J=15.6 Hz), 7.19 (2H, d, J=8.4 Hz), 7.21 (1H, t, J=5.6 Hz), 7.38 (2H, d, J=8.4 Hz), 8.93 (1H, s)

(E)-4-(4-(N³-Isopropyl-N²-cyanoguanidino)phenyl)-3-butenoic acid

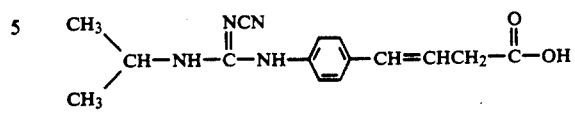

faint yellow powder (yield: 88%)
m.p. (°C.): 155 to 158 (dec.) (recrystallized from n-hexane/ethyl acetate)
EMA for $C_{15}H_{18}N_4O_2$:

|  | C | H | N |
|---|---|---|---|
| calcd (%) | 62.92 | 6.34 | 19.57 |
| found (%) | 62.81 | 6.34 | 19.38 |

NMR (DMSO-d6, 400 MHz) δ; 1.13 (6H, d, J=6.8 Hz), 3.17 (2H, d, J=7.2 Hz), 3.99 (1H, m), 6.24 (1H, dt, J=7.2, 16 Hz), 6.45 (1H, d, J=16 Hz), 7.02 (1H, d, J=8.4 Hz), 7.16 (2H, d, J=8.8 Hz), 7.37 (2H, d, J=8.8 Hz), 8.94 (1H, s)

(E)-4-(4-(N-Oxy-3-pyridyl)phenyl)-3-butenoic acid

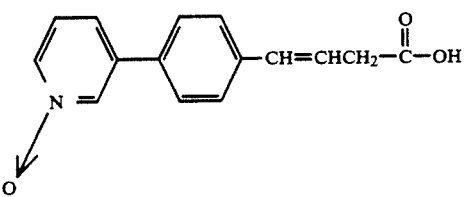

light yellow powder (yield: 75%)
NMR (DMSO-d6, 400 MHz) δ; 3.23 (2H, dd, J=7.0, <1.0 Hz), 6.42 (1H, dt, J=16.0, 7.0 Hz), 6.56 (1H, dt, J=7.0, <1.0 Hz), 7.49 (1H, ddd, J=8.0, 7.0, <1.0 Hz), 7.54 (2H, d, J=8.0 Hz), 7.67 (1H, ddd, J=8.0, 1.5, <1.0 Hz), 7.72 (2H, d, J=8.0 Hz), 8.20 (1H, ddd, J=6.5, 1.0, <1.0 Hz), 8.59 (1H, dd, J=1.5, <1.0 Hz)

(E)-4-(4-(2-Methoxy-5-pyridyl)phenyl)-3-butenoic acid

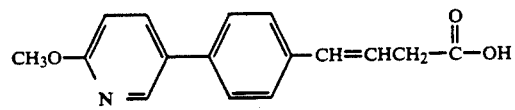

light yellow platy crystals
NMR (DMSO-d6, 400 MHz) δ; 3.23 (2H, dd, J=7.0, 1.0 Hz), 3.96 (3H, s), 6.40 (1H, dt, J=16.0, 7.0 Hz), 6.56 (1H, dt, J=16.0, 1.0 Hz), 6.76 (1H, d, J=8.5 Hz), 7.52 (2H, d, J=8.5 Hz), 7.56 (1H, d, J=7.5 Hz), 7.77 (1H, dd, J=8.5, 7.5 Hz), 8.07 (2H, d, J=8.5 Hz)

PRODUCTION EXAMPLE 48

3-((2-(3,4-Dimethoxyphenyl)ethyl)amino)butyronitrile

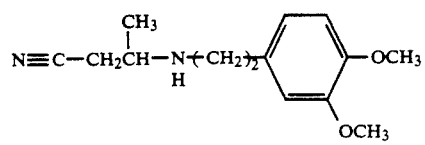

A mixture of 10.0 g of 2-(3,4-dimethoxyphenyl)ethylamine with 14 ml of crotononitrile was stirred at 100° C. for 30 h.

The mixture was concentrated under reduced pressure and the product was purified according to silica gel column chromatography (solvent: ethyl acetate) to give 7.57 g of the intended compound in the form of a light brown oil (yield: 55%).

NMR (CDCl$_3$, 400 MHz) δ; 1.22 (3H, d, J=6.4 Hz), 1.38 (1H, br), 2.43 (2H, d, J=5.6 Hz), 2.70–2.80 (2H, m), 2.81–2.92 (2H, m), 3.04 (1H, m), 3.87 (3H, s), 3.88 (3H, s), 6.74 (1H, d, J=2 Hz), 6.75 (1H, dd, J=2, 8 Hz), 6.81 (1H, d, J=8 Hz)

PRODUCTION EXAMPLE 49

3-(N-(2-(3,4-Dimethoxyphenyl)ethyl-N-methyl)amino)-butyronitrile

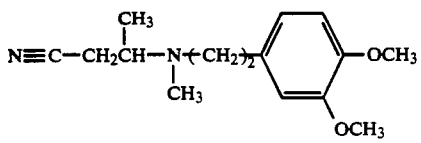

A mixture of 20.0 g of N-methyl-N-(2-(3,4-dimethoxyphenyl)ethylamine with 50 ml of crotononitrile was heated under reflux for 30 h.

The mixture was concentrated under reduced pressure and the product was purified according to silica gel chromatography (solvent: n-hexane/ethyl acetate=3/2) to give 9.49 g of the intended compound in the form of a yellow solid (yield: 35%).

NMR (CDCl$_3$, 400 MHz) δ; 1.17 (3H, d, J=6.8 Hz), 2.30 (1H, dd, J=7.6, 16.8 Hz), 2.31 (3H, s), 2.47 (1H, dd, J=6, 16.8 Hz), 2.56–2.74 (4H, m), 3.15 (1H, m), 3.86 (3H, s), 3.88 (3H, s), 6.73 (1H, d, J=2 Hz), 6.74 (1H, dd, J=2, 8.4 Hz), 6.80 (1H, d, J=8.4 Hz)

PRODUCTION EXAMPLE 50

3-((2-(3,4-Dimethoxyphenyl)ethyl)amino)butylamine

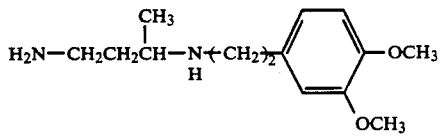

7.57 g of 3-((2-(3,4-dimethoxyphenyl)ethyl)amino)-butyronitrile was dissolved in 60 ml of a solvent. 0.5 g of platinum oxide and 5 ml of concentrated hydrochloric acid were added to the solution and hydrogenation was conducted at room temperature under 3 kg/cm$^2$ for 4 h. The catalyst was filtered off and the product was thoroughly washed with methanol and concentrated under reduced pressure. Dilute aqueous ammonia was added thereto. After extraction with chloroform followed by drying over anhydrous potassium carbonate, the solvent was distilled off. After distillation under reduced pressure, 5.23 g of the intended compound was obtained in the form of a colorless oil (yield: 68%).

bp (°C.); 154–159 (~1 mmHg)

NMR (CDCl$_3$, 400 MHz) δ; 1.05 (3H, d, J=6 Hz), 1.1–1.4 (3H, br), 1.45 (1H, m), 1.55 (1H, m), 2.65–2.85 (6H, m), 2.91 (1H, m), 3.86 (3H, s), 3.87 (3H, s), 6.74 (1H, d, J=2 Hz), 6.75 (1H, dd, J=2, 8.8 Hz), 6.81 (1H, d, J=8.8 Hz)

The following compound was produced in the same manner as that described above:

3-(N-((2-(3,4-dimethoxyphenyl)ethyl)-N-methyl)amino)butylamine

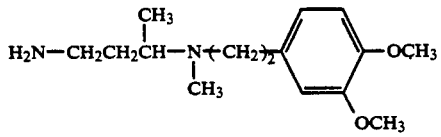

colorless oil
b.p. (°C.); 151–155 (~1 mmHg)

NMR (CDCl$_3$, 90 MHz) δ; 0.93 (3H, d, J=6.3 Hz), 0.93–1.82 (4H, m), 2.12 (3H, s), 2.24–2.93 (7H, m), 3.78 (3H, s), 3.83 (3H, s), 6.54–6.84 (3H, m)

EXAMPLE 53

(E)-[N-(3-(N'-(2-(3,4-Dimethoxyphenyl)ethyl)-N'-methyl)amino)butyl]-4-[5-(1H-imidazol-1-yl)thiophen-2-yl]-3-butenamide

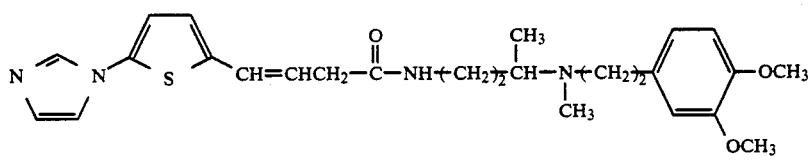

0.59 g of (E)-4-(5-(1H-imidazol-1-yl)thiophen-2-yl)-3-butenoic acid, 0.74 g of 3-((N-(2-(3,4-dimethoxyphenyl)ethyl)-N-methyl)amino)butylamine, 0.57 g of N,N'-dicyclohexylcarbodiimide and 0.37 g of N-hydroxybenzotriazole were added to 9 ml of 50% hydrous acetonitrile and stirred at 70° C. for 30 min. A precipitate thus formed was filtered off and the filtrate was concentrated under reduced pressure. The product was purified according to silica gel column chromatography (solvent: dichloromethane/methanol/concentrated aqueous ammonia=1000/100/3) to give 1.18 g of the intended compound in the form of a yellow oil. (Yield: 98%)

NMR (CDCl$_3$, 400 MHz) δ; 0.95 (3H, d, J=6.8 Hz), 1.49 (1H, m), 1.05 (1H, m), 2.23 (3H, s), 2.56~2.78 (4H, m), 2.87 (1H, m), 2.97 (2H, d, J=7.2 Hz), 3.13 (1H, m), 3.52 (1H, m), 3.84 (3H, s), 3.86 (3H, s), 6.04 (1H, dt, J=7.2 Hz, 15.6 Hz), 6.51 (1H, d, J=15.6 Hz), 6.62~6.71 (2H, m), 6.75 (1H, d, J=3.6 Hz), 6.77 (1H, d, J=8.8 Hz), 6.80 (1H, d, J=3.6 Hz), 7.12 (1H, t, J=1.2 Hz), 7.15 (1H, t, J=1.2 Hz), 7.25 (1H, br), 7.70 (1H, t, J=1.2 Hz)

EXAMPLE 54

(E)-[N-(3-(N'-(2-(3,4-Dimethoxyphenyl)ethyl)amino))-butyl]-4-[5-(1H-imidazol-1-yl)thiophen-2-yl]-3-butenamide

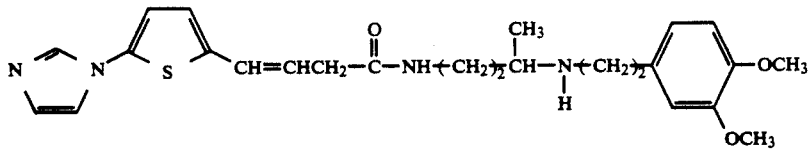

0.59 g of (E)-4-(5-(1H-imidazol-1-yl)thiopen-2-yl)-3-butenoic acid, 0.69 g of 3-((2-(3,4-dimethoxyphenyl)ethyl)amino)butylamine, 0.57 g of N,N'-dicyclohexylcarbodiimide and 0.37 g of N-hydroxybenzotriazole were added to 8 ml of 50% hydrous acetonitrile and stirred at 70° C. for 30 min. A precipitate thus formed was filtered off and the filtrate was concentrated under reduced pressure. An aqueous potassium carbonate solution was added to the residue. After extraction with chloroform followed by drying over anhydrous potassium carbonate, the solvent was distilled out. The product was purified according to silica gel column chromatography (solvent: dichloromethane/methanol/concentrated aqueous ammonia=1000/100/31) to give 1.12 g of the intended compound in the form of a yellow oil. (Yield: 96%)

NMR (CDCl$_3$, 400 MHz) δ; 1.11 (3H, d, J=6.4 Hz), 1.55 (1H, m), 1.62~1.90 (2H, m), 2.64~2.88 (4H, m), 2.94 (1H, m), 3.02 (2H, dd, J=1.2 Hz, 7.2 Hz), 3.30 (1H, m), 3.43 (1H, m), 3.84 (3H, s), 3.86 (3H, s), 6.07 (1H, dt, J=7.2 Hz, 15.6 Hz), 6.54 (1H, dt, J=1.2 Hz, 15.6 hz), 6.66~6.72 (2H, m), 6.77 (1H, d, J=7.2 Hz), 6.78 (1H, d, J=3.6 Hz), 6.82 (1H, d, J=3.6 Hz), 7.13 (1H, t, J=1.2 Hz), 7.15 (1H, d, J=1.2 Hz), 7.29 (1H, br), 7.72 (1H, d, J=1.2 Hz)

EXAMPLE 55

(E)-[N-(4-(N'-(2-(3,5-Dimethoxyphenyl)ethyl)-N'-methyl)amino)butyl]-4-[5-(1,4-hydro-4-oxo-1-pyridyl)thiophen- 2-yl]-3-butenamide

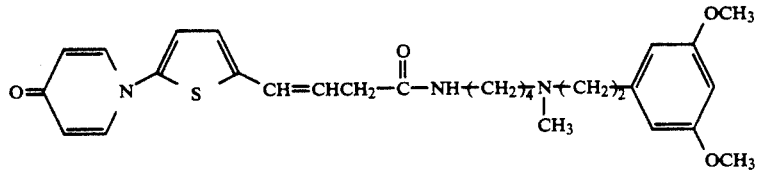

0.65 g of (E)-4-(5-(1,4-dihydro-4-oxo-1-pyridyl)thiophen-2-yl)-3-butenoic acid, 0.73 g of N-methyl-N-(2-(3,5-dimethoxyphenyl)ethyl)-1,4-diaminobutane, 0.57 g of N,N'-dicyclohexylcarbodiimide and 0.37 g of N-hydroxybenzotriazole were added to 8 ml of 50% hydrous acetonitrile and stirred at 70° C. for 30 min. A precipitate thus formed was filtered off, an aqueous potassium carbonate solution was added to the filtrate and the product was extracted with chloroform. The extract was dried over anhydrous potassium carbonate and the solvent was distilled off under reduced pressure. The product was purified according to silica gel column chromatography (solvent: dichloromethane/methanol/concentrated aqueous ammonia=1000/100/3) to give 1.15 g of the intended compound in the form of a light brown oil. (Yield: 90%).

NMR (CDCl$_3$, 400 MHz) δ; 1.58~1.62 (4H, m), 2.30 (3H, s), 2.38~2.42 (2H, m), 2.58~2.66 (2H, m), 2.68~2.74 (2H, m), 3.08 (2H, dd, J=1.2 Hz, 7.2 Hz), 3.12~3.29 (2H, m), 3.77 (6H, s), 6.14 (1H, dt, J=7.2 Hz, 15.6 Hz), 6.31 (1H, t, J=2 Hz), 6.34 (2H, d, J=2 Hz), 6.44 (2H, m), 6.51 (1H, br), 6.54 (1H, dt, J=1.2 Hz, 15.6 Hz), 6.78 (1H, d, J=3.6 Hz), 6.82 (1H, d, J=3.6 Hz), 7.53 (2H, m)

EXAMPLE 56

N-(4-(2-(3,5-Dimethoxyphenyl)ethyl)-N'-methyl)amino)butyl]-4-[5-(1H-imidazol-1-yl)furan-2-yl]-3-butenamide

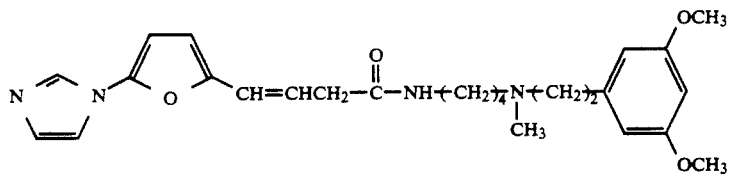

0.55 g of (E)-4-(5-(1H-imidazol-1-yl)furan-2-yl)-3-butenoic acid, 0.69 g of N-methyl-N-(2-(3,5-dimethoxyphenyl)ethyl)-1,4-diaminobutane, 0.57 g of N,N'-dicyclohexylcarbodiimide and 0.37 g of N-hydroxybenzotriazole were added to 8 ml of 50% hydrous acetonitrile and stirred at 70° C. for 30 min. A precipitate thus formed was filtered off and the filtrate was concentrated under reduced pressure. An aqueous potassium carbonate solution was added to the residue and the product was extracted with chloroform. The extract was dried over anhydrous potassium carbonate and the solvent was distilled off. The product was purified according to silica gel column chromatography (solvent: dichloromethane/methanol/concentrated aqueous ammonia=1000/100/3) to give 0.9 g of the intended compound in the form of a yellow oil. (Yield: 77%)

NMR (CDCl$_3$, 400 MHz) δ; 1.50~1.58 (4H, m), 2.28 (3H, s), 2.41 (2H, m), 2.57~2.64 (2H, m), 2.67~2.74 (2H, m), 3.09 (2H, d, J=6.4 Hz), 3.22~3.28 (2H, m), 3.77 (6H, s), 6.14 (1H, d, J=3.6 Hz), 6.23 (1H, dt, J=6.4 Hz, 15.6 Hz), 6.27 (1H, d, J=3.6 Hz), 6.31 (1H, t, J=2.4 Hz), 6.34 (2H, d, J=2.4 Hz), 6.36 (1H, br), 7.16 (1H, t, J=1.2 Hz), 7.25 (1H, t, J=1.2 Hz), 7.85 (1H, t, J=1.2 Hz)

EXAMPLE 57

(E)-[N-(4-(N'-(2-(3,4-Dimethoxyphenyl)ethyl)-N'-methyl)amino)butyl]-4-[4-(N-oxy-4-pyridyl)phenyl]-3-butenamide

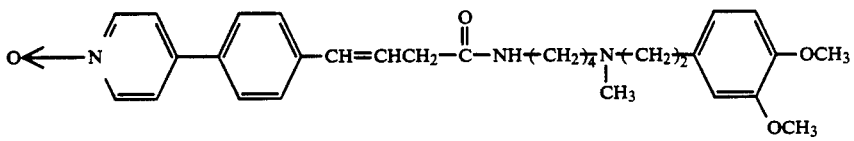

0.67 g of ethyl (E)-4-(4-(N-oxy-4-pyridyl)phenyl)-3-butenoate was dissolved in 50 ml of methanol. 1.0 g of potassium hydroxide was added to the solution and stirred overnight. The solvent was distilled off under reduced pressure. Water was added to the residue and an insoluble matter thus formed was filtered off. Diluted hydrochloric acid was added to the aqueous layer to adjust its pH to 4 to 5. Crystals thus formed were recovered by filtration and dried under reduced pressure to give 0.47 g of a crude carboxylic acid in the form of orangy yellow crystals. This product was subjected to the subsequent reaction without purification.

0.47 g of the crude carboxylic acid, 0.42 g of N,N'-dicyclohexylcarbodiimide and 0.27 g of N-hydroxybenzotriazole were suspended in a mixed solvent comprising 50 ml of acetonitrile and 10 ml of water. 0.54 g of N-methyl-N-(2-(3,4-dimethoxyphenyl)ethyl)-1,4-diaminobutane was added thereto and stirred at 60° C. for 30 min. Crystals thus formed were filtered off and the solvent was distilled off from the filtrate under reduced pressure. The product was purified according to silica gel column chromatography to give 0.50 g of the intended compound in the form of a yellow oil. (Yield: 54%).

NMR (CDCl$_3$, 400 MHz) δ; 1.5~1.6 (4H, m), 2.30 (3H, s), 2.4 (2H, m), 2.6 (2H, m), 2.7 (2H, m), 3.15 (2H, d, J=7.0 Hz), 3.2~3.3 (2H, m), 3.84 (3H, s), 3.86 (3H, s), 6.41 (1H, dt, J=16.0 Hz, 7.0 Hz), 6.49 (1H, m), 6.52 (1H, d, J=16.0 Hz), 6.7~6.75 (2H, m), 6.79 (2H, d, J=8 Hz), 7.4~7.6 (6H, m), 8.23 (2H, m)

EXAMPLE 58

(E)-[N-(3-(N'-(2-(3,4-Dimethoxyphenyl)ethyl)-N'-methyl)amino)butyl]-4-[4-(N$^3$-methyl-N$^2$-cyanoguanidino)phenyl]-3-butenamide

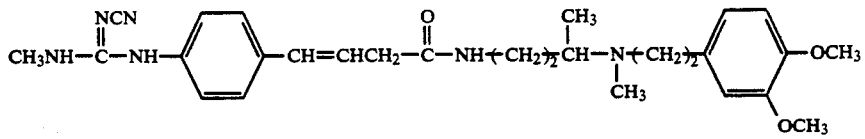

0.65 g of (E)-(4-(4-N$^3$-methyl-N$^2$-cyanoguanidino)-phenyl)-3-butenoic acid, 0.74 g of 3-((N-(2-(3,4-dimethoxyphenyl)ethyl)-N-methyl)amino)butylamine, 0.57 g of N,N'-dicyclohexylcarbodiimide and 0.37 g of N-hydroxybenzotriazole were added to 9 ml of 50% hydrous acetonitrile and stirred at 70° C. for 30 min. A precipitate thus formed was filtered off and the filtrate was concentrated under reduced pressure. An aqueous potassium carbonate solution was added to the residue. The product was extracted with chloroform and the extract was dried over anhydrous potassium carbonate. The solvent was distilled off under reduced pressure and the product was purified according to silica gel column chromatography (solvent: dichloromethane/methanol/concentrated aqueous ammonia=1000/100/3) to give 0.78 g of the intended compound in the form of a light yellow oil. (Yield: 62%)

NMR (CDCl$_3$, 400 MHz) δ; 0.96 (3H, d, J=6.4 Hz), 1.49 (1H, m), 1.66 (1H, m), 2.22 (3H, s), 2.55~2.76 (4H, m), 2.85 (1H, m), 2.86 (3H, d, J=4.8 Hz), 3.00 (2H, d, J=7.2 Hz), 3.13 (1H, m), 3.51 (1H, m), 3.83 (3H, s), 3.84 (3H, s), 5.00 (1H, br), 6.28 (1H, dt, J=7.2 Hz, 16 Hz), 6.42 (1H, d, J=16 Hz), 6.66 (1H, d, J=2 Hz), 6.69 (1H, dd, J=2Hz, 8 Hz), 6.79 (1H, d, J=8 Hz), 7.11 (2H, d, J=8.4 Hz), 7.19 (1H, br), 7.24 (1H, br), 7.35 (2H, d, J=8.4 Hz)

EXAMPLE 59

(E)-[N-(3-(N'-(2-(3,5-Dimethoxyphenyl)ethyl)-N'-methyl)amino)propyl]-4-[4-(N$^3$-methyl-N$^2$-carbamoyl-guanidino)phenyl]-3-butenamide

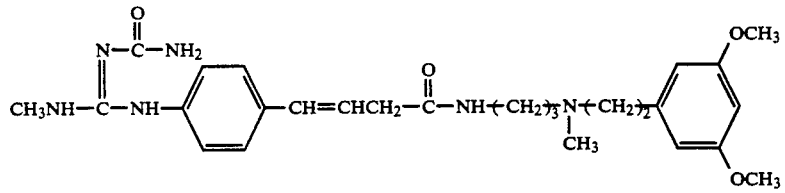

1.00 g of (E)-[N-(3-(N'-(2-(3,5-dimethoxyphenyl)ethyl)-N'-methyl)amino)propyl]-4-[4-(N$^3$-methyl-N$^2$-cyanoguanidino)phenyl]-3-butenamide was dissolved in a mixed solvent comprising 10 ml of methanol and 5 ml of chloroform and the solution was cooled with ice. 2.2 ml of a 4.6M solution of hydrogen chloride in methanol was added thereto and stirred at room temperature for 14 h. The solvent was distilled off under reduced pressure. Dilute aqueous ammonia was added to the residue. The product was extracted with chloroform and dried over anhydrous potassium carbonate. The solvent was distilled off under reduced pressure. The product was purified according to silica gel column chromatography (solvent: dichloromethane/methanol/concentrated aqueous ammonia=1000/100/3) to give 0.82 g of the intended compound in the form of a yellow oil. (Yield: 80%)

NMR (CDCl3, 400 MHz) δ; 1.05~1.65 (4H, m), 2.17 (3H, s), 2.42~2.65 (6H, m), 2.83 (3H, d, J=4.4 Hz), 3.01 (2H, d, J=8 Hz), 3.29~3.38 (2H, m), 3.77 (6H, s), 4.78 (1H, br), 6.19 (1H, dt, J=8 Hz, 16 Hz), 6.26 (2H, d, J=2.4 Hz), 6.31 (1H, t, J=2.4 Hz), 6.41 (1H, d, J=16 Hz), 7.12 (2H, d, J=8.4 Hz), 7.21 (1H, br), 7.28 (1H, br), 7.33 (1H, d, J=8.4 Hz)

EXAMPLES 60 TO 71

Compounds described in Examples 60 to 71 were produced according to the process described in Example 54.

EXAMPLE 60

(E)-[N-(4-(N'-(2-(3,4-Dimethoxyphenyl)ethyl)-N'-methyl)amino)butyl]-4-[5-(1H-imidazol-1-yl)-3-methylthiophen-2-yl]-3-butenamide

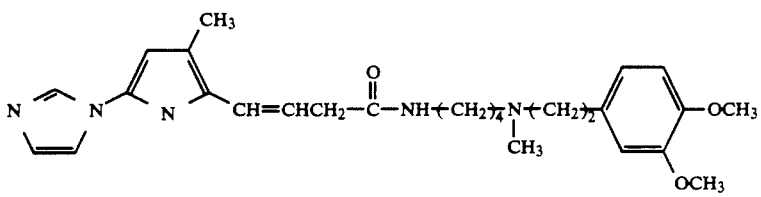

light yellow oil (yield: 57%)

NMR (CDCl3, 400 MHz) δ; 1.5~1.6 (4H, m), 2.21 (3H, s), 2.34 (3H, s), 2.4~2.5 (2H, m), 2.6~2.7 (2H, m), 2.7~2.8 (2H, m), 3.11 (2H, d, J=7.0 Hz), 3.2~3.3 (2H, m), 3.85 (3H, s), 3.87 (3H, s), 6.00 (1H, dt, J=7.0 Hz, 16.0 Hz), 6.48 (1H, m), 6.62 (1H, d, J=16.0 Hz), 6.68 (1H, s), 6.72 (1H, br s), 6.73 (1H, dd, J=2.0 Hz, 7.0 Hz), 6.79 (1H, d, J=7.0 Hz), 7.14 (1H, m), 7.15 (1H, m), 7.72 (1H, m)

EXAMPLE 61

(E)-[N-(4-(N'-(2-(3,4-Dimethoxyphenyl)ethyl)-N'-methyl)amino)butyl]-4-[5-(3-pyridyl)thiophen-2-yl]-3-butenamide

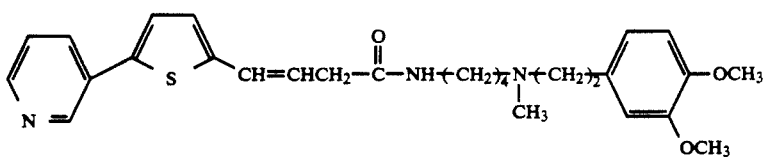

yellow oil (yield: 60%)

NMR (CDCl3, 400 MHz) δ; 1.50~1.66 (4H, m), 2.38 (3H, s), 2.50~2.56 (2H, m), 2.63~2.73 (2H, m), 2.73~2.83 (2H, m), 3.12 (2H, dd, J=8.0 Hz, 1.0 Hz), 3.24~3.31 (2H, m), 3.84 (3H, s), 3.86 (3H, s), 6.18 (1H, dt, J=16.0 Hz, 8.0 Hz), 6.44 (1H, bt, J=5.0 Hz), 6.62 (1H, dt, J=16.0 Hz, 1.0 Hz), 6.70~6.76 (2H, m), 6.78 (1H, d, J=7.0 Hz), 6.72 (1H, d, J=4.0 Hz), 7.21 (1H, d, J=4.0 Hz), 7.29 (1H, ddd, J=8.0 Hz, 5.0 Hz, <1.0 Hz), 7.81 (1H, ddd, J=8.0 Hz, 2.0 Hz, <1.0 Hz), 8.49 (1H, dd, J=5.0 Hz, 2.0 Hz), 8.84 (1H, dd, J=2.0 Hz, <1.0 Hz)

EXAMPLE 62

(E)-[N-(4-(N'-(2-(3,5-Dimethoxyphenyl)ethyl)-N'-methyl)amino)butyl]-4-[5-(3-pyridyl)thiophen-2-yl]-3-butenamide

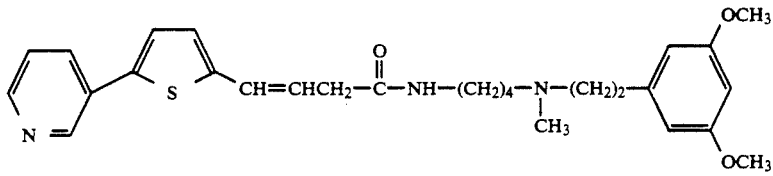

yellow oil (yield: 64%)

NMR (CDCl3, 400 MHz) δ; 1.5~1.6 (4H, m), 2.33 (3H, s), 2.45~2.50 (2H, m), 2.62~2.70 (2H, m), 2.70~2.78 (2H, m), 3.11 (2H, dd, J=7.0 Hz, 1.0 Hz), 3.23~3.50 (2H, m), 3.76 (6H, s), 6.18 (1H, dt, J=16.0 Hz, 8.0 Hz), 6.30~6.36 (3H, m), 6.50 (1H, bt, J=4.0 Hz), 6.61 (1H, dt, J=16.0 Hz, 1.0 Hz), 6.92 (1H, d, J=4.0 Hz), 7.21 (1H d, J=4.0 Hz), 7.29 (1H, ddd, J=8.0 Hz, 5.0 Hz, <1.0 Hz), 7.81 (1H, ddd, J=8.0 Hz, 1.5 Hz, <1.0 Hz), 8.49 (1H, dd, J=5.0 Hz, 1.5 Hz), 8.86 (1H, dd, J=1.5 Hz, <1.0 Hz)

EXAMPLE 63

(E)-[N-(3-(N'-(2-(3,4-Dimethoxyphenyl)ethyl)-N'-methyl)amino)butyl]-4-[4-(3-pyridyl)phenyl]-3-butenamide

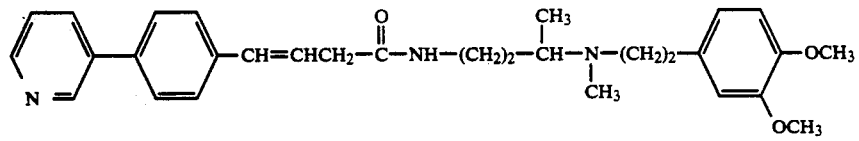

light yellow oil (yield: 98%)

NMR (CDCl$_3$, 400 MHz) δ; 0.93 (3H, d, J=6.4 Hz), 1.48 (1H, m), 1.63 (1H, m), 2.19 (3H, s), 2.51~2.60 (4H, m), 2.84 (1H, br), 3.06 (2H, d, J=7.2 Hz), 3.11 (1H, m), 3.56 (1H, m), 3.82 (3H, s), 3.83 (3H, s), 6.33 (1H, dt, J=7.2 Hz, 15.6 Hz), 6.51 (1H, d, J=15.6 Hz), 6.64 (1H, dd, J=2 Hz, 8 Hz), 6.66 (1H, d, J=2 Hz), 6.75 (1H, d, J=8 Hz), 7.26 (1H, br), 7.35 (1H, ddd, J=1.6 Hz, 2.4 Hz, 8.4 Hz), 7.45 (2H, d, J=8.4 Hz), 7.51 (2H, d, J=8.4 Hz), 7.83 (1H, ddd, J=0.8 Hz, 4.4 Hz, 8.4 Hz), 8.58 (1H, dd, J=1.6 Hz, 4.4 Hz), 8.83 (1H, dd, J=0.8 Hz, 2.4 Hz)

EXAMPLE 64

(E)-[N-(4-(N'-(2-(3,4-Dimethoxyphenyl)ethyl)-N'-methyl)amino)butyl]-4-[4-(N-oxy-3-pyridyl)phenyl]-3-butenamide

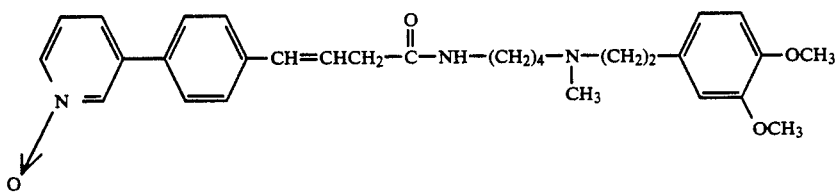

light yellow oil (yield: 66%)

NMR (CDCl$_3$, 400 MHz) δ; 1.5~1.6 (4H, m), 2.30 (3H, s), 2.41~2.46 (2H, m), 2.58~2.64 (2H, m), 2.70~2.76 (2H, m), 3.16 (2H, d, J=7.0 Hz), 3.24~3.30 (2H, m), 3.84 (3H, s), 3.86 (3H, s), 6.42 (1H, dt, J=16.0 Hz, 7.0 Hz), 6.53 (1H, d, J=16.0 Hz), 6.58 (1H, bt, J=4.5 Hz), 6.70~6.76 (2H, m), 6.79 (1H, d, J=8.5 Hz), 7.30~7.36 (1H, m), 7.44~7.48 (5H, m), 8.18 (1H bd, J=6.5 Hz), 8.44 (1H, br s)

EXAMPLE 65

(E)-[N-(4-(N'-(2-(3,4-Dimethoxyphenyl)ethyl)-N'-methyl)amino)butyl]-4-[4-(2-methoxy-5-pyridyl)phenyl]-3-butenamide

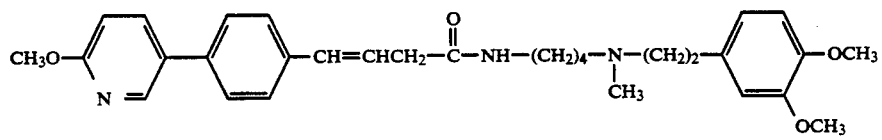

white solid (yield: 98%)

NMR (CDCl$_3$, 400 MHz) δ; 1.50~1.58 (4H, m), 2.31 (3H, s), 2.40~2.48 (2H, m), 2.56~2.66 (2H, m), 2.70~2.80 (2H, m), 3.15 (2H, dd, J=7.0 Hz, 1.0 Hz), 3.24~3.30 (2H, m), 3.83 (3H, s), 3.85 (3H, s), 4.03 (3H, s), 6.34 (1H, m), 6.37 (1H, dt, J=16.0 Hz, 7.0 Hz), 6.55 (1H, d, J=16.0 Hz), 6.67 (1H, dd, J=8.0 Hz, <1.0 Hz), 6.70~6.73 (2H, m), 6.77 (1H, d, J=9.0 Hz), 7.32 (1H, dd, J=7.5 Hz, <1.0 Hz), 7.44 (2H, d, J=8.5 Hz), 7.61 (1H, dd, J=8.0 Hz, 7.5 Hz), 8.00 (2H, d, J=8.5 Hz)

EXAMPLE 66

(E)-[N-(4-(N'-(2-(3,4-Dimethoxyphenyl)ethyl)-N'-methyl)amino)butyl]-4-[4-(1,2-dihydro-1-methyl-2-oxo-5-pyridyl)phenyl]-3-butenamide

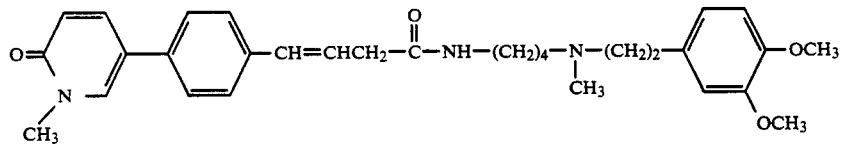

light yellow oil (yield: 100%)

NMR (CDCl$_3$, 400 MHz) δ; 1.53~1.62 (4H, m), 2.34 (3H, s), 2.46~2.50 (2H, m), 2.61~2.68 (2H, m), 2.73~2.78 (2H, m), 3.15 (2H, d, J=7.0 Hz), 3.25~3.30 (2H, m), 3.62 (3H, s), 3.85 (3H, s), 3.86 (3H, s), 6.36 (1H, dd, J=15.5 Hz, 7.0 Hz), 6.51 (1H, d, J=15.5 Hz), 6.52 (1H, m), 6.65 (1H, d, J=9.0 Hz), 6.71~6.75 (2H, m), 6.79 (1H, d, J=8.5 Hz), 7.34 (2H, d, J=8.5 Hz), 7.40 (2H, d, J=8.5 Hz), 7.50 (1H, d, J=3.0 Hz), 7.62 (1H, dd, J=9.0 Hz, 3.0 Hz)

EXAMPLE 67

(E)-[N-(3-(N'-(2-(3,5-Dimethoxyphenyl)ethyl)-N'-methyl)amino)propyl]-4-[4-(N³-ethyl-N²-cyanoguanidino)phenyl]-3-butenamide

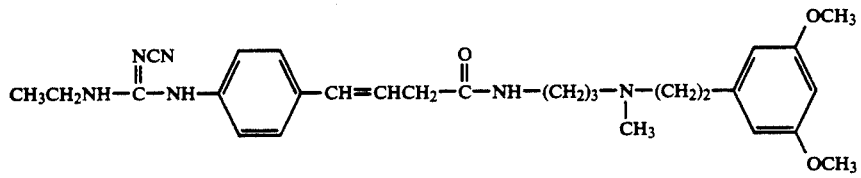

light yellow amorphous product (yield: 70%)

NMR (CDCl$_3$, 400 MHz) δ; 1.13 (3H, t, J=6.8 Hz), 1.59~1.70 (2H, m), 2.20 (3H, s), 2.49~2.58 (4H, m), 2.60~2.66 (2H, m), 3.02 (2H, d, J=7.2 Hz), 3.26~3.38 (4H, m), 3.77 (6H, s), 6.24 (2H, d, J=2 Hz), 6.27 (1H, dt, J=7.2 Hz, 16 Hz), 6.32 (1H, t, J=2 Hz), 6.43 (1H, d, J=16 Hz), 7.00 (1H, br), 7.12 (2H, d, J=8.4 Hz), 7.25 (1H, br), 7.39 (2H, d, J=8.4 Hz)

EXAMPLE 68

(E)-[N-(3-(N'-(2-(3,5-Dimethoxyphenyl)ethyl)-N'-methyl)amino)propyl]-4-[4-(N³-isopropyl-N²-cyanoguanidino)phenyl]-3-butenamide

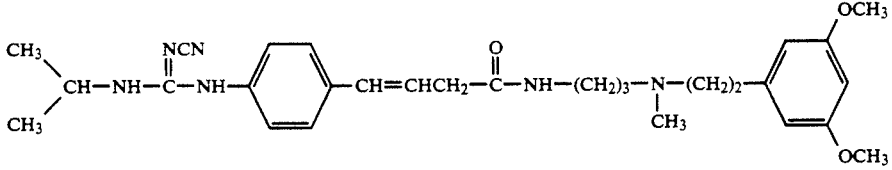

light yellow oil (CDCl$_3$, 400 MHz)

NMR (CDCl$_3$, 400 MHz) δ; 1.14 (3H, d, J=6.4 Hz), 1.61~1.72 (2H, m), 2.22 (3H, s), 2.51~2.61 (4H, m), 2.62~2.68 (2H, m), 3.02 (2H, dd, J=0.8 Hz, 7.2 Hz), 3.33~3.38 (2H, m), 3.78 (6H, s), 4.03 (1H, m), 4.56 (1H, br), 6.21~6.35 (4H, m), 6.44 (1H, dt, J=0.8 Hz, 16 Hz), 6.94 (1H, br), 7.11 (2H, d, J=8.4 Hz), 7.24 (1H, br), 7.40 (2H, d, J=8.4 Hz)

EXAMPLE 69

(E)-[N-(4-(N'-(2-(3,5-Dimethoxyphneyl)ethyl)-N'-methyl)amino)butyl]-4-[4-(N³-ethyl-N²-cyanoguanidino)phenyl]-3-butenamide

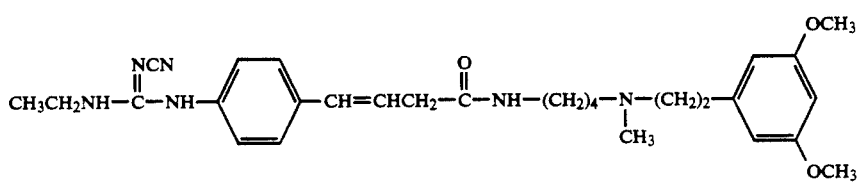

yellow oil (yield: 89%)

NMR (CDCl$_3$, 400 MHz) δ; 1.13 (3H, t, J=7.2 Hz), 1.52~1.61 (4H, m), 2.29 (3H, s), 2.41~2.48 (2H, m), 2.61~2.67 (2H, m), 2.69~2.76 (2H, m), 3.11 (2H, d, J=7.2 Hz), 3.22~3.29 (2H, m), 3.29~3.36 (2H, m), 3.78 (6H, s), 4.81 (1H, br), 6.30~6.39 (4H, m), 6.41 (1H, br), 6.49 (1H, d, J=16 Hz), 7.00 (1H, br), 7.14 (2H, d, J=8.4 Hz), 7.42 (2H, d, J=8.4 Hz)

EXAMPLE 70

(E)-[N-(4-(N'-(2-(3,5-Dimethoxyphenyl)ethyl)-N'-methyl)amino)butyl]-4-[4-(N³-n-propyl-N²-cyanoguanidino)phenyl]-3-butenamide

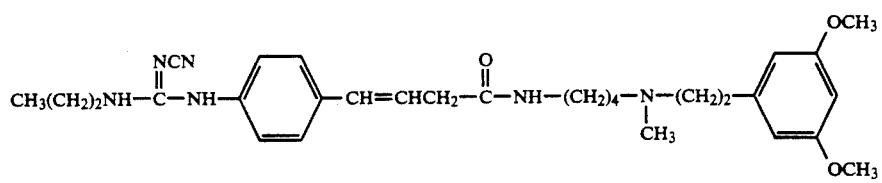

yellow oil (yield: 75%)

NMR (CDCl$_3$, 400 MHz) δ; 0.89 (3H, t, J=7.2 Hz), 1.48~1.60 (6H, m), 2.32 (3H, s), 2.43~2.49 (2H, m), 2.63~2.69 (2H, m), 2.71~2.77 (2H, m), 3.12 (2H, d, J=6.8 Hz), 3.21~3.29 (4H, m), 3.78 (6H, s), 4.86 (1H, br), 6.29~6.39 (4H, m), 6.43 (1H, br), 6.49 (1H, d, J=16.4 Hz), 7.06 (1H, br), 7.14 (2H, d, J=8.4 Hz), 7.42 (2H, d, J=8.4 Hz)

EXAMPLE 71

(E)-[N-(4-(N'-(2-(3,5-Dimethoxyphenyl)ethyl)-N'-methyl)amino)butyl]-4-[4-(N$^3$-isopropyl-N$^2$-cyanoguanidino)phenyl]-3-butenamide

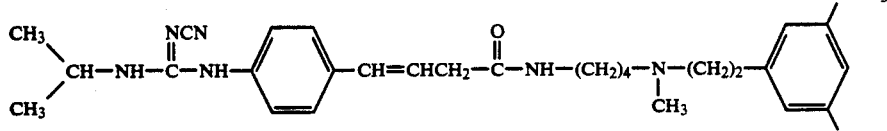

yellow oil (yield: 54%)

NMR (CDCl$_3$, 400 MHz) δ; 1.13 (6H, d, J=6.4 Hz), 1.52~1.60 (4H, m), 2.32 (3H, s), 2.43~2.49 (2H, m), 2.64~2.69 (2H, m), 2.71~2.78 (2H, m), 3.12 (2H, d, J=7.2 Hz), 3.23~3.28 (2H, m), 3.78 (6H, s), 4.60 (1H, d, J=5.6 Hz), 6.30~6.39 (4H, m), 6.43 (1H, br), 6.49 (1H, d, J=16 Hz), 7.04 (1H, br), 7.12 (2H, d, J=8.4 Hz), 7.42 (2H, d, J=8.4 Hz)

We claim:

1. A butenoic acid compound having the formula (I) or a pharmacologically acceptable salt thereof:

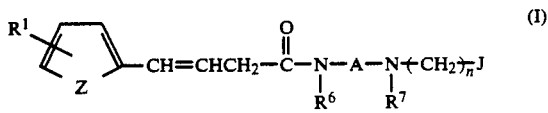

wherein
R$^1$ represents an imidazole group;
Z represents an azomethyne (—N=CH—) group,
R$^6$ and R$^7$ may be the same or different from each other and each represent a hydrogen atom or a lower alkyl, cycloalkyl or allyl group;
A represents a C$_{1~6}$ alkylene group which may have a lower alkyl or hydroxy-substituted lower alkyl substituent bonded to any carbon of the group;
J represents a group of the formula:

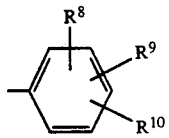

wherein R$^8$, R$^9$ and R$^{10}$ may be the same or different, each represent a hydrogen or halogen atom, a lower alkyl, lower alkoxy, hydroxyl, nitro, cyano, trifuloromethyl group, a group represented by the formula:

wherein R$^{11}$ and R$^{12}$ may be the same or different and each represent a hydrogen atom or a lower alkyl group, or an alkanoylamino group, or any two members of R$^8$, R$^9$ and R$^{10}$ may form an alkylenedioxy group together with adjacent carbon atoms; and n represents an integer of 1 to 6.

2. The compound or salt as claimed in claim 1, in which the compound has the formula (A):

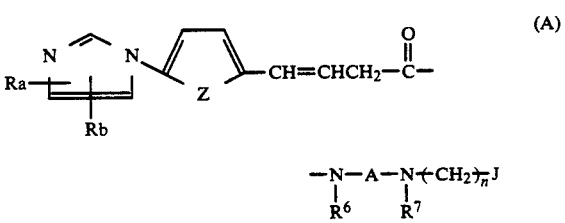

wherein Ra and Rb are, independently of each other, hydrogen, nitro, cyano, trifluoromethyl, an alkylsulfonyl, an arylsulfonyl, a halogen or a lower alkylcarbonyl; Z is azomethyne; A' is an alkylene having 4 to 6 carbon atoms; and n is an integer of 1 to 6.

3. A pharmacological composition which comprises a pharmacologically effective amount of the compound or salt as defined in claim 1 and a pharmacologically acceptable carrier.

4. A method for treating, remitting or ameliorating ischemic heart diseases by administering the compound or salt defined in claim 1 in a pharmacologically effective amount to a human being.

* * * * *